(12) United States Patent
Viertelhaus et al.

(10) Patent No.: US 11,292,784 B2
(45) Date of Patent: Apr. 5, 2022

(54) CRYSTALLINE FORMS OF ETHYL 2-[[3-[[3-CHLORO-5-FLUORO-6-[3-METHYL-2,6-DIOXO-4-(TRIFLUOROMETHYL)PYRIMIDIN-1-YL]-2-PYRIDYL]OXY]ACETATE

(71) Applicant: BASF SE, Ludwigshafen (DE)

(72) Inventors: Martin Viertelhaus, Ludwigshafen (DE); Rolf Hellmann, Ludwigshafen (DE); Dennis Koulelis, Ludwigshafen (DE); Tobias Seiser, Limburgerhoff (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 16/764,432

(22) PCT Filed: Nov. 8, 2018

(86) PCT No.: PCT/EP2018/080597
§ 371 (c)(1),
(2) Date: May 15, 2020

(87) PCT Pub. No.: WO2019/101533
PCT Pub. Date: May 31, 2019

(65) Prior Publication Data
US 2020/0354337 A1 Nov. 12, 2020

(30) Foreign Application Priority Data
Nov. 27, 2017 (EP) ..................................... 17203844

(51) Int. Cl.
*C07D 401/14* (2006.01)
(52) U.S. Cl.
CPC ........ *C07D 401/14* (2013.01); *C07B 2200/13* (2013.01)
(58) Field of Classification Search
CPC combination set(s) only.
See application file for complete search history.

(56) References Cited

FOREIGN PATENT DOCUMENTS

| WO | WO-02/098227 A1 | 12/2002 |
|---|---|---|
| WO | WO-2017/198859 A1 | 11/2017 |
| WO | WO-2017/202768 A1 | 11/2017 |
| WO | WO-2018/015180 A1 | 1/2018 |
| WO | WO-2018/019552 A1 | 2/2018 |
| WO | WO-2018/019554 A1 | 2/2018 |
| WO | WO-2018/019555 A1 | 2/2018 |
| WO | WO-2018/019574 A1 | 2/2018 |
| WO | WO-2018/019721 A1 | 2/2018 |
| WO | WO-2018/019755 A1 | 2/2018 |
| WO | WO-2018/019758 A1 | 2/2018 |
| WO | WO-2018/019765 A1 | 2/2018 |
| WO | WO-2018/019767 A1 | 2/2018 |
| WO | WO-2018/019770 A1 | 2/2018 |
| WO | WO-2018/019842 A1 | 2/2018 |
| WO | WO-2018/019845 A1 | 2/2018 |
| WO | WO-2018/019860 A1 | 2/2018 |
| WO | WO-2018/024695 A1 | 2/2018 |
| WO | WO-2018/024696 A1 | 2/2018 |
| WO | WO-2018/029029 A1 | 2/2018 |
| WO | WO-2018/029030 A1 | 2/2018 |
| WO | WO-2018/029031 A1 | 2/2018 |
| WO | WO-2018/108695 A1 | 6/2018 |
| WO | WO-2018/114759 A1 | 6/2018 |
| WO | WO-2018/153707 A1 | 8/2018 |
| WO | WO-2018/178039 A1 | 10/2018 |
| WO | WO-2018/229041 A1 | 12/2018 |
| WO | WO-2019/101513 A1 | 5/2019 |
| WO | WO-2019/101533 A1 | 5/2019 |
| WO | WO-2019/101551 A1 | 5/2019 |

OTHER PUBLICATIONS

European Search Report for EP Patent Application No. 17203844.0, dated Jun. 11, 2018, 3 pages.
International Application No. PCT/EP2018/080597, International Search Report and Written Opinion, dated Jan. 31, 2019.

*Primary Examiner* — Heidi Reese
(74) *Attorney, Agent, or Firm* — Marshall, Gerstein & Borun LLP

(57) ABSTRACT

The present invention relates to crystalline forms of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate, herein after also referred to as "compound of formula (I)". The invention also relates to a process for the production of these crystalline forms, formulations for plant protection and herbicidal compositions which contain one of these crystalline forms.

12 Claims, 4 Drawing Sheets

CRYSTALLINE FORMS OF ETHYL 2-[[3-[[3-CHLORO-5-FLUORO-6-[3-METHYL-2,6-DIOXO-4-(TRIFLUOROMETHYL)PYRIMIDIN-1-YL]-2-PYRIDYL]OXY] ACETATE

CROSS-REFERENCE TO RELATED APPLICATIONS

This is the U.S. national phase of International Application No. PCT/EP2018/080597, filed Nov. 8, 2018, which claims the benefit of European Patent Application No. 17203844.0, filed on Nov. 27, 2017, incorporated herein by references in its entirety.

The present invention relates to crystalline forms of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate, herein after also referred to as "compound of formula (I)".

The invention also relates to a process for the production of these crystalline forms and formulations for plant protection which contain one of these crystalline forms The present invention also provides herbicidal compositions comprising at least one of these crystalline forms (component A) and at least one further compound selected from the herbicidal compounds B (component B) and safeners C (component C).

The compound of formula (I) is the herbicidal active substance of the formula (I):

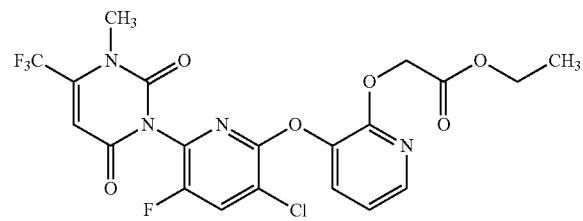 [SMILES: CCOC(=O)COc1ncccc1Oc1nc(-n2c(=O)cc(C(F)(F)F)n(C)c2=O)c(F)cc1Cl]

(I)

The compound of formula (I) and a general procedure for its production is known from WO 2017/202768.

For the production of active substances on the industrial scale but also for the formulation of active substances, in many cases knowledge concerning the possible existence of crystalline modifications (also described as crystalline forms) or of solvates of the active substance in question, and knowledge of the specific properties of such modifications and solvates and of methods for their preparation are of decisive importance. A range of active substances can exist in different crystalline but also in amorphous modifications. Polymorphism is the term used in these cases. A polymorph is a solid, crystalline phase of a compound which is characterized by a specific, uniform packing and arrangement of the molecules in the solid.

Different modifications of one and the same active substance can sometimes have different properties, for example differences in the following properties: solubility, vapor pressure, dissolution rate, stability against a phase change into a different modification, stability during grinding, suspension stability, optical and mechanical properties, hygroscopicity, crystal form and size, filterability, density, melting point, stability to decomposition, color, chemical reactivity or biological activity.

The applicant's own attempts to convert the compound of formula (I) into a crystalline solid by crystallization at first resulted in amorphous products or in complex mixtures of different crystal modifications, which could only be handled with difficulty and whose stability against uncontrolled phase change was unsatisfactory.

It has now surprisingly been found that by suitable processes previously unknown crystalline, stable modifications of the compounds of formula (I), which do not display the disadvantages of the amorphous compound of formula (I) are obtained in high purity. These modifications are also described below as form A, form B, form C and form D.

The terms "pure form A", "pure form B", "pure form C", and "pure form D" should be understood to mean that the proportion of the modification in question, based on the total quantity of the compound of formula (I), is at least 90 wt. % and in particular at least 95 wt. %.

The general preparation of the compound of formula (I) can be effected e.g. by reaction of amines of formula (II) with oxazinones of formula (III) in the presence of an acid:

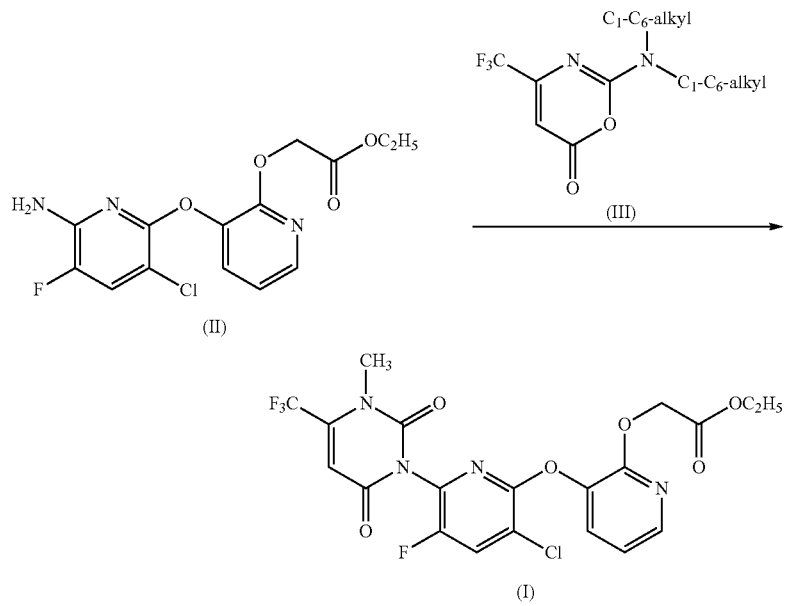

The reaction may in principle be carried out in substance. However, preference is given to reacting the amines of formula (II) with the oxazinones of formula (III) in an organic solvent.

Suitable in principle are all solvents which are capable of dissolving the amines of formula (II) and the oxazinones of formula (III) at least partly, and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; alcohols such as methanol, ethanol, n-propanol, isopropanol, n-butanol and tert.-butanol, organic acids like formic acid, acetic acid, propionic acid, oxalic acid, methylbenzenesulfonic acid, benzenesulfonic acid, camphorsulfonic acid, citric acid, trifluoroacetic acid as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are organic acids as mentioned above.

It is also possible to use mixtures of the solvents mentioned.

As acids an organic acids like hydrochloric acid, hydrobromic acid or sulfuric acid, as well as organic acids like formic acid, acetic acid, propionic acid, oxalic acid, methylbenzenesulfonic acid, benzenesulfonic acid, camphorsulfonic acid, citric acid, trifluoroacetic acid, can be used.

The acids are generally employed in equimolar amounts, in excess or, if appropriate, be used as solvent, however they can also be employed in catalytic amounts.

Amines of formula (II) can be obtained from the corresponding pyridines of formula (IV):

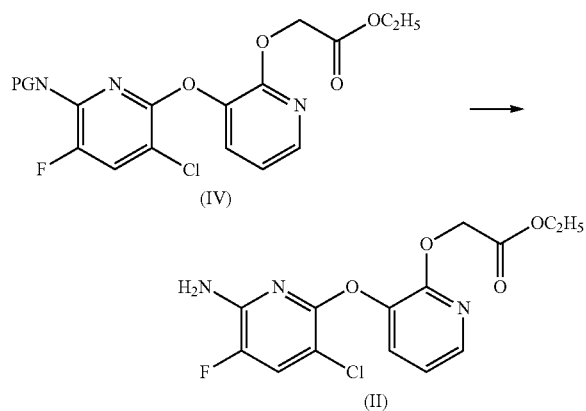

Within the pyridines of formula (IV), the group "PGN" is a protected amine substituent selected from the group consisting of $N_3$, aliphatic or aromatic carbamates, aliphatic or aromatic amides, N—$C_1$-$C_6$-alkyl-amines, N-aryl-amines or heteroarylamides.

Preferably PGN is selected from the group consisting of $N_3$, $C_1$-$C_6$-alkyl-O(CO)NH—, $C_1$-$C_6$-haloalkyl-O(CO)—NH—, (tri-$C_1$-$C_6$-alkyl)-Si—$C_1$-$C_6$-alkyl-O(CO)NH—, $C_2$-$C_6$-alkenyl-O(CO)NH—, $C_3$-$C_6$-alkynyl-O(CO)NH—, $C_3$-$C_6$-cycloalkyl-O(CO)NH—, fluorenylmethyl-O(CO)NH—, H(CO)N—, $C_1$-$C_6$-alkyl-(CO)—NH—, $C_1$-$C_6$-haloalkyl-(CO)—NH—, $C_1$-$C_6$-alkyl-NH, di($C_1$-$C_6$-alkyl)-N—, ($C_1$-$C_6$-alkyoxy-$C_1$-$C_4$-alkyl)NH—, di($C_1$-$C_6$-alkyoxy-$C_1$-$C_4$-alkyl)N—, $C_2$-$C_6$-alkenyl-NH, di($C_2$-$C_6$-alkenyl)N—, (tri-$C_1$-$C_4$-alkyl)-Si—$C_1$-$C_4$-alkoxy-$C_1$-$C_4$-alkyl-NH—, di[(tri-$C_1$-$C_4$-alkyl)-Si—$C_1$-$C_4$-alkoxy-$C_1$-$C_4$-alkyl]N—, fluorenylmethyl-NH—, di(fluorenylmethyl)N—, N-phthalimide, N-2,3-dimethylmaleimide or N-2,5-dimethylpyrrole, phenyl-O(CO)NH—, phenyl-$C_1$-$C_4$-alkyl-O(CO)NH—, phenyl-(CO)NH—, phenyl-$C_1$-$C_6$-alkyl-(CO)NH—, pyridyl-(CO)—NH—, ortho-($C_1$-$C_4$-alkoxy)-phenyl-NH, di[ortho-($C_1$-$C_4$-alkoxy)-phenyl]N—, para-($C_1$-$C_4$-alkoxy)-phenyl-NH, di[para-($C_1$-$C_4$-alkoxy)-phenyl]N—, phenyl-$C_1$-$C_4$-alkyl-NH—, di(phenyl-$C_1$-$C_4$-alkyl)N—, para-($C_1$-$C_4$-alkoxy)-phenyl-$C_1$-$C_4$-alkyl-NH, di[para-($C_1$-$C_4$-alkoxy)-phenyl-$C_1$-$C_4$-alkyl]N—, wherein each phenyl or pyridyl ring can be substituted by one to three substituents selected from the group consisting of halogen, CN, $NO_2$, $C_1$-$C_4$-alkyl, $C_1$-$C_4$-alkoxy, $C_1$-$C_4$-alkylsulfinyl and $C_1$-$C_4$-alkylsulfonyl;

more preferably PGN is selected from the group consisting of $C_1$-$C_6$-alkyl-O(CO)NH—, fluorenylmethyl-O(CO)NH—, H(CO)N—, $C_1$-$C_6$-alkyl-(CO)—NH—, $C_1$-$C_6$-haloalkyl-(CO)—NH, N-phthalimide, phenyl-O(CO)NH—, phenyl-$C_1$-$C_4$-alkyl-O(CO)NH—, phenyl-$C_1$-$C_4$-alkyl-NH—, di(phenyl-$C_1$-$C_4$-alkyl)N—, wherein each phenyl or pyridyl ring can be substituted by one to three $C_1$-$C_4$-alkoxy substituents.

In case "PGN" is an azide substituent, the pyridines of formula (IV) can be converted into the amine of formula (II) using reductive reaction conditions, such as zinc in an aqueous ammonium chloride solution.

In case "PGN" is an acylated amine substituent, the pyridines of formula (IV) can be converted into the amines of formula (II) using acid.

The use and choice of the "PGN" substituent and appropriate deprotection methods will be apparent to one skilled in chemical synthesis (see, for example, Greene, T. W.; Wuts, P. G. M. Protective Groups in Organic Synthesis, 4th ed.; Wiley: New York, 2007).

Oxazinones of formula (III) are commercially available or can be prepared by known methods (WO 2000/049002).

Pyridines of formula (IV) can be prepared by reaction of compounds of formula (V) with compounds of formula (VI) in the presence of a base:

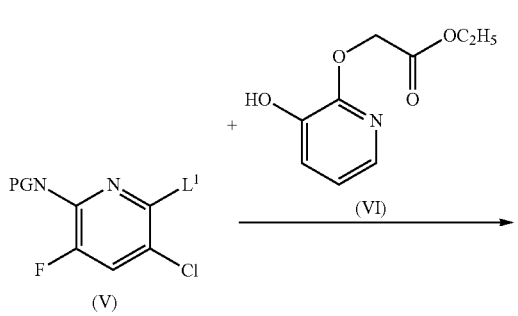

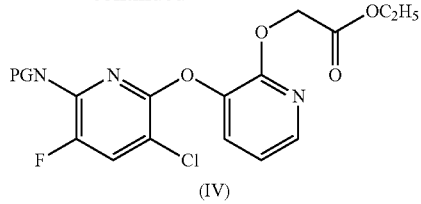

(IV)

Within the compounds of formula (V), $L^1$ is a leaving group such halogen, $C_1$-$C_6$-alkylsulfonate or arylsulfonate; preferably F, Cl, $C_1$-$C_6$-alkylsulfonate or arylsulfonate; especially preferred F, Cl, mesylat or tosylat; more preferred F or Cl.

Within the compounds of formulae (IV) and (V), the group "PGN" is a protected amine substituent as defined above for the amines of formula (II).

The reaction may in principle be carried out in substance. However, preference is given to reacting the compounds of formula (V) with the compounds of formula (VI) in an organic solvent.

Suitable in principle are all solvents which are capable of dissolving the compounds of formula (V) and the compounds of formula (VII) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, nitriles, ketones and dipolar aprotic solvents as mentioned above.

More preferred solvents are ethers and dipolar aprotic solvents as mentioned above.

It is also possible to use mixtures of the solvents mentioned.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as trimethylamine, triethylamine, diisopropylethylamine and N-methylpiperidine, pyridine, substituted pyridines such as collidinge, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; ammonia, pyridine, lutidine, collidine, 4-(dimethylamino) pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal hydrides, alkali metal and alkaline earth metal carbonates, as well as alkali metal hydrogen carbonates (bicarbonates); alkali metal and alkaline earth metal phosphates; metal organic compounds, alkyl magnesium halides as well as alkali metal and alkaline earth metal alkoxides; and furthermore organic bases, such as tertiary amines, pyridine, substituted pyridines and also bicyclic amines.

Especially preferred bases are alkali metal and alkaline earth metal carbonates, metal organic compounds, alkyl magnesium halides as well as alkali metal and alkaline earth metal alkoxides; and furthermore organic bases, such as tertiary amines, pyridine, substituted pyridines and also bicyclic amines.

The term base as used herein also includes mixtures of two or more, preferably two of the above compounds. Particular preference is given to the use of one base.

The bases are generally employed in equimolar amounts or in excess; however they can also be employed as solvent, or, if appropriate, in catalytic amounts.

The bases are generally used in excess, more preferably with from 1 to 20 mole equivalents based on the compound of formula (VI), and they may also be used as the solvent.

Preferably, the bases are used at from 1 to 5 mole equivalents, very preferably at from 1 to 3 mole equivalents, more preferably at 1 to 2 mole equivalents, based on the compound of formula (VI).

It may be advantageous to add the base offset over a period of time.

The compounds of formula (VI) are commercially available or can be prepared by known methods (e.g. WO 02/098227 or WO 07/083090).

The compounds of formula (V) required for the preparation of pyridines of formula (XXII) are commercially available or can be prepared by known methods from the corresponding amine XV (e.g. Greene, T. W.; Wuts, P. G. M. Protective Groups in Organic Synthesis, 4th ed.; Wiley: New York, 2007).

Accordingly, a first object of the present invention relates to the crystalline form A of the compound of formula (I). Also an object is a compound of formula (I) which at least 90 wt. %, in particular at least 95% consists of the crystalline form A.

The form A according to the invention can be identified by X-ray powder diffractometry on the basis of its diffraction diagram. Thus an X-ray powder diffraction diagram recorded using Cu-Kα radiation (1.54178 Å) at 25° C. shows at least 3, often at least 5, in particular at least 7, and especially all of the reflections quoted in the following table as ° 2θ values or as interplanar spacings d:

| ° 2θ |
|---|
| 4.7 ± 0.2 |
| 7.5 ± 0.2 |
| 9.5 ± 0.2 |
| 12.2 ± 0.2 |
| 12.9 ± 0.2 |
| 13.7 ± 0.2 |
| 14.3 ± 0.2 |
| 14.5 ± 0.2 |
| 19.3 ± 0.2 |
| 20.1 ± 0.2 |
| 24.7 ± 0.2 |

Preferably, an X-ray powder diffraction diagram recorded using Cu-Kα radiation (1.54178 Å) at 25° C. shows the following reflections as ° 2θ values: 4.7±0.2, 7.5±0.2, 9.5±0.2 and 24.7±0.2.

Form A displays a thermogram with a characteristic melting peak in the range from 50 to 80° C. The melting point, determined as the onset of the melting peak, typically lies at 60° C. The values quoted here relate to values determined by differential calorimetry (differential scanning calorimetry, DSC; heating rate 10° C./min).

The production of the form A of the compound of formula (I) according to the invention is effected by
  by crystallization from a solution of the compound of formula (I)
  by crystallization from a solution of the compound of formula (I) in a suitable organic solvent The solution of compound of formula (I) can for example be prepared by the following methods:
(1) Dissolution of the compound of formula (I), preferably in a form different from form A, in one of the solvents mentioned below, or
(2) Preparation of the compound of formula (I) by a chemical reaction and transfer of the reaction mixture, if necessary after removal of reagents and/or side products, into an organic solvent suitable according to the invention.

For the preparation of the solution by dissolution of the compound of formula (I), essentially any known form of compound of formula (I) can be used. Often amorphous compound of formula (I) or a mixture of different crystalline modifications or a mixture of amorphous and crystalline compound of formula (I) will be used. Also suitable are crystalline forms of compound of formula (I) and mixtures thereof, for example the form B according to the invention, the form C described below, and also the form D described below and mixtures of these forms.

The dissolution of the compound of formula (I) is usually effected at room temperature.

In one embodiment of the invention, the dissolution of the compound of formula (I) is effected at elevated temperature, and naturally the temperature used for dissolution will not exceed the boiling point of the solvent.

The solution of the compound of formula (I) can also be prepared by transferring a reaction mixture obtained by a chemical reaction, which contains the compound of formula (I), if necessary after removal of reagents and/or side products, into an organic solvent suitable according to the invention. This can be effected in such a manner that the reaction is performed in an organic solvent or solvent mixture which consists at least partly, preferably at least 50 wt. %, of a solvent suitable for the crystallization and, if necessary a workup is performed during which excess reagents and any catalysts present and any unsuitable solvents present, for example water and/or methanol, are removed. The preparation of a solution of the compound of formula (I) by chemical reaction of a suitable precursor of compound of formula (I) can be effected by analogy to the methods which are described in the state of the art cited at the beginning, to which full reference is hereby made.

The production of the form A of the compound of formula (I) according to the invention is effected by crystallization from a solution of the compound of formula (I) in a suitable organic solvent.

Suitable solvents for the crystallization of form A are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; alcohols such as methanol, ethanol, n-propanol, isopropanol, n-butanol and tert.-butanol, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP), water, and mixtures of the afore-mentioned solvents.

Preferred solvents are aliphatic hydrocarbons, ethers and alcohols as described above, more preferred alcohols.

In order to obtain form A of the compound of formula (I), the crystallization is preferably effected at room temperature.

Crystallization of form A is preferably effected under controlled conditions, i.e. the conditions of the crystallization are chosen to achieve a slow crystallization rate.

For this, in a first step i) a solution of the compound of formula (I) in one of the aforesaid organic solvents is prepared, and then in a second step ii) crystallization of the compound of formula (I) is effected.

The concentration of compound of formula (I) in the solution used for the crystallization of form A naturally depends on the nature of the solvent, the solution temperature and the form of the solved compound of formula (I) (i.e. amorphous or crystalline), and often lies in the range from 5 to 1500 g/l, preferably at 100 g/l. Suitable conditions can be determined by the person skilled in the art by routine experiments.

Preferably the solution used for the crystallization contains compound of formula (I) in a purity of at least 85%, often at least 90%, in particular at least 95%, i.e. the content of organic impurities which are not organic solvents is not more than 15 wt. %, often not more than 10 wt. %, and in particular not more than 5 wt. %, based on the compound of formula (I) present dissolved in the solvent.

The solution used for the crystallization is preferably essentially free from solvents other than those stated. In this context, "essentially free" means that the concentration of other solvents in the compound of formula (I)-containing solution does not exceed 10 wt. %, often 5 wt. %, based on the total quantity of solvent.

The crystallization of form A of compound of formula (I) can be effected as follows, for example
- by cooling of the solution which contains the dissolved compound of formula (I),
- by allow the solution, which contains the dissolved compound of formula (I), to stand for some time at room temperature,
- by addition of a solubility-decreasing solvent to the solution which contains the dissolved compound of formula (I), in particular by addition of a nonpolar organic solvent or by addition of water,
- by concentration of the solution which contains the dissolved compound of formula (I),
- by stirring of a suspension of compound of formula (I) and preferably seeding with the form A of compound of formula (I), or
- by a combination of the aforesaid measures.

The crystallization of form A of compound of formula (I) is preferably effected by stirring of a suspension of compound of formula (I).

The crystallization is as a rule carried out until at least 80 wt. %, preferably at least 90 wt. %, of the compound of formula (I) used crystallizes out.

If the crystallization of form A is effected by cooling, the cooling rate is preferably less than 10 K/min.

The crystallization of form A can be promoted or accelerated by seeding with seed crystals of form A, for example by adding seed crystals of form A before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved compound of formula (I).

If the crystallization is performed in the presence of seed crystals of form A, these are preferably only added at a temperature at which the saturation concentration of the compound of formula (I) in the solvent in question has been reached, i.e. at or below that temperature at which the dissolved quantity of compound of formula (I) forms a saturated solution in the solvent in question. The person skilled in the art can determine the temperature dependence of the saturation concentration in a solvent in routine experiments.

Alternatively, the crystallization can also be effected by addition of a "non-solvent" (i.e. a solubility decreasing solvent) e.g. by addition of a nonpolar solvent or by addition of water, for example from 5 to 60 vol. %, in particular 20 to 55 vol. % and especially from 30 to 50 vol. %, based on the volume of the polar organic solvent or solvent mixture used for dissolution of the compound of formula (I). The addition of the nonpolar solvent or the addition of water are preferably effected over a prolonged period, for example over a period from 10 mins to 3 hrs, in particular over a period from 20 mins to 2.5 hrs. If the crystallization of form A is effected by the addition of a "non-solvent", the addition of the non-solvent is preferably at a slow rate, e.g. less than 10% v/v per minute, based on the volume of the compound of formula (I) solution. Often the addition will be done in such a manner that the nonpolar solvent or water is added until the discernable onset of the crystallization and the mixture thus obtained is then left for a time, during which the crystallization of the form A proceeds. If necessary, the mixture can then be cooled for completion of the crystallization.

In particular, the addition of the nonpolar solvent or the addition of water and the addition of seed crystals can be combined.

The addition of the nonpolar solvent can be effected in the form of a pure nonpolar solvent or in the form of a mixture of a nonpolar solvent with a solvent used for the dissolution. Examples of nonpolar solvents are aliphatic and cycloaliphatic hydrocarbons with preferably 5 to 10 C atoms such as pentane, hexane, cyclopentane, cyclohexane, isohexane, heptane, cycloheptane, octane, decane or mixtures thereof.

The isolation of the form A from the crystallization product, i.e. the separation of the form A from the mother liquor, is effected by usual techniques for the separation of solid components from liquids, for example by filtration, centrifugation or by decantation. As a rule, the isolated solid will be washed, for example with the solvent used for the crystallization, with water or with a mixture of the organic solvent used for the crystallization with water. The washing can be effected in one or more steps, washing with water often being used in the last washing step. The washing is typically effected at temperatures below 30° C., often below 25° C. and in particular below 20° C., in order to keep the loss of valuable product as small as possible. Next, the form A obtained can be dried and then supplied for further processing. Often, however, the moist active substance obtained after washing, in particular an active substance moist with water, will be supplied directly for the further processing.

By means of the crystallization according to the invention, the form A is obtained with a compound of formula (I) content of as a rule at least 90 wt. %, often 94 wt. %, in particular at least 96 wt. %.

The content of form A, based on the total quantity of compound of formula (I), is typically at least 90% and often at least 95% or at least 96%.

A further object of the present invention relates to the crystalline form B of compound of formula (I). Also an object is a compound of formula (I) which at least 90 wt. %, in particular at least 95% consists of the crystalline form B.

The form B according to the invention can be identified by X-ray powder diffractometry on the basis of its diffraction diagram. Thus an X-ray powder diffraction diagram recorded using Cu-Kα radiation (1.54178 Å) at 25° C. shows at least 3, often at least 5, in particular at least 7, and especially all of the reflections quoted in the following table as ° 2θ values or as interplanar spacings d:

| ° 2θ |
| --- |
| 7.1 ± 0.2 |
| 9.4 ± 0.2 |
| 9.8 ± 0.2 |
| 11.6 ± 0.2 |
| 13.6 ± 0.2 |
| 13.9 ± 0.2 |
| 15.3 ± 0.2 |
| 18.3 ± 0.2 |
| 19.0 ± 0.2 |
| 20.0 ± 0.2 |
| 20.8 ± 0.2 |
| 21.6 ± 0.2 |
| 22.3 ± 0.2 |
| 24.5 ± 0.2 |
| 27.2 ± 0.2 |

Preferably, an X-ray powder diffraction diagram recorded using Cu-Kα radiation (1.54178 Å) at 25° C. shows the following reflections as ° 2θ values: 7.1±0.2, 11.6±0.2, 15.3±0.2, 18.3±0.2 and 21.6±0.2.

Form B displays a thermogram with a characteristic melting peak in the range from 80 to 100° C. The melting point, determined as the onset of the melting peak, typically lies at 84° C. The values quoted here relate to values determined by differential calorimetry (differential scanning calorimetry, DSC; heating rate 10° C./min).

The production of the form B of the compound of formula (I) according to the invention is effected by
   by crystallization from a solution of the compound of formula (I)
   by crystallization from a solution of the compound of formula (I) in a suitable organic solvent The solution of compound of formula (I) can for example be prepared by the following methods:
(1) Dissolution of the compound of formula (I), preferably in a form different from form B, in one of the solvents mentioned below, or
(2) Preparation of the compound of formula (I) by a chemical reaction and transfer of the reaction mixture, if necessary after removal of reagents and/or side products, into an organic solvent suitable according to the invention.

For the preparation of the solution by dissolution of the compound of formula (I), essentially any known form of compound of formula (I) can be used. Often amorphous compound of formula (I) or a mixture of different crystalline modifications or a mixture of amorphous and crystalline compound of formula (I) will be used. Also suitable are crystalline forms of compound of formula (I) and mixtures thereof, for example the form A according to the invention, the form C described below, and also the form D described below and mixtures of these forms.

The dissolution of the compound of formula (I) is usually effected at room temperature. In one embodiment of the invention, the dissolution of the compound of formula (I) is effected at elevated temperature, and naturally the temperature used for dissolution will not exceed the boiling point of the solvent.

The solution of the compound of formula (I) can also be prepared by transferring a reaction mixture obtained by a chemical reaction, which contains the compound of formula (I), if necessary after removal of reagents and/or side products, into an organic solvent suitable according to the invention. This can be effected in such a manner that the reaction is performed in an organic solvent or solvent mixture which consists at least partly, preferably at least 50 wt. %, of a solvent suitable for the crystallization and, if necessary a workup is performed during which excess reagents and any catalysts present and any unsuitable solvents present, for example water and/or methanol, are removed. The preparation of a solution of the compound of formula (I) by chemical reaction of a suitable precursor of compound of formula (I) can be effected by analogy to the methods which are described in the state of the art cited at the beginning, to which full reference is hereby made.

The production of the form B of the compound of formula (I) according to the invention is effected by crystallization from a solution of the compound of formula (I) in a suitable organic solvent.

Suitable solvents for the crystallization of form B are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; alcohols such as methanol, ethanol, n-propanol, isopropanol, n-butanol and tert.-butanol, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP), water, and mixtures of the afore-mentioned solvents.

Preferred solvents are aliphatic hydrocarbons, ethers and alcohols as described above, more preferred alcohols.

In order to obtain form B of the compound of formula (I), the crystallization is preferably effected at room temperature.

Crystallization of form B is preferably effected under controlled conditions, i.e. the conditions of the crystallization are chosen to achieve a slow crystallization rate.

For this, in a first step i) a solution of the compound of formula (I) in one of the aforesaid organic solvents is prepared, and then in a second step ii) crystallization of the compound of formula (I) is effected.

The concentration of compound of formula (I) in the solution used for the crystallization of form B naturally depends on the nature of the solvent, the solution temperature and the form of the solved compound of formula (I) (i.e. amorphous or crystalline), and often lies in the range from 5 to 1500 g/l, preferably at 500 to 1500 g/l, especially preferred at 500 to 1500 g/l, more preferred at 1000 to 1200 g/l. Suitable conditions can be determined by the person skilled in the art by routine experiments.

Preferably the solution used for the crystallization contains compound of formula (I) in a purity of at least 85%, often at least 90%, in particular at least 95%, i.e. the content of organic impurities which are not organic solvents is not more than 15 wt. %, often not more than 10 wt. %, and in particular not more than 5 wt. %, based on the compound of formula (I) present dissolved in the solvent.

The solution used for the crystallization is preferably essentially free from solvents other than those stated. In this context, "essentially free" means that the concentration of other solvents in the compound of formula (I)-containing solution does not exceed 10 wt. %, often 5 wt. %, based on the total quantity of solvent.

The crystallization of form B of compound of formula (I) can be effected as follows, for example
   by cooling of the solution which contains the dissolved compound of formula (I),
   by allow the solution, which contains the dissolved compound of formula (I), to stand for some time at room temperature,
   by addition of a solubility-decreasing solvent to the solution which contains the dissolved compound of formula (I), in particular by addition of a nonpolar organic solvent or by addition of water,
   by concentration of the solution which contains the dissolved compound of formula (I),
   by stirring of a suspension of compound of formula (I) and preferably seeding with the form B of compound of formula (I), or
   by a combination of the aforesaid measures.

The crystallization of form B of compound of formula (I) is preferably effected by stirring of a suspension of compound of formula (I).

The crystallization is as a rule carried out until at least 80 wt. %, preferably at least 90 wt. %, of the compound of formula (I) used crystallizes out.

If the crystallization of form B is effected by cooling, the cooling rate is preferably less than 10 K/min.

The crystallization of form B can be promoted or accelerated by seeding with seed crystals of form B, for example by adding seed crystals of form B before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved compound of formula (I).

If the crystallization is performed in the presence of seed crystals of form B, these are preferably only added at a temperature at which the saturation concentration of the compound of formula (I) in the solvent in question has been reached, i.e. at or below that temperature at which the dissolved quantity of compound of formula (I) forms a saturated solution in the solvent in question. The person skilled in the art can determine the temperature dependence of the saturation concentration in a solvent in routine experiments.

Alternatively, the crystallization can also be effected by addition of a "non-solvent" (i.e. a solubility decreasing solvent) e.g. by addition of a nonpolar solvent or by addition of water, for example from 5 to 60 vol. %, in particular 20 to 55 vol. % and especially from 30 to 50 vol. %, based on the volume of the polar organic solvent or solvent mixture used for dissolution of the compound of formula (I). The addition of the nonpolar solvent or the addition of water are preferably effected over a prolonged period, for example over a period from 10 mins to 3 hrs, in particular over a period from 20 mins to 2.5 hrs. If the crystallization of form B is effected by the addition of a "non-solvent", the addition of the non-solvent is preferably at a slow rate, e.g. less than 10% v/v per minute, based on the volume of the compound of formula (I) solution. Often the addition will be done in such a manner that the nonpolar solvent or water is added until the discernable onset of the crystallization and the mixture thus obtained is then left for a time, during which the crystallization of the form B proceeds. If necessary, the mixture can then be cooled for completion of the crystallization.

In particular, the addition of the nonpolar solvent or the addition of water and the addition of seed crystals can be combined.

The addition of the nonpolar solvent can be effected in the form of a pure nonpolar solvent or in the form of a mixture of a nonpolar solvent with a solvent used for the dissolution. Examples of nonpolar solvents are aliphatic and cycloaliphatic hydrocarbons with preferably 5 to 10 C atoms such as pentane, hexane, cyclopentane, cyclohexane, isohexane, heptane, cycloheptane, octane, decane or mixtures thereof.

The isolation of the form B from the crystallization product, i.e. the separation of the form B from the mother liquor, is effected by usual techniques for the separation of solid components from liquids, for example by filtration, centrifugation or by decantation. As a rule, the isolated solid will be washed, for example with the solvent used for the crystallization, with water or with a mixture of the organic solvent used for the crystallization with water. The washing can be effected in one or more steps, washing with water often being used in the last washing step. The washing is typically effected at temperatures below 30° C., often below 25° C. and in particular below 20° C., in order to keep the loss of valuable product as small as possible. Next, the form B obtained can be dried and then supplied for further processing. Often, however, the moist active substance obtained after washing, in particular an active substance moist with water, will be supplied directly for the further processing.

By means of the crystallization according to the invention, the form B is obtained with a compound of formula (I) content of as a rule at least 90 wt. %, often 94 wt. %, in particular at least 96 wt. %.

The content of form B, based on the total quantity of compound of formula (I), is typically at least 90% and often at least 95% or at least 96%.

A further object of the present invention relates to the crystalline form C of compound of formula (I). Also an object is a compound of formula (I) which at least 90 wt. %, in particular at least 95% consists of the crystalline form C.

The form C according to the invention can be identified by X-ray powder diffractometry on the basis of its diffraction diagram. Thus, an X-ray powder diffraction diagram recorded using Cu-Kα radiation (1.54178 Å) at 25° C. shows at least 3, often at least 5, in particular at least 7, and especially all of the reflections quoted in the following table as ° 2θ values or as interplanar spacings d:

| ° 2θ |
| --- |
| 10.6 ± 0.2 |
| 12.3 ± 0.2 |
| 15.3 ± 0.2 |
| 15.8 ± 0.2 |
| 18.3 ± 0.2 |
| 18.6 ± 0.2 |
| 19.2 ± 0.2 |
| 19.9 ± 0.2 |
| 20.6 ± 0.2 |
| 21.8 ± 0.2 |
| 22.6 ± 0.2 |
| 24.5 ± 0.2 |
| 25.5 ± 0.2 |
| 26.0 ± 0.2 |
| 27.0 ± 0.2 |
| 28.3 ± 0.2 |

Preferably, an X-ray powder diffraction diagram recorded using Cu-Kα radiation (1.54178 Å) at 25° C. shows the following reflections as ° 2θ values: 15.3±0.2, 15.8±0.2, 18.3±0.2 21.8±0.2 and 22.6±0.2.

Studies on single crystals of form C demonstrate that the underlying crystal structure is monoclinic. The unit cell has the space group $P2_1/c$. The characteristic data of the crystal structure of form C (determined at 100 K) are compiled in the following table:

Crystallographic Characteristics of Form C

| Parameter | Form C |
| --- | --- |
| class | monoclinic |
| space group | $P2_1/c$ |
| a | 14.3338(7) Å |
| b | 9.0069(4) Å |
| c | 16.6765(8) Å |
| α | 90° |
| β | 93.343(2)° |
| γ | 90° |
| volume | 2149.32(18) Å$^3$ |
| Z | 4 |

-continued

| Parameter | Form C |
|---|---|
| density (calculated) | 1.603 g/cm³ |
| wavelength | 1.54178 Å | a, b, c = unit cell length
α, β, Υ = unit cell angle
Z = number of molecules in the unit cell Form C displays a thermogram with a characteristic melting peak in the range from 80 to 105° C. The melting point, determined as the onset of the melting peak, typically lies at 87° C. The values quoted here relate to values determined by differential calorimetry (differential scanning calorimetry, DSC; heating rate 10° C./min).

The production of the form C of the compound of formula (I) according to the invention is effected by
  by crystallization from a solution of the compound of formula (I)
  by crystallization from a solution of the compound of formula (I) in a suitable organic solvent The solution of compound of formula (I) can for example be prepared by the following methods:
(1) Dissolution of the compound of formula (I), preferably in a form different from form C, in one of the solvents mentioned below, or
(2) Preparation of the compound of formula (I) by a chemical reaction and transfer of the reaction mixture, if necessary after removal of reagents and/or side products, into an organic solvent suitable according to the invention.

For the preparation of the solution by dissolution of the compound of formula (I), essentially any known form of compound of formula (I) can be used. Often amorphous compound of formula (I) or a mixture of different crystalline modifications or a mixture of amorphous and crystalline compound of formula (I) will be used. Also suitable are crystalline forms of compound of formula (I) and mixtures thereof, for example the form A and B according to the invention, and also the form D described below and mixtures of these forms.

The dissolution of the compound of formula (I) is usually effected at temperatures in the range from room temperature to 75° C. In one embodiment of the invention, the dissolution of the compound of formula (I) is effected at elevated temperature, in particular at 75° C., and naturally the temperature used for dissolution will not exceed the boiling point of the solvent.

The solution of the compound of formula (I) can also be prepared by transferring a reaction mixture obtained by a chemical reaction, which contains the compound of formula (I), if necessary after removal of reagents and/or side products, into an organic solvent suitable according to the invention. This can be effected in such a manner that the reaction is performed in an organic solvent or solvent mixture which consists at least partly, preferably at least 50 wt. %, of a solvent suitable for the crystallization and, if necessary a workup is performed during which excess reagents and any catalysts present and any unsuitable solvents present, for example water and/or methanol, are removed. The preparation of a solution of the compound of formula (I) by chemical reaction of a suitable precursor of compound of formula (I) can be effected by analogy to the methods which are described in the state of the art cited at the beginning, to which full reference is hereby made.

The production of the form C of the compound of formula (I) according to the invention is effected by crystallization from a solution of the compound of formula (I) in a suitable organic solvent.

Suitable solvents for the crystallization of form C are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; alcohols such as methanol, ethanol, n-propanol, isopropanol, n-butanol and tert.-butanol, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP), water, and mixtures of the afore-mentioned solvents.

Preferred solvents are aliphatic hydrocarbons, aromatic hydrocarbons, esters, ketones and alcohols as described above, more preferred alcohols.

In order to obtain form C of the compound of formula (I), the crystallization is preferably effected from 75° C. to room temperature, in particular at room temperature. Crystallization of form C is preferably effected under controlled conditions, i.e. the conditions of the crystallization are chosen to achieve a slow crystallization rate.

For this, in a first step i) a solution of the compound of formula (I) in one of the aforesaid organic solvents is prepared, and then in a second step ii) crystallization of the compound of formula (I) is effected.

The concentration of compound of formula (I) in the solution used for the crystallization of form C naturally depends on the nature of the solvent, the solution temperature and the form of the solved compound of formula (I) (i.e. amorphous or crystalline), and often lies in the range from 5 to 1500 g/l, preferably from 5 to 500 g/l, especially preferred from 5 to 150 g/l. Suitable conditions can be determined by the person skilled in the art by routine experiments.

Preferably the solution used for the crystallization contains compound of formula (I) in a purity of at least 85%, often at least 90%, in particular at least 95%, i.e. the content of organic impurities which are not organic solvents is not more than 15 wt. %, often not more than 10 wt. %, and in particular not more than 5 wt. %, based on the compound of formula (I) present dissolved in the solvent.

The solution used for the crystallization is preferably essentially free from solvents other than those stated. In this context, "essentially free" means that the concentration of other solvents in the compound of formula (I)-containing solution does not exceed 10 wt. %, often 5 wt. %, based on the total quantity of solvent.

The crystallization of form C of compound of formula (I) can be effected as follows, for example
  by cooling of the solution which contains the dissolved compound of formula (I),
  by allow the solution, which contains the dissolved compound of formula (I), to stand for some time at room temperature,
  by addition of a solubility-decreasing solvent to the solution which contains the dissolved compound of formula (I), in particular by addition of a nonpolar organic solvent or by addition of water, by concentration of the solution which contains the dissolved compound of formula (I), by stirring of a suspension of compound of formula (I) and preferably seeding with the form A of compound of formula (I), or by a combination of the aforesaid measures.

The crystallization of form C of compound of formula (I) is preferably effected by cooling of the solution which contains the dissolved compound of formula (I), by concentration of the solution which contains the dissolved compound of formula (I) and/or by stirring of a suspension of compound of formula (I).

The crystallization is as a rule carried out until at least 80 wt. %, preferably at least 90 wt. %, of the compound of formula (I) used crystallizes out.

If the crystallization of form C is effected by cooling, the cooling rate is preferably less than 10 K/min.

The crystallization of form C can be promoted or accelerated by seeding with seed crystals of form C, for example by adding seed crystals of form C before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved compound of formula (I).

If the crystallization is performed in the presence of seed crystals of form C, these are preferably only added at a temperature at which the saturation concentration of the compound of formula (I) in the solvent in question has been reached, i.e. at or below that temperature at which the dissolved quantity of compound of formula (I) forms a saturated solution in the solvent in question. The person skilled in the art can determine the temperature dependence of the saturation concentration in a solvent in routine experiments.

Alternatively, the crystallization can also be effected by addition of a "non-solvent" (i.e. a solubility decreasing solvent) e.g. by addition of a nonpolar solvent or by addition of water, for example from 5 to 60 vol. %, in particular 20 to 55 vol. % and especially from 30 to 50 vol. %, based on the volume of the polar organic solvent or solvent mixture used for dissolution of the compound of formula (I). The addition of the nonpolar solvent or the addition of water are preferably effected over a prolonged period, for example over a period from 10 mins to 3 hrs, in particular over a period from 20 mins to 2.5 hrs. If the crystallization of form C is effected by the addition of a "non-solvent", the addition of the non-solvent is preferably at a slow rate, e.g. less than 10% v/v per minute, based on the volume of the compound of formula (I) solution. Often the addition will be done in such a manner that the nonpolar solvent or water is added until the discernable onset of the crystallization and the mixture thus obtained is then left for a time, during which the crystallization of the form C proceeds. If necessary, the mixture can then be cooled for completion of the crystallization.

In particular, the addition of the nonpolar solvent or the addition of water and the addition of seed crystals can be combined.

The addition of the nonpolar solvent can be effected in the form of a pure nonpolar solvent or in the form of a mixture of a nonpolar solvent with a solvent used for the dissolution. Examples of nonpolar solvents are aliphatic and cycloaliphatic hydrocarbons with preferably 5 to 10 C atoms such as pentane, hexane, cyclopentane, cyclohexane, isohexane, heptane, cycloheptane, octane, decane or mixtures thereof.

The isolation of the form C from the crystallization product, i.e. the separation of the form C from the mother liquor, is effected by usual techniques for the separation of solid components from liquids, for example by filtration, centrifugation or by decantation. As a rule, the isolated solid will be washed, for example with the solvent used for the crystallization, with water or with a mixture of the organic solvent used for the crystallization with water. The washing can be effected in one or more steps, washing with water often being used in the last washing step. The washing is typically effected at temperatures below 30° C., often below 25° C. and in particular below 20° C., in order to keep the loss of valuable product as small as possible. Next, the form C obtained can be dried and then supplied for further processing. Often, however, the moist active substance obtained after washing, in particular an active substance moist with water, will be supplied directly for the further processing.

By means of the crystallization according to the invention, the form C is obtained with a compound of formula (I) content of as a rule at least 90 wt. %, often 94 wt. %, in particular at least 96 wt. %.

The content of form C, based on the total quantity of compound of formula (I), is typically at least 90% and often at least 95% or at least 96%.

A further object of the present invention relates to the crystalline form D of compound of formula (I). Also an object is a compound of formula (I) which at least 90 wt. %, in particular at least 95% consists of the crystalline form D.

The form D according to the invention can be identified by X-ray powder diffractometry on the basis of its diffraction diagram. Thus an X-ray powder diffraction diagram recorded using Cu-Kα radiation (1.54178 Å) at 25° C. shows at least 3, often at least 5, in particular at least 7, and especially all of the reflections quoted in the following table as ° 2θ values or as interplanar spacings d:

| ° 2θ |
| --- |
| 5.2 ± 0.2 |
| 6.9 ± 0.2 |
| 10.4 ± 0.2 |
| 14.7 ± 0.2 |
| 18.9 ± 0.2 |
| 20.1 ± 0.2 |
| 21.6 ± 0.2 |
| 22.1 ± 0.2 |
| 23.0 ± 0.2 |
| 24.7 ± 0.2 |

Preferably, an X-ray powder diffraction diagram recorded using Cu-Kα radiation (1.54178 Å) at 25° C. shows the following reflections as ° 2θ values: 5.2±0.2, 6.9±0.2, 10.4±0.2, 20.1±0.2 and 24.7±0.2.

Studies on single crystals of form D demonstrate that the underlying crystal structure is monoclinic. The unit cell has the space group P2$_1$/c. The characteristic data of the crystal structure of form C (determined at 100 K) are compiled in the following table:

Crystallographic Characteristics of Form D

| Parameter | Form D |
| --- | --- |
| class | monoclinic |
| space group | P2$_1$/c |
| a | 18.144(2) Å |
| b | 9.5408(11) Å |

-continued

| Parameter | Form D |
|---|---|
| c | 25.953(3) Å |
| α | 90° |
| β | 106.923(6)° |
| Y | 90° |
| volume | 4298.2(9) Å³ |
| Z | 8 |
| density (calculated) | 1.603 g/cm³ |
| wavelength | 1.54178 Å | a, b, c = unit cell length
α, β, Y = unit cell angle
Z = number of molecules in the unit cell Form D displays a thermogram with a characteristic melting peak in the range from 55 to 80° C. The melting point, determined as the onset of the melting peak, typically lies at 67° C. The values quoted here relate to values determined by differential calorimetry (differential scanning calorimetry, DSC; heating rate 10° C./min).

The production of the form D of the compound of formula (I) according to the invention is effected by
  by crystallization from a solution of the compound of formula (I)
  by crystallization from a solution of the compound of formula (I) in a suitable organic solvent The solution of compound of formula (I) can for example be prepared by the following methods:
(1) Dissolution of the compound of formula (I), preferably in a form different from form D, in one of the solvents mentioned below, or
(2) Preparation of the compound of formula (I) by a chemical reaction and transfer of the reaction mixture, if necessary after removal of reagents and/or side products, into an organic solvent suitable according to the invention.

For the preparation of the solution by dissolution of the compound of formula (I), essentially any known form of compound of formula (I) can be used. Often amorphous compound of formula (I) or a mixture of different crystalline modifications or a mixture of amorphous and crystalline compound of formula (I) will be used. Also suitable are crystalline forms of compound of formula (I) and mixtures thereof, for example the forms A, B and C according to the invention, and also mixtures of these forms.

The dissolution of the compound of formula (I) is usually effected at room temperature. In one embodiment of the invention, the dissolution of the compound of formula (I) is effected at elevated temperature, and naturally the temperature used for dissolution will not exceed the boiling point of the solvent.

The solution of the compound of formula (I) can also be prepared by transferring a reaction mixture obtained by a chemical reaction, which contains the compound of formula (I), if necessary after removal of reagents and/or side products, into an organic solvent suitable according to the invention. This can be effected in such a manner that the reaction is performed in an organic solvent or solvent mixture which consists at least partly, preferably at least 50 wt. %, of a solvent suitable for the crystallization and, if necessary a workup is performed during which excess reagents and any catalysts present and any unsuitable solvents present, for example water and/or methanol, are removed. The preparation of a solution of the compound of formula (I) by chemical reaction of a suitable precursor of compound of formula (I) can be effected by analogy to the methods which are described in the state of the art cited at the beginning, to which full reference is hereby made.

The production of the form D of the compound of formula (I) according to the invention is effected by crystallization from a solution of the compound of formula (I) in a suitable organic solvent.

Suitable solvents for the crystallization of form D are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; alcohols such as methanol, ethanol, n-propanol, isopropanol, n-butanol and tert.-butanol, as well as dipolar aprotic solvents such as sulfolane, dimethylsulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP), water, and mixtures of the afore-mentioned solvents.

Preferred solvents are aliphatic hydrocarbons, aromatic hydrocarbons and alcohols as described above, more preferred alcohols.

In order to obtain form D of the compound of formula (I), the crystallization is preferably effected room temperature.

Crystallization of form D is preferably effected under controlled conditions, i.e. the conditions of the crystallization are chosen to achieve a slow crystallization rate.

For this, in a first step i) a solution of the compound of formula (I) in one of the aforesaid organic solvents is prepared, and then in a second step ii) crystallization of the compound of formula (I) is effected.

The concentration of compound of formula (I) in the solution used for the crystallization of form D naturally depends on the nature of the solvent, the solution temperature and the form of the solved compound of formula (I) (i.e. amorphous or crystalline), and often lies in the range from 5 to 1500 g/l, preferably from 20 to 500 g/l, especially preferred from 25 to 160 g/l. Suitable conditions can be determined by the person skilled in the art by routine experiments.

Preferably the solution used for the crystallization contains compound of formula (I) in a purity of at least 85%, often at least 90%, in particular at least 95%, i.e. the content of organic impurities which are not organic solvents is not more than 15 wt. %, often not more than 10 wt. %, and in particular not more than 5 wt. %, based on the compound of formula (I) present dissolved in the solvent.

The solution used for the crystallization is preferably essentially free from solvents other than those stated. In this context, "essentially free" means that the concentration of other solvents in the compound of formula (I)-containing solution does not exceed 10 wt. %, often 5 wt. %, based on the total quantity of solvent.

The crystallization of form D of compound of formula (I) can be effected as follows, for example
  by cooling of the solution which contains the dissolved compound of formula (I),
  by allow the solution, which contains the dissolved compound of formula (I), to stand for some time at room temperature,
  by addition of a solubility-decreasing solvent to the solution which contains the dissolved compound of formula (I), in particular by addition of a nonpolar organic solvent or by addition of water, by concentration of the solution which contains the dissolved compound of formula (I), by stirring of a suspension of compound of formula (I) and preferably seeding with the form A of compound of formula (I), or by a combination of the aforesaid measures.

The crystallization of form D of compound of formula (I) is preferably effected by concentration of the solution which contains the dissolved compound of formula (I) and/or by stirring of a suspension of compound of formula (I).

The crystallization is as a rule carried out until at least 80 wt. %, preferably at least 90 wt. %, of the compound of formula (I) used crystallizes out.

If the crystallization of form D is effected by cooling, the cooling rate is preferably less than 10 K/min.

The crystallization of form D can be promoted or accelerated by seeding with seed crystals of form D, for example by adding seed crystals of form D before or during the crystallization.

If seed crystals are added during the crystallization, the quantity thereof is typically 0.001 to 10 wt. %, often 0.005 to 5 wt. %, in particular 0.01 to 1 wt. % and especially 0.05 to 0.5 wt. %, based on the dissolved compound of formula (I).

If the crystallization is performed in the presence of seed crystals of form D, these are preferably only added at a temperature at which the saturation concentration of the compound of formula (I) in the solvent in question has been reached, i.e. at or below that temperature at which the dissolved quantity of compound of formula (I) forms a saturated solution in the solvent in question. The person skilled in the art can determine the temperature dependence of the saturation concentration in a solvent in routine experiments.

Alternatively, the crystallization can also be effected by addition of a "non-solvent" (i.e. a solubility decreasing solvent) e.g. by addition of a nonpolar solvent or by addition of water, for example from 5 to 60 vol. %, in particular 20 to 55 vol. % and especially from 30 to 50 vol. %, based on the volume of the polar organic solvent or solvent mixture used for dissolution of the compound of formula (I). The addition of the nonpolar solvent or the addition of water are preferably effected over a prolonged period, for example over a period from 10 mins to 3 hrs, in particular over a period from 20 mins to 2.5 hrs. If the crystallization of form D is effected by the addition of a "non-solvent", the addition of the non-solvent is preferably at a slow rate, e.g. less than 10% v/v per minute, based on the volume of the compound of formula (I) solution. Often the addition will be done in such a manner that the nonpolar solvent or water is added until the discernable onset of the crystallization and the mixture thus obtained is then left for a time, during which the crystallization of the form D proceeds. If necessary, the mixture can then be cooled for completion of the crystallization.

In particular, the addition of the nonpolar solvent or the addition of water and the addition of seed crystals can be combined.

The addition of the nonpolar solvent can be effected in the form of a pure nonpolar solvent or in the form of a mixture of a nonpolar solvent with a solvent used for the dissolution. Examples of nonpolar solvents are aliphatic and cycloaliphatic hydrocarbons with preferably 5 to 10 C atoms such as pentane, hexane, cyclopentane, cyclohexane, isohexane, heptane, cycloheptane, octane, decane or mixtures thereof.

The isolation of the form D from the crystallization product, i.e. the separation of the form D from the mother liquor, is effected by usual techniques for the separation of solid components from liquids, for example by filtration, centrifugation or by decantation. As a rule, the isolated solid will be washed, for example with the solvent used for the crystallization, with water or with a mixture of the organic solvent used for the crystallization with water. The washing can be effected in one or more steps, washing with water often being used in the last washing step. The washing is typically effected at temperatures below 30° C., often below 25° C. and in particular below 20° C., in order to keep the loss of valuable product as small as possible. Next, the form D obtained can be dried and then supplied for further processing. Often, however, the moist active substance obtained after washing, in particular an active substance moist with water, will be supplied directly for the further processing.

By means of the crystallization according to the invention, the form D is obtained with a compound of formula (I) content of as a rule at least 90 wt. %, often 94 wt. %, in particular at least 96 wt. %.

The content of form D, based on the total quantity of compound of formula (I), is typically at least 90% and often at least 95% or at least 96%.

The forms A, B, C and/or D, preferably form C, of compound of formula (I) are suitable as herbicides.

The invention thus also relates to plant protection agents containing the forms A, B, C and/or D, preferably form C and additives usual for the formulation of plant protection agents, in particular plant protection agents in the form of aqueous suspension concentrates (so-called SC's) or non-aqueous suspension concentrates (so-called OD's), and plant protection agents in the form of powders (so-called WP's) and granules (so-called WG's) dispersible in water. The invention also relates to a process for combating undesired plant growth, which is characterized in that the forms A, B, C and/or D, preferably form C, of compound of formula (I), preferably as a suitable active substance preparation, is used on plants, their habitat and/or on seeds.

The plant protection agents which contain compound of formula (I) in the forms A, B, C and/or D, preferably form C, combat plant growth, in particular monocotyledonous weed species such as *Avena, Lolium, Alopecurus, Phalaris, Echinochloa, Digitaria, Setaria, Cyperus* species, *Agropyron, Cynodon, Imparato* and *Sorghum*, and dicotyledonous weed species such as Galium, Viola, Veronica, *Lamium, Stellaria, Amaranthus, Sinapsis, Ipomoea, Matricaria, Abutilon, Sida, Convolvulus, Cirsium, Rumex* and *Artemisia* on non-cultivated areas very well, particularly at high application levels.

Depending on the particular application method, the forms A, B, C and/or D, preferably form C, of compound of formula (I) or the plant protection agents containing them can also be used in a further number of crop plants for the elimination of undesired plants.

Examples of suitable crops are the following:
*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium* herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N. rustica), Olea europaea, Oryza sativa, Phaseolus lunatus, Phaseolus vulgaris, Picea abies, Pinus spec., Pistacia vera, Pisum sativum, Prunus avium, Prunus persica, Pyrus communis, Prunus armeniaca, Prunus cerasus, Prunus dulcis and Prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera and Zea mays.

Preferred crops are Arachis hypogaea, Beta vulgaris spec. altissima, Brassica napus var. napus, Brassica oleracea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus spec., Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (S. vulgare), Triticale, Triticum aestivum, Triticum durum, Vicia faba, Vitis vinifera and Zea mays.

Especially preferred crops are crops of cereals, corn, soybeans, rice, oilseed rape, cotton, potatoes, peanuts or permanent crops.

The forms A, B, C and/or D, preferably form C, of compound of formula (I) according to the invention, or the agrochemical compositions and/or herbicidal compositions comprising the aforementioned forms, can also be used in crops which have been modified by mutagenesis or genetic engineering in order to provide a new trait to a plant or to modify an already present trait.

The term "crops" as used herein includes also (crop) plants which have been modified by mutagenesis or genetic engineering in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include in particular herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by conventional methods of mutagenesis and breeding comprise plant varieties commercially available under the name Clearfield®. However, most of the herbicide tolerance traits have been created via the use of transgenes.

Herbicide tolerance has been created to glyphosate, glufosinate, 2,4-D, dicamba, oxynil herbicides, like bromoxynil and ioxynil, sulfonylurea herbicides, ALS inhibitor herbicides and 4-hydroxyphenylpyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621 and goxv247, for tolerance to glufosinate: pat and bar, for tolerance to 2,4-D: aad-1 and aad-12, for tolerance to dicamba: dmo, for tolerance to oxynil herbicies: bxn, for tolerance to sulfonylurea herbicides: zm-hra, csr1-2, gm-hra, S4-HrA, for tolerance to ALS inhibitor herbicides: csr1-2, for tolerance to HPPD inhibitor herbicides: hppdPF, W336 and avhppd-03.

Transgenic corn events comprising herbicide tolerance genes are for example, but not excluding others, DAS40278, MON801, MON802, MON809, MON810, MON832, MON87411, MON87419, MON87427, MON88017, MON89034, NK603, GA21, MZHGOJG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes are for example, but not excluding others, GTS 40-3-2, MON87705, MON87708, MON87712, MON87769, MON89788, A2704-12, A2704-21, A5547-127, A5547-35, DP356043, DAS44406-6, DAS68416-4, DAS-81419-2, GU262, SYHTØH2, W62, W98, FG72 and CV127.

Transgenic cotton events comprising herbicide tolerance genes are for example, but not excluding others, 19-51a, 31707, 42317, 81910, 281-24-236, 3006-210-23, BXN10211, BXN10215, BXN10222, BXN10224, MON1445, MON1698, MON88701, MON88913, GHB119, GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants. Transgenes which have most frequently been used are toxin genes of Bacillus spec. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin have been transferred to other plants. In particular genes coding for protease inhibitors, like CpTI and pinII. A further approach uses transgenes in order to produce double stranded RNA in plants to target and down-regulate insect genes. An example for such a transgene is dvsnf7.

Transgenic corn events comprising genes for insecticidal proteins or double stranded RNA are for example, but not excluding others, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098.

Transgenic soybean events comprising genes for insecticidal proteins are for example, but not excluding others, MON87701, MON87751 and DAS-81419.

Transgenic cotton events comprising genes for insecticidal proteins are for example, but not excluding others, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by increasing ear biomass using the transgene athb17, being present in corn event MON87403, or by enhancing photosynthesis using the transgene bbx32, being present in the soybean event MON87712.

Crops comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, in particular to tolerance to drought, has been created by using the transgene cspB, comprised by the corn event MON87460 and by using the transgene Hahb-4, comprised by soybean event IND-ØØ41Ø-5.

Traits are frequently combined by combining genes in a transformation event or by combining different events during the breeding process. Preferred combination of traits are herbicide tolerance to different groups of herbicides, insect tolerance to different kind of insects, in particular tolerance to lepidopteran and coleopteran insects, herbicide tolerance with one or several types of insect resistance, herbicide tolerance with increased yield as well as a combination of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agri-biotech Applications (ISAAA)" (http://www.isaaa.org/gmapprovaldatabase) and the "Center for Environmental Risk Assessment (CERA)" (http://cera-gmc.org/GMCropDatabase), as well as in patent applications, like EP3028573 and WO2017/011288.

The use of compositions according to the invention on crops may result in effects which are specific to a crop comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, *mycoplasma*, viral or viroid pathogens as well as early vigour, early or delayed ripening, cold or heat tolerance as well as changed amino acid or fatty acid spectrum or content.

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

The forms A, B, C and/or D, preferably form C, of compound of formula (I) are also just as suitable as the known amorphous compound of formula (I) for the defoliation and desiccation of plant parts, for example for crop plants such as cotton, potato, rape, sunflower, soya bean or field beans, in particular cotton.

In this regard, embodiments of the invention also relate to agents for the desiccation and/or defoliation of plants, processes for the production of these agents and methods for the desiccation and/or defoliation of plants using the forms A, B, C and/or D, preferably form C, of the compound of formula (I).

The forms A, B, C and/or D, preferably form C, of the compound of formula (I) are in particular suitable as desiccants for the desiccation of the aboveground parts of crop plants such as potato, oilseed rape, sunflower and soya bean, but also cereals. This enables completely mechanical harvesting of these important crop plants.

Also of scientific interest is the facilitation of harvesting which is enabled by the time-concentrated dropping or reduction of the strength of attachment to the tree with citrus fruits, olives or other species and varieties of pomaceous, stone and shelled fruit. The same mechanism, i.e. the promotion of the formation of separation tissue between fruit or leaf and shoot of the plants is also significant for well-controlled defoliation of useful plants, in particular cotton.

In addition, the shortening of the time interval in which the individual cotton plants become ripe leads to heightened fiber quality after the harvest.

To widen the spectrum of action and to achieve synergistic effects, the forms A, B, C and/or D, preferably form C, may be mixed with a large number of representatives of other herbicidal or growth-regulating active ingredient groups and then applied concomitantly. Suitable components for mixtures are, for example, herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

It may furthermore be beneficial to apply the forms A, B, C and/or D, preferably form C, alone or in combination with other herbicides, or else in the form of a mixture with other crop protection agents, for example together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

In one embodiment of the present invention the compositions according to the present invention comprise the forms A, B, C and/or D, (component A), preferably form C (component A), and at least one further active compound selected from herbicides B, preferably herbicides B of class b1) to b15), and safeners C (compound C, component C).

In another embodiment of the present invention the compositions according to the present invention comprise form the forms A, B, C and/or D, (component A), preferably form C (component A), and at least one further active compound B (herbicide B, component B).

The further herbicidal compound B (component B) is preferably selected from the herbicides of class b1) to b15):

B) herbicides of class b1) to b15):
- b1) lipid biosynthesis inhibitors;
- b2) acetolactate synthase inhibitors (ALS inhibitors);
- b3) photosynthesis inhibitors;
- b4) protoporphyrinogen-IX oxidase inhibitors,
- b5) bleacher herbicides;
- b6) enolpyruvyl shikimate 3-phosphate synthase inhibitors (EPSP inhibitors);
- b7) glutamine synthetase inhibitors;
- b8) 7,8-dihydropteroate synthase inhibitors (DHP inhibitors);
- b9) mitosis inhibitors;
- b10) inhibitors of the synthesis of very long chain fatty acids (VLCFA inhibitors);
- b11) cellulose biosynthesis inhibitors;
- b12) decoupler herbicides;
- b13) auxinic herbicides;
- b14) auxin transport inhibitors; and
- b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

including their agriculturally acceptable salts or derivatives.

Preference is given to those compositions according to the present invention comprising at least one herbicide B selected from herbicides of class b2, b3, b4, b5, b6, b7, b9, b10 and b13.

Specific preference is given to those compositions according to the present invention which comprise at least one herbicide B selected from the herbicides of class b4, b6, b7, b9, b10 and b13.

Particular preference is given to those compositions according to the present invention which comprise at least one herbicide B selected from the herbicides of class b4, b6, b10 and b13.

Examples of herbicides B which can be used in combination with the forms A, B, C and/or D, preferably form C, according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:
amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors: acifluorfen, acifluorfen-sodium, azafenidin, bencarbazone, benzfendizone, bifenox, butafenacil, carfentrazone, carfentrazone-ethyl, chlomethoxyfen, chlorphthalim, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoro-methylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)-pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:
chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napronalide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

II.1
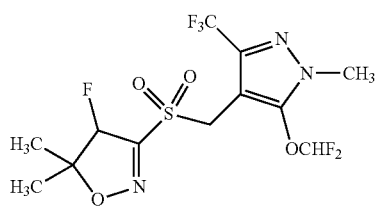

II.2
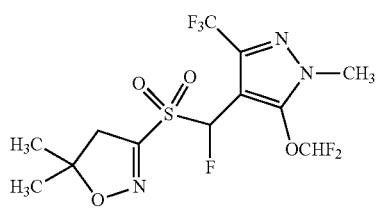

II.3
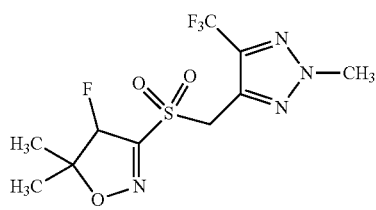

II.4
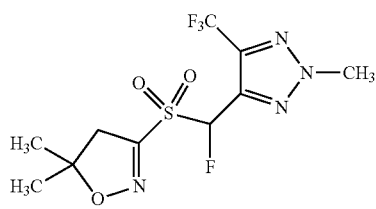

II.5
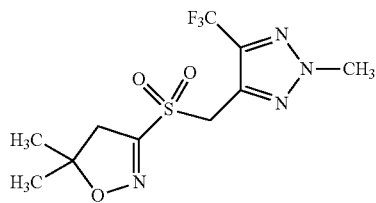

II.6
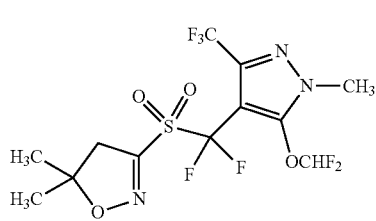

II.7
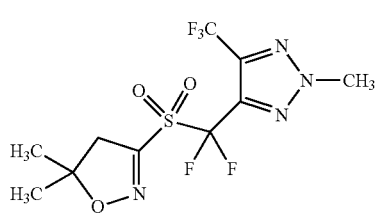

II.8
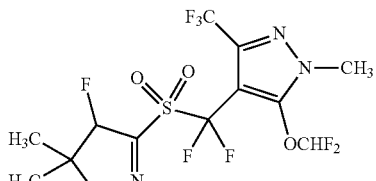

II.9
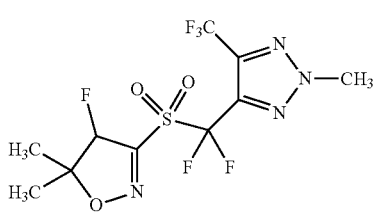

the isoxazoline compounds of the formula (II) are known in the art, e.g. from WO 2006/024820, WO 2006/037945, WO 2007/071900 and WO 2007/096576;
among the VLCFA inhibitors, preference is given to chloroacetamides and oxyacetamides;

b11) from the group of the cellulose biosynthesis inhibitors: chlorthiamid, dichlobenil, flupoxam, indaziflam, isoxaben, triaziflam and 1-cyclohexyl-5-pentafluorphenyloxy-14-[1,2,4,6]thiatriazin-3-ylamine (CAS 175899-01-1);

b12) from the group of the decoupler herbicides: dinoseb, dinoterb and DNOC and its salts;

b13) from the group of the auxinic herbicides: 2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA(2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preferred herbicides B that can be used in combination with the forms A, B, C and/or D, preferably form C, of the formula (I) according to the present invention are:

b1) from the group of the lipid biosynthesis inhibitors:
clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5 (4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:
amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:
ametryn, amicarbazone, atrazine, bentazone, bentazone-sodium, bromoxynil and its salts and esters, chloridazone, chlorotoluron, cyanazine, desmedipham, diquat-dibromide, diuron, fluometuron, hexazinone, ioxynil and its salts and esters, isoproturon, lenacil, linuron, metamitron, methabenzthiazuron, metribuzin, paraquat, paraquat-dichloride, phenmedipham, propanil, pyridate, simazine, terbutryn, terbuthylazine, thidiazuron, 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8) and 1-(5-tert-butylisoxazol-3-yl)-4-ethoxy-5-hydroxy-3-methyl-imidazolidin-2-one (CAS 1844836-64-1);

b4) from the group of the protoporphyrinogen-IX oxidase inhibitors:
acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen, pyraflufen-ethyl, saflufenacil, sulfentrazone, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoro-methylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1HL pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
aclonifen, amitrole, beflubutamid, benzobicyclon, bicyclopyrone, clomazone, diflufenican, fenquinotrione, flumeturon, flurochloridone, flurtamone, isoxaflutole, mesotrione, oxotrione (CAS 1486617-21-3), norflurazon, picolinafen, pyrasulfotole, pyrazolynate, sulcotrione, tefuryltrione, tembotrione, tolpyralate, topramezone, 4-(3-trifluoromethylphenoxy)-2-(4-trifluoromethylphenyl)pyrimidine (CAS180608-33-7), 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors:
glyphosate, glyphosate-isopropylammonium, glyphosate-potassium and glyphosate-trimesium (sulfosate);

b7) from the group of the glutamine synthase inhibitors: glufosinate, glufosinate-P, glufosinate-ammonium;

b8) from the group of the DHP synthase inhibitors: asulam;

b9) from the group of the mitosis inhibitors: benfluralin, dithiopyr, ethalfluralin, flamprop, flamprop-isopropyl, flamprop-methyl, flamprop-M-isopropyl, flamprop-M-methyl, oryzalin, pendimethalin, thiazopyr and trifluralin;

b10) from the group of the VLCFA inhibitors: acetochlor, alachlor, amidochlor, anilofos, butachlor, cafenstrole, dimethenamid, dimethenamid-P, fentrazamide, flufenacet, mefenacet, metazachlor, metolachlor, S-metolachlor, naproanilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, indaziflam, isoxaben, triaziflam and 1-cyclohexyl-5-pentafluorphenyloxy-14-[1,2,4,6]thiatri-azin-3-ylamine (CAS 175899-01-1);

b13) from the group of the auxinic herbicides:
2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, dichlorprop-P and its salts and esters, flopyrauxifen, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6);

b14) from the group of the auxin transport inhibitors: diflufenzopyr and diflufenzopyr-sodium;

b15) from the group of the other herbicides: bromobutide, cinmethylin, cumyluron, cyclopyrimorate (CAS 499223-49-3) and its salts and esters, dalapon, difenzoquat, difenzoquat-metilsulfate, DSMA, dymron (=daimuron), indanofan, metam, methylbromide, MSMA, oxaziclomefone, pyributicarb and tridiphane.

Particularly preferred herbicides B that can be used in combination with the forms A, B, C and/or D, preferably form C, of the formula (I) according to the present invention are:

b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3 (6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn, terbuthylazine, 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butylisoxazol-3-yl)-4-ethoxy-5-hydroxy-3-methyl-imidazolidin-2-one (CAS 1844836-64-1);

b4) from the group of the protoporphyrinogen-IX oxidase inhibitors: flumioxazin, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-di-oxo-1,2,3,4-tetrahydropyrimidin-3-yl)phenoxy]-2-pyridyloxy]acetate (CAS 353292-31-6; S-3100), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0);

b5) from the group of the bleacher herbicides: amitrole, bicyclopyrone, clomazone, diflufenican, fenquinotrione, flumeturon, flurochloridone, isoxaflutole, mesotrione, oxotrione (CAS 1486617-21-3), picolinafen, sulcotrione, tefuryltrione, tembotrione, tolpyralate, topramezone, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: indaziflam, isoxaben and triaziflam;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, flopyrauxifen, fluroxypyr-meptyl, halauxifen, halauxifen-methyl, quinclorac, quinmerac, florpyrauxifen, florpyrauxifen-benzyl (CAS 1390661-72-9) and 4-amino-3-chloro-5-fluoro-6-(7-fluoro-1H-indol-6-yl) picolinic acid (CAS 1629965-65-6;

b14) from the group of the auxin transport inhibitors: diflufenzopyr and diflufenzopyr-sodium, b15) from the group of the other herbicides: cinmethylin, dymon (=daimuron), indanofan, oxaziclomefone.

The herbicidal compounds B having a carboxyl group can be employed in form of the acid, in the form of an agriculturally suitable salt as mentioned above or else in the form of an agriculturally acceptable derivative as mentioned above.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. For example, suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanol-ammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)-ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are for example 2,4-DB-sodium, 2,4-DB-potassium and 2,4-DB-dimethylammonium. Suitable esters of 2,4-DB are for example 2,4-DB-butyl and 2,4-DB-isoctyl.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl. Suitable salts of clopyralid are clopyralid-potassium, clopyralid-olamine and clopyralid-tris-(2-hydroxypropyl)ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium. Suitable salts of glyphosate are for example glyphosate-ammonium, glyphosate-diammonium, glyphosate-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium. Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinmerac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Particularly preferred herbicidal compounds B are the herbicides B as defined above; in particular the herbicides B.1-B.202 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |

TABLE B-continued

| | Herbicide B |
|---|---|
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | pyraflufen |
| B.93 | pyraflufen-ethyl |
| B.94 | saflufenacil |
| B.95 | sulfentrazone |
| B.96 | trifludimoxazin |
| B.97 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) |
| B.98 | benzobicyclon |
| B.99 | bicyclopyrone |
| B.100 | clomazone |
| B.101 | diflufenican |
| B.102 | flurochloridone |
| B.103 | isoxaflutole |
| B.104 | mesotrione |
| B.105 | norflurazone |
| B.106 | picolinafen |
| B.107 | sulcotrione |
| B.108 | tefuryltrione |
| B.109 | tembotrione |
| B.110 | tolpyralate |
| B.111 | topramezone |
| B.112 | topramezone-sodium |
| B.113 | amitrole |
| B.114 | fluometuron |
| B.115 | fenquinotrione |
| B.116 | glyphosate |
| B.117 | glyphosate-ammonium |
| B.118 | glyphosate-dimethylammonium |
| B.119 | glyphosate-isopropylammonium |
| B.120 | glyphosate-trimesium (sulfosate) |
| B.121 | glyphosate-potassium |
| B.122 | glufosinate |
| B.123 | glufosinate-ammonium |
| B.124 | glufosinate-P |
| B.125 | glufosinate-P-ammonium |
| B.126 | pendimethalin |
| B.127 | trifluralin |
| B.128 | acetochlor |
| B.129 | butachlor |
| B.130 | cafenstrole |
| B.131 | dimethenamid-P |

TABLE B-continued

| | Herbicide B | |
|---|---|---|
| B.132 | fentrazamide | |
| B.133 | flufenacet | |
| B.134 | mefenacet | |
| B.135 | metazachlor | |
| B.136 | metolachlor | |
| B.137 | S-metolachlor | |
| B.138 | pretilachlor | |
| B.139 | fenoxasulfone | |
| B.140 | indaziflam | |
| B.141 | isoxaben | |
| B.142 | triaziflam | |
| B.143 | ipfencarbazone | |
| B.144 | pyroxasulfone | |
| B.145 | 2,4-D | |
| B.146 | 2,4-D-isobutyl | |
| B.147 | 2,4-D-dimethylammonium | |
| B.148 | 2,4-D-N,N,N-trimethylethanolammonium | |
| B.149 | aminopyralid | |
| B.150 | aminopyralid-methyl | |
| B.151 | aminopyralid-dimethyl-ammonium | |
| B.152 | aminopyralid-tris(2-hydroxypropyl)ammonium | |
| B.153 | clopyralid | |
| B.154 | clopyralid-methyl | |
| B.155 | clopyralid-olamine | |
| B.156 | dicamba | |
| B.157 | dicamba-butotyl | |
| B.158 | dicamba-diglycolamine | |
| B.159 | dicamba-dimethylammonium | |
| B.160 | dicamba-diolamine | |
| B.161 | dicamba-isopropylammonium | |
| B.162 | dicamba-potassium | |
| B.163 | dicamba-sodium | |
| B.164 | dicamba-trolamine | |
| B.165 | dicamba-N,N-bis-(3-aminopropyl)methylamine | |
| B.166 | dicamba-diethylenetriamine | |
| B.167 | fluroxypyr | |
| B.168 | fluroxypyr-meptyl | |
| B.169 | halauxifen | |
| B.170 | halauxifen-methyl | |
| B.171 | MCPA | |
| B.172 | MCPA-2-ethylhexyl | |
| B.173 | MCPA-dimethylammonium | |
| B.174 | quinclorac | |
| B.175 | quinclorac-dimethylammonium | |
| B.176 | quinmerac | |
| B.177 | quinmerac-dimethylammonium | |
| B.178 | florpyrauxifen | |
| B.179 | florpyrauxifen-benzyl (CAS 1390661-72-9) | |
| B.180 | aminocyclopyrachlor | |
| B.181 | aminocyclopyrachlor-potassium | |
| B.182 | aminocyclopyrachlor-methyl | |
| B.183 | diflufenzopyr | |
| B.184 | diflufenzopyr-sodium | |
| B.185 | dymron | |
| B.186 | indanofan | |
| B.187 | oxaziclomefone | |
| B.188 | II.1 | |
| B.189 | II.2 | |
| B.190 | II.3 | |
| B.191 | II.4 | |
| B.192 | II.5 | |
| B.193 | II.6 | |
| B.194 | II.7 | |
| B.195 | II.8 | |
| B.196 | II.9 | |
| B.197 | 4-amino-3-chloro-5-fluoro-6-(7-fluoro-1H-indol-6-yl)picolinic acid (CAS 1629965-65-6) | |
| B.198 | flopyrauxifen | |
| B.199 | oxotrione (CAS 1486617-21-3) | |
| B.200 | cinmethylin | |
| B.201 | 2-chloro-3-methylsulfanyl-N-(1-methyltetrazol-5-yl)-4-(trifluoromethyl)benzamide (CAS 1361139-71-0) | |
| B.202 | 2-(2,4-dichlorophenyl)-methyl-4,4-dimethyl-3-isoxazolidone (CAS 81777-95-9) | |

Moreover, it may be useful to apply the forms A, B, C and/or D, preferably form C, of formula (I) in combination with safeners. Safeners are chemical compounds which prevent or reduce damage on useful plants without having a major impact on the herbicidal action of the forms A, B, C and/or D, preferably form C, towards unwanted plants. They can be applied either before sowings (e.g. on seed treatments, shoots or seedlings) or in the pre-emergence application or post-emergence application of the useful plant. The safeners and the forms A, B, C and/or D, preferably form C, of formula (I), and optionally the herbicides B can be applied simultaneously or in succession.

In another embodiment of the present invention the compositions according to the present invention comprise the forms A, B, C and/or D, preferably form C, and at least one safener C (component C).

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenyl-carbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4), metcamifen (CAS 129531-12-0) and BPCMS (CAS 54091-06-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro-[4.5]decane (MON4660, CAS 71526-07-3), 2,2,5-trimethyl-3-(dichloroacetyl)-1,3-oxazolidine (R-29148, CAS 52836-31-4) and metcamifen (CAS 129531-12-0).

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and metcamifen (CAS 129531-12-0).

Particularly preferred safeners C, which, as component C, are constituent of the composition according to the invention are the safeners C as defined above; in particular the safeners C.1-C.17 listed below in table C:

TABLE C

| | Safener C |
|---|---|
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | metcamifen (CAS 129531-12-0) |

The active compounds B of groups b1) to b15) and the active compounds C are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one form A, B or C, preferably form A or B, more preferably form A, and as component B at least one, preferably exactly one, herbicide B.

According to another preferred embodiment of the invention, the composition comprises as component A at least one form A, B, C or D, preferably form C, and at least two, preferably exactly two, herbicides B different from each other.

According to another preferred embodiment of the invention, the composition comprises as component A at least one form A, B, C or D, preferably form C, and at least three, preferably exactly three, herbicides B different from each other.

According to another preferred embodiment of the invention, the composition comprises as component A at least one form A, B, C or D, preferably form C, and as component C at least one, preferably exactly one, safener C.

According to another preferred embodiment of the invention, the composition comprises as component A at least one form A, B, C or D, preferably form C, as component B at least one, preferably exactly one, herbicide B, and as component C at least one, preferably exactly one safener C.

According to another preferred embodiment of the invention, the composition comprises as component A at least one form A, B, C or D, preferably form C, as component B at least two, preferably exactly two herbicides B different from each other, and as component C at least one, preferably exactly one, safener C.

According to another preferred embodiment of the invention, the composition comprises as component A at least one form A, B, C or D preferably form C, as component B at least three, preferably exactly three herbicides B different from each other, and as component C at least one, preferably exactly one, safener C.

According to another preferred embodiment of the invention, the composition comprises, in addition form A, B, C and/or D, preferably form C, at least one and especially exactly one herbicidally active compound from group b1), in particular selected from the group consisting of clethodim, clodinafop-propargyl, cycloxydim, cyhalofop-butyl, fenoxaprop-ethyl, fenoxaprop-P-ethyl, metamifop, pinoxaden, profoxydim, sethoxydim, tepraloxydim, tralkoxydim, esprocarb, ethofumesate, molinate, prosulfocarb, thiobencarb and triallate.

According to another preferred embodiment of the invention, the composition comprises, in addition to form A, B, C and/or D, preferably form C, at least one and especially exactly one herbicidally active compound from group b2), in particular selected from the group consisting of bensulfuron-methyl, bispyribac-sodium, cloransulam-methyl, chlorsulfuron, clorimuron, cyclosulfamuron, diclosulam, florasulam, flumetsulam, flupyrsulfuron-methyl-sodium, foramsulfuron, imazamox, imazamox-ammonium, imazapic, imazapic-ammonium, imazapic-isopropylammonium, imazapyr, imazapyr-ammonium, imazethapyr-isopropylammonium, imazaquin, imazaquin-ammonium, imazethapyr, imazethapyr-ammonium, imazethapyr-isopropylammonium, imazosulfuron, iodosulfuron-methyl-sodium, iofensulfuron, iofensulfuron-sodium, mesosulfuron-methyl, metazosulfuron, metsulfuron-methyl, metosulam, nicosulfuron, penoxsulam, propoxycarbazon-sodium, pyrazosulfuron-ethyl, pyribenzoxim, pyriftalid, pyroxsulam, propyrisulfuron, rimsulfuron, sulfosulfuron, thiencarbazon-methyl, thifensulfuron-methyl, tribenuron-methyl, tritosulfuron and triafamone.

According to another preferred embodiment of the invention, the composition comprises, in addition to form A, B, C and/or D, preferably form C, at least one and especially exactly one herbicidally active compound from group b3), in particular selected from the group consisting of ametryn, atrazine, bentazon, bromoxynil, bromoxynil-octanoate, bromoxynil-heptanoate, bromoxynil-potassium, diuron, fluometuron, hexazinone, isoproturon, linuron, metamitron, metribuzin, paraquat-dichloride, propanil, simazin, terbutryn and terbuthylazine.

According to another preferred embodiment of the invention, the composition comprises, in addition to form A, B, C and/or D, preferably form C, at least one and especially exactly one herbicidally active compound from group b4), in particular selected from the group consisting of acifluorfen, butafencil, carfenetrazone-ethyl, flumioxazin, fomesafen, oxadiargyl, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100).

According to another preferred embodiment of the invention, the composition comprises, in addition to form A, B, C and/or D, preferably form C, at least one and especially exactly one herbicidally active compound from group b5), in particular selected from the group consisting of amitrole, benzobicyclon, bicyclopyrone, clomazone, diflufenican, fenquintrone, fluometuron, flurochloridone, isoxaflutole, mesotrione, norflurazone, oxotrione (CAS 1486617-21-3), picolinafen, sulcotrione, tefuryltrione, tembotrione, tolpyralate, topramezone, topramezone-sodium, 2-chloro-3-methylsulfanyl-N-(1-methyltetrazol-5-yl)-4-(trifluoromethyl) benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7).

According to another preferred embodiment of the invention, the composition comprises, in addition to form A, B, C and/or D, preferably form C, at least one and especially exactly one herbicidally active compound from group b6), in particular selected from the group consisting of glyphosate, glyphosate-ammonium, glyphosate-dimethylammonium, glyphosate-isopropylammonium and glyphosate-trimesium (sulfosate) and glyphosate-potassium.

According to another preferred embodiment of the invention, the composition comprises, in addition to form A, B, C and/or D, preferably form C, at least one and especially exactly one herbicidally active compound from group b7), in particular selected from the group consisting of glufosinate, glufosinate-ammonium, glufosinate-P and glufosinate-P-ammonium.

According to another preferred embodiment of the invention, the composition comprises, in addition to form A, B, C and/or D, preferably form C, at least one and especially exactly one herbicidally active compound from group b9), in particular selected from the group consisting of pendimethalin and trifluralin.

According to another preferred embodiment of the invention, the composition comprises, in addition to form A, B, C and/or D, preferably form C, at least one and especially exactly one herbicidally active compound from group b10), in particular selected from the group consisting of acetochlor, butachlor, cafenstrole, dimethenamid-P, fentrazamide, flufenacet, mefenacet, metazachlor, metolachlor, S-metolachlor, fenoxasulfone, ipfencarbazone and pyroxasulfone. Likewise, preference is given to compositions comprising in addition to form A, B or C, preferably form A or B, more preferably form A, at least one and especially exactly one herbicidally active compound from group b10), in particular selected from the group consisting of isoxazoline compounds of the formulae II.1, II.2, II.3, II.4, II.5, II.6, II.7, II.8 and II.9, as defined above.

According to another preferred embodiment of the invention, the composition comprises, in addition to form A, B, C and/or D, preferably form C, at least one and especially exactly one herbicidally active compound from group b11), in particular indaziflam, isoxaben and triaziflam.

According to another preferred embodiment of the invention, the composition comprises, in addition to form A, B, C and/or D, preferably form C, at least one and especially exactly one herbicidally active compound from group b13), in particular selected from the group consisting of 2,4-D, 2,4-D-isobutyl, 2,4-D-dimethylammonium, 2,4-D-N,N,N-trimethylethanolammonium, aminocyclopyrachlor, aminocyclopyrachlor-potassium, aminocyclopyrachlor-methyl, aminopyralid, aminopyralid-methyl, aminopyralid-dimethylammonium, aminopyralid-tris(2-hydroxypropyl)ammonium, clopyralid, clopyralid-methyl, clopyralid-olamine, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine, dicamba-diethylenetriamine, flopyrauxifen, fluroxypyr, fluroxypyr-meptyl, halauxifen, halauxifen-methyl, MCPA, MCPA-2-ethylhexyl, MCPA-dimethylammonium, quinclorac, quinclorac-dimethylammonium, quinmerac, quinmerac-dimethylammonium, florpyrauxifen, florpyrauxifen-benzyl (CAS 1390661-72-9), and 4-amino-3-chloro-5-fluoro-6-(7-fluoro-1H-indol-6-yl)picolinic acid (CAS 1629965-65-6).

According to another preferred embodiment of the invention, the composition comprises, in addition to form A, B, C and/or D, preferably form C, at least one and especially exactly one herbicidally active compound from group b14), in particular selected from the group consisting of diflufenzopyr, diflufenzopyr-sodium, dymron, indanofan and diflufenzopyr-sodium.

According to another preferred embodiment of the invention, the composition comprises, in addition to form A, B, C and/or D, preferably form C, at least one and especially exactly one herbicidally active compound from group b15), in particular selected from the group consisting of cinmethylin, dymron (=daimuron), indanofan and oxaziclomefone.

According to another preferred embodiment of the invention, the composition comprises, in addition to form A, B, C and/or D, preferably form C, at least one and especially exactly one safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, for example 1, 2 or 3, active compounds of the formula (I) and either one or more, for example 1, 2 or 3, herbicides B or one or more safeners C.

Correspondingly, the term "ternary compositions" includes compositions comprising one or more, for example 1, 2 or 3, active compounds of the formula (I), one or more, for example 1, 2 or 3, herbicides B and one or more, for example 1, 2 or 3, safeners C.

In binary compositions comprising at least one form A, B, C or D, preferably form C, as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least form A, B, C or D, preferably form C, as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising at least one form A, B, C or D, preferably form C, as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. The weight ratio of components A+B to component C is preferably in the range of from 1:500 to 500:1, in particular in the range of from 1:250 to 250:1 and particularly preferably in the range of from 1:75 to 75:1.

The weight ratios of the individual components in the preferred mixtures mentioned below are within the limits given herein, in particular within the preferred limits. Particularly preferred are the compositions mentioned below comprising form C as defined and the substance(s) as defined in the respective row of table 1; especially preferred comprising as only herbicidal active compounds form as defined and the substance(s) as defined in the respective row of table 1; most preferably comprising as only active compounds form C as defined and the substance(s) as defined in the respective row of table 1.

Particularly preferred are compositions 1.1 to 1.3653, comprising the comprising form C of the compound of formula (I) and the substance(s) as defined in the respective row of table 1:

TABLE 1

(compositions 1.1 to 1.3653):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |

TABLE 1-continued (compositions 1.1 to 1.3653):

| comp. no. | herbicide B | safener C |
|---|---|---|
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |
| 1.196 | B.196 | — |
| 1.197 | B.197 | — |
| 1.198 | B.198 | — |
| 1.199 | B.199 | — |
| 1.200 | B.200 | — |
| 1.201 | B.201 | — |
| 1.202 | B.202 | — |
| 1.203 | B.1 | C.1 |
| 1.204 | B.2 | C.1 |
| 1.205 | B.3 | C.1 |
| 1.206 | B.4 | C.1 |
| 1.207 | B.5 | C.1 |
| 1.208 | B.6 | C.1 |
| 1.209 | B.7 | C.1 |
| 1.210 | B.8 | C.1 |
| 1.211 | B.9 | C.1 |
| 1.212 | B.10 | C.1 |
| 1.213 | B.11 | C.1 |
| 1.214 | B.12 | C.1 |
| 1.215 | B.13 | C.1 |
| 1.216 | B.14 | C.1 |
| 1.217 | B.15 | C.1 |
| 1.218 | B.16 | C.1 |
| 1.219 | B.17 | C.1 |
| 1.220 | B.18 | C.1 |
| 1.221 | B.19 | C.1 |
| 1.222 | B.20 | C.1 |
| 1.223 | B.21 | C.1 |
| 1.224 | B.22 | C.1 |
| 1.225 | B.23 | C.1 |
| 1.226 | B.24 | C.1 |
| 1.227 | B.25 | C.1 |

TABLE 1-continued (compositions 1.1 to 1.3653):

| comp. no. | herbicide B | safener C |
|---|---|---|
| 1.228 | B.26 | C.1 |
| 1.229 | B.27 | C.1 |
| 1.230 | B.28 | C.1 |
| 1.231 | B.29 | C.1 |
| 1.232 | B.30 | C.1 |
| 1.233 | B.31 | C.1 |
| 1.234 | B.32 | C.1 |
| 1.235 | B.33 | C.1 |
| 1.236 | B.34 | C.1 |
| 1.237 | B.35 | C.1 |
| 1.238 | B.36 | C.1 |
| 1.239 | B.37 | C.1 |
| 1.240 | B.38 | C.1 |
| 1.241 | B.39 | C.1 |
| 1.242 | B.40 | C.1 |
| 1.243 | B.41 | C.1 |
| 1.244 | B.42 | C.1 |
| 1.245 | B.43 | C.1 |
| 1.246 | B.44 | C.1 |
| 1.247 | B.45 | C.1 |
| 1.248 | B.46 | C.1 |
| 1.249 | B.47 | C.1 |
| 1.250 | B.48 | C.1 |
| 1.251 | B.49 | C.1 |
| 1.252 | B.50 | C.1 |
| 1.253 | B.51 | C.1 |
| 1.254 | B.52 | C.1 |
| 1.255 | B.53 | C.1 |
| 1.256 | B.54 | C.1 |
| 1.257 | B.55 | C.1 |
| 1.258 | B.56 | C.1 |
| 1.259 | B.57 | C.1 |
| 1.260 | B.58. | C.1 |
| 1.261 | B.59 | C.1 |
| 1.262 | B.60 | C.1 |
| 1.263 | B.61 | C.1 |
| 1.264 | B.62 | C.1 |
| 1.265 | B.63 | C.1 |
| 1.266 | B.64 | C.1 |
| 1.267 | B.65 | C.1 |
| 1.268 | B.66 | C.1 |
| 1.269 | B.67 | C.1 |
| 1.270 | B.68 | C.1 |
| 1.271 | B.69 | C.1 |
| 1.272 | B.70 | C.1 |
| 1.273 | B.71 | C.1 |
| 1.274 | B.72 | C.1 |
| 1.275 | B.73 | C.1 |
| 1.276 | B.74 | C.1 |
| 1.277 | B.75 | C.1 |
| 1.278 | B.76 | C.1 |
| 1.279 | B.77 | C.1 |
| 1.280 | B.78 | C.1 |
| 1.281 | B.79 | C.1 |
| 1.282 | B.80 | C.1 |
| 1.283 | B.81 | C.1 |
| 1.284 | B.82 | C.1 |
| 1.285 | B.83 | C.1 |
| 1.286 | B.84 | C.1 |
| 1.287 | B.85 | C.1 |
| 1.288 | B.86 | C.1 |
| 1.289 | B.87 | C.1 |
| 1.290 | B.88 | C.1 |
| 1.291 | B.89 | C.1 |
| 1.292 | B.90 | C.1 |
| 1.293 | B.91 | C.1 |
| 1.294 | B.92 | C.1 |
| 1.295 | B.93 | C.1 |
| 1.296 | B.94 | C.1 |
| 1.297 | B.95 | C.1 |
| 1.298 | B.96 | C.1 |
| 1.299 | B.97 | C.1 |
| 1.300 | B.98 | C.1 |
| 1.301 | B.99 | C.1 |
| 1.302 | B.100 | C.1 |
| 1.303 | B.101 | C.1 |
| 1.304 | B.102 | C.1 |
| 1.305 | B.103 | C.1 |
| 1.306 | B.104 | C.1 |
| 1.307 | B.105 | C.1 |
| 1.308 | B.106 | C.1 |
| 1.309 | B.107 | C.1 |
| 1.310 | B.108 | C.1 |
| 1.311 | B.109 | C.1 |
| 1.312 | B.110 | C.1 |
| 1.313 | B.111 | C.1 |
| 1.314 | B.112 | C.1 |
| 1.315 | B.113 | C.1 |
| 1.316 | B.114 | C.1 |
| 1.317 | B.115 | C.1 |
| 1.318 | B.116 | C.1 |
| 1.319 | B.117 | C.1 |
| 1.320 | B.118 | C.1 |
| 1.321 | B.119 | C.1 |
| 1.322 | B.120 | C.1 |
| 1.323 | B.121 | C.1 |
| 1.324 | B.122 | C.1 |
| 1.325 | B.123 | C.1 |
| 1.326 | B.124 | C.1 |
| 1.327 | B.125 | C.1 |
| 1.328 | B.126 | C.1 |
| 1.329 | B.127 | C.1 |
| 1.330 | B.128 | C.1 |
| 1.331 | B.129 | C.1 |
| 1.332 | B.130 | C.1 |
| 1.333 | B.131 | C.1 |
| 1.334 | B.132 | C.1 |
| 1.335 | B.133 | C.1 |
| 1.336 | B.134 | C.1 |
| 1.337 | B.135 | C.1 |
| 1.338 | B.136 | C.1 |
| 1.339 | B.137 | C.1 |
| 1.340 | B.138 | C.1 |
| 1.341 | B.139 | C.1 |
| 1.342 | B.140 | C.1 |
| 1.343 | B.141 | C.1 |
| 1.344 | B.142 | C.1 |
| 1.345 | B.143 | C.1 |
| 1.346 | B.144 | C.1 |
| 1.347 | B.145 | C.1 |
| 1.348 | B.146 | C.1 |
| 1.349 | B.147 | C.1 |
| 1.350 | B.148 | C.1 |
| 1.351 | B.149 | C.1 |
| 1.352 | B.150 | C.1 |
| 1.353 | B.151 | C.1 |
| 1.354 | B.152 | C.1 |
| 1.355 | B.153 | C.1 |
| 1.356 | B.154 | C.1 |
| 1.357 | B.155 | C.1 |
| 1.358 | B.156 | C.1 |
| 1.359 | B.157 | C.1 |
| 1.360 | B.158 | C.1 |
| 1.361 | B.159 | C.1 |
| 1.362 | B.160 | C.1 |
| 1.363 | B.161 | C.1 |
| 1.364 | B.162 | C.1 |
| 1.365 | B.163 | C.1 |
| 1.366 | B.164 | C.1 |
| 1.367 | B.165 | C.1 |
| 1.368 | B.166 | C.1 |
| 1.369 | B.167 | C.1 |
| 1.370 | B.168 | C.1 |
| 1.371 | B.169 | C.1 |
| 1.372 | B.170 | C.1 |
| 1.373 | B.171 | C.1 |
| 1.374 | B.172 | C.1 |
| 1.375 | B.173 | C.1 |
| 1.376 | B.174 | C.1 |
| 1.377 | B.175 | C.1 |

TABLE 1-continued (compositions 1.1 to 1.3653):

| comp. no. | herbicide B | safener C |
|---|---|---|
| 1.378 | B.176 | C.1 |
| 1.379 | B.177 | C.1 |
| 1.380 | B.178 | C.1 |
| 1.381 | B.179 | C.1 |
| 1.382 | B.180 | C.1 |
| 1.383 | B.181 | C.1 |
| 1.384 | B.182 | C.1 |
| 1.385 | B.183 | C.1 |
| 1.386 | B.184 | C.1 |
| 1.387 | B.185 | C.1 |
| 1.388 | B.186 | C.1 |
| 1.389 | B.187 | C.1 |
| 1.390 | B.188 | C.1 |
| 1.391 | B.189 | C.1 |
| 1.392 | B.190 | C.1 |
| 1.393 | B.191 | C.1 |
| 1.394 | B.192 | C.1 |
| 1.395 | B.193 | C.1 |
| 1.396 | B.194 | C.1 |
| 1.397 | B.195 | C.1 |
| 1.398 | B.196 | C.1 |
| 1.399 | B.197 | C.1 |
| 1.400 | B.198 | C.1 |
| 1.401 | B.199 | C.1 |
| 1.402 | B.200 | C.1 |
| 1.403 | B.201 | C.1 |
| 1.404 | B.202 | C.1 |
| 1.405 | B.1 | C.2 |
| 1.406 | B.2 | C.2 |
| 1.407 | B.3 | C.2 |
| 1.408 | B.4 | C.2 |
| 1.409 | B.5 | C.2 |
| 1.410 | B.6 | C.2 |
| 1.411 | B.7 | C.2 |
| 1.412 | B.8 | C.2 |
| 1.413 | B.9 | C.2 |
| 1.414 | B.10 | C.2 |
| 1.415 | B.11 | C.2 |
| 1.416 | B.12 | C.2 |
| 1.417 | B.13 | C.2 |
| 1.418 | B.14 | C.2 |
| 1.419 | B.15 | C.2 |
| 1.420 | B.16 | C.2 |
| 1.421 | B.17 | C.2 |
| 1.422 | B.18 | C.2 |
| 1.423 | B.19 | C.2 |
| 1.424 | B.20 | C.2 |
| 1.425 | B.21 | C.2 |
| 1.426 | B.22 | C.2 |
| 1.427 | B.23 | C.2 |
| 1.428 | B.24 | C.2 |
| 1.429 | B.25 | C.2 |
| 1.430 | B.26 | C.2 |
| 1.431 | B.27 | C.2 |
| 1.432 | B.28 | C.2 |
| 1.433 | B.29 | C.2 |
| 1.434 | B.30 | C.2 |
| 1.435 | B.31 | C.2 |
| 1.436 | B.32 | C.2 |
| 1.437 | B.33 | C.2 |
| 1.438 | B.34 | C.2 |
| 1.439 | B.35 | C.2 |
| 1.440 | B.36 | C.2 |
| 1.441 | B.37 | C.2 |
| 1.442 | B.38 | C.2 |
| 1.443 | B.39 | C.2 |
| 1.444 | B.40 | C.2 |
| 1.445 | B.41 | C.2 |
| 1.446 | B.42 | C.2 |
| 1.447 | B.43 | C.2 |
| 1.448 | B.44 | C.2 |
| 1.449 | B.45 | C.2 |
| 1.450 | B.46 | C.2 |
| 1.451 | B.47 | C.2 |
| 1.452 | B.48 | C.2 |
| 1.453 | B.49 | C.2 |
| 1.454 | B.50 | C.2 |
| 1.455 | B.51 | C.2 |
| 1.456 | B.52 | C.2 |
| 1.457 | B.53 | C.2 |
| 1.458 | B.54 | C.2 |
| 1.459 | B.55 | C.2 |
| 1.460 | B.56 | C.2 |
| 1.461 | B.57 | C.2 |
| 1.462 | B.58. | C.2 |
| 1.463 | B.59 | C.2 |
| 1.464 | B.60 | C.2 |
| 1.465 | B.61 | C.2 |
| 1.466 | B.62 | C.2 |
| 1.467 | B.63 | C.2 |
| 1.468 | B.64 | C.2 |
| 1.469 | B.65 | C.2 |
| 1.470 | B.66 | C.2 |
| 1.471 | B.67 | C.2 |
| 1.472 | B.68 | C.2 |
| 1.473 | B.69 | C.2 |
| 1.474 | B.70 | C.2 |
| 1.475 | B.71 | C.2 |
| 1.476 | B.72 | C.2 |
| 1.477 | B.73 | C.2 |
| 1.478 | B.74 | C.2 |
| 1.479 | B.75 | C.2 |
| 1.480 | B.76 | C.2 |
| 1.481 | B.77 | C.2 |
| 1.482 | B.78 | C.2 |
| 1.483 | B.79 | C.2 |
| 1.484 | B.80 | C.2 |
| 1.485 | B.81 | C.2 |
| 1.486 | B.82 | C.2 |
| 1.487 | B.83 | C.2 |
| 1.488 | B.84 | C.2 |
| 1.489 | B.85 | C.2 |
| 1.490 | B.86 | C.2 |
| 1.491 | B.87 | C.2 |
| 1.492 | B.88 | C.2 |
| 1.493 | B.89 | C.2 |
| 1.494 | B.90 | C.2 |
| 1.495 | B.91 | C.2 |
| 1.496 | B.92 | C.2 |
| 1.497 | B.93 | C.2 |
| 1.498 | B.94 | C.2 |
| 1.499 | B.95 | C.2 |
| 1.500 | B.96 | C.2 |
| 1.501 | B.97 | C.2 |
| 1.502 | B.98 | C.2 |
| 1.503 | B.99 | C.2 |
| 1.504 | B.100 | C.2 |
| 1.505 | B.101 | C.2 |
| 1.506 | B.102 | C.2 |
| 1.507 | B.103 | C.2 |
| 1.508 | B.104 | C.2 |
| 1.509 | B.105 | C.2 |
| 1.510 | B.106 | C.2 |
| 1.511 | B.107 | C.2 |
| 1.512 | B.108 | C.2 |
| 1.513 | B.109 | C.2 |
| 1.514 | B.110 | C.2 |
| 1.515 | B.111 | C.2 |
| 1.516 | B.112 | C.2 |
| 1.517 | B.113 | C.2 |
| 1.518 | B.114 | C.2 |
| 1.519 | B.115 | C.2 |
| 1.520 | B.116 | C.2 |
| 1.521 | B.117 | C.2 |
| 1.522 | B.118 | C.2 |
| 1.523 | B.119 | C.2 |
| 1.524 | B.120 | C.2 |
| 1.525 | B.121 | C.2 |
| 1.526 | B.122 | C.2 |
| 1.527 | B.123 | C.2 |

TABLE 1-continued (compositions 1.1 to 1.3653):

| comp. no. | herbicide B | safener C |
|---|---|---|
| 1.528 | B.124 | C.2 |
| 1.529 | B.125 | C.2 |
| 1.530 | B.126 | C.2 |
| 1.531 | B.127 | C.2 |
| 1.532 | B.128 | C.2 |
| 1.533 | B.129 | C.2 |
| 1.534 | B.130 | C.2 |
| 1.535 | B.131 | C.2 |
| 1.536 | B.132 | C.2 |
| 1.537 | B.133 | C.2 |
| 1.538 | B.134 | C.2 |
| 1.539 | B.135 | C.2 |
| 1.540 | B.136 | C.2 |
| 1.541 | B.137 | C.2 |
| 1.542 | B.138 | C.2 |
| 1.543 | B.139 | C.2 |
| 1.544 | B.140 | C.2 |
| 1.545 | B.141 | C.2 |
| 1.546 | B.142 | C.2 |
| 1.547 | B.143 | C.2 |
| 1.548 | B.144 | C.2 |
| 1.549 | B.145 | C.2 |
| 1.550 | B.146 | C.2 |
| 1.551 | B.147 | C.2 |
| 1.552 | B.148 | C.2 |
| 1.553 | B.149 | C.2 |
| 1.554 | B.150 | C.2 |
| 1.555 | B.151 | C.2 |
| 1.556 | B.152 | C.2 |
| 1.557 | B.153 | C.2 |
| 1.558 | B.154 | C.2 |
| 1.559 | B.155 | C.2 |
| 1.560 | B.156 | C.2 |
| 1.561 | B.157 | C.2 |
| 1.562 | B.158 | C.2 |
| 1.563 | B.159 | C.2 |
| 1.564 | B.160 | C.2 |
| 1.565 | B.161 | C.2 |
| 1.566 | B.162 | C.2 |
| 1.567 | B.163 | C.2 |
| 1.568 | B.164 | C.2 |
| 1.569 | B.165 | C.2 |
| 1.570 | B.166 | C.2 |
| 1.571 | B.167 | C.2 |
| 1.572 | B.168 | C.2 |
| 1.573 | B.169 | C.2 |
| 1.574 | B.170 | C.2 |
| 1.575 | B.171 | C.2 |
| 1.576 | B.172 | C.2 |
| 1.577 | B.173 | C.2 |
| 1.578 | B.174 | C.2 |
| 1.579 | B.175 | C.2 |
| 1.580 | B.176 | C.2 |
| 1.581 | B.177 | C.2 |
| 1.582 | B.178 | C.2 |
| 1.583 | B.179 | C.2 |
| 1.584 | B.180 | C.2 |
| 1.585 | B.181 | C.2 |
| 1.586 | B.182 | C.2 |
| 1.587 | B.183 | C.2 |
| 1.588 | B.184 | C.2 |
| 1.589 | B.185 | C.2 |
| 1.590 | B.186 | C.2 |
| 1.591 | B.187 | C.2 |
| 1.592 | B.188 | C.2 |
| 1.593 | B.189 | C.2 |
| 1.594 | B.190 | C.2 |
| 1.595 | B.191 | C.2 |
| 1.596 | B.192 | C.2 |
| 1.597 | B.193 | C.2 |
| 1.598 | B.194 | C.2 |
| 1.599 | B.195 | C.2 |
| 1.600 | B.196 | C.2 |
| 1.601 | B.197 | C.2 |
| 1.602 | B.198 | C.2 |
| 1.603 | B.199 | C.2 |
| 1.604 | B.200 | C.2 |
| 1.605 | B.201 | C.2 |
| 1.606 | B.202 | C.2 |
| 1.607 | B.1 | C.3 |
| 1.608 | B.2 | C.3 |
| 1.609 | B.3 | C.3 |
| 1.610 | B.4 | C.3 |
| 1.611 | B.5 | C.3 |
| 1.612 | B.6 | C.3 |
| 1.613 | B.7 | C.3 |
| 1.614 | B.8 | C.3 |
| 1.615 | B.9 | C.3 |
| 1.616 | B.10 | C.3 |
| 1.617 | B.11 | C.3 |
| 1.618 | B.12 | C.3 |
| 1.619 | B.13 | C.3 |
| 1.620 | B.14 | C.3 |
| 1.621 | B.15 | C.3 |
| 1.622 | B.16 | C.3 |
| 1.623 | B.17 | C.3 |
| 1.624 | B.18 | C.3 |
| 1.625 | B.19 | C.3 |
| 1.626 | B.20 | C.3 |
| 1.627 | B.21 | C.3 |
| 1.628 | B.22 | C.3 |
| 1.629 | B.23 | C.3 |
| 1.630 | B.24 | C.3 |
| 1.631 | B.25 | C.3 |
| 1.632 | B.26 | C.3 |
| 1.633 | B.27 | C.3 |
| 1.634 | B.28 | C.3 |
| 1.635 | B.29 | C.3 |
| 1.636 | B.30 | C.3 |
| 1.637 | B.31 | C.3 |
| 1.638 | B.32 | C.3 |
| 1.639 | B.33 | C.3 |
| 1.640 | B.34 | C.3 |
| 1.641 | B.35 | C.3 |
| 1.642 | B.36 | C.3 |
| 1.643 | B.37 | C.3 |
| 1.644 | B.38 | C.3 |
| 1.645 | B.39 | C.3 |
| 1.646 | B.40 | C.3 |
| 1.647 | B.41 | C.3 |
| 1.648 | B.42 | C.3 |
| 1.649 | B.43 | C.3 |
| 1.650 | B.44 | C.3 |
| 1.651 | B.45 | C.3 |
| 1.652 | B.46 | C.3 |
| 1.653 | B.47 | C.3 |
| 1.654 | B.48 | C.3 |
| 1.655 | B.49 | C.3 |
| 1.656 | B.50 | C.3 |
| 1.657 | B.51 | C.3 |
| 1.658 | B.52 | C.3 |
| 1.659 | B.53 | C.3 |
| 1.660 | B.54 | C.3 |
| 1.661 | B.55 | C.3 |
| 1.662 | B.56 | C.3 |
| 1.663 | B.57 | C.3 |
| 1.664 | B.58. | C.3 |
| 1.665 | B.59 | C.3 |
| 1.666 | B.60 | C.3 |
| 1.667 | B.61 | C.3 |
| 1.668 | B.62 | C.3 |
| 1.669 | B.63 | C.3 |
| 1.670 | B.64 | C.3 |
| 1.671 | B.65 | C.3 |
| 1.672 | B.66 | C.3 |
| 1.673 | B.67 | C.3 |
| 1.674 | B.68 | C.3 |
| 1.675 | B.69 | C.3 |
| 1.676 | B.70 | C.3 |
| 1.677 | B.71 | C.3 |

TABLE 1-continued (compositions 1.1 to 1.3653):

| comp. no. | herbicide B | safener C |
|---|---|---|
| 1.678 | B.72 | C.3 |
| 1.679 | B.73 | C.3 |
| 1.680 | B.74 | C.3 |
| 1.681 | B.75 | C.3 |
| 1.682 | B.76 | C.3 |
| 1.683 | B.77 | C.3 |
| 1.684 | B.78 | C.3 |
| 1.685 | B.79 | C.3 |
| 1.686 | B.80 | C.3 |
| 1.687 | B.81 | C.3 |
| 1.688 | B.82 | C.3 |
| 1.689 | B.83 | C.3 |
| 1.690 | B.84 | C.3 |
| 1.691 | B.85 | C.3 |
| 1.692 | B.86 | C.3 |
| 1.693 | B.87 | C.3 |
| 1.694 | B.88 | C.3 |
| 1.695 | B.89 | C.3 |
| 1.696 | B.90 | C.3 |
| 1.697 | B.91 | C.3 |
| 1.698 | B.92 | C.3 |
| 1.699 | B.93 | C.3 |
| 1.700 | B.94 | C.3 |
| 1.701 | B.95 | C.3 |
| 1.702 | B.96 | C.3 |
| 1.703 | B.97 | C.3 |
| 1.704 | B.98 | C.3 |
| 1.705 | B.99 | C.3 |
| 1.706 | B.100 | C.3 |
| 1.707 | B.101 | C.3 |
| 1.708 | B.102 | C.3 |
| 1.709 | B.103 | C.3 |
| 1.710 | B.104 | C.3 |
| 1.711 | B.105 | C.3 |
| 1.712 | B.106 | C.3 |
| 1.713 | B.107 | C.3 |
| 1.714 | B.108 | C.3 |
| 1.715 | B.109 | C.3 |
| 1.716 | B.110 | C.3 |
| 1.717 | B.111 | C.3 |
| 1.718 | B.112 | C.3 |
| 1.719 | B.113 | C.3 |
| 1.720 | B.114 | C.3 |
| 1.721 | B.115 | C.3 |
| 1.722 | B.116 | C.3 |
| 1.723 | B.117 | C.3 |
| 1.724 | B.118 | C.3 |
| 1.725 | B.119 | C.3 |
| 1.726 | B.120 | C.3 |
| 1.727 | B.121 | C.3 |
| 1.728 | B.122 | C.3 |
| 1.729 | B.123 | C.3 |
| 1.730 | B.124 | C.3 |
| 1.731 | B.125 | C.3 |
| 1.732 | B.126 | C.3 |
| 1.733 | B.127 | C.3 |
| 1.734 | B.128 | C.3 |
| 1.735 | B.129 | C.3 |
| 1.736 | B.130 | C.3 |
| 1.737 | B.131 | C.3 |
| 1.738 | B.132 | C.3 |
| 1.739 | B.133 | C.3 |
| 1.740 | B.134 | C.3 |
| 1.741 | B.135 | C.3 |
| 1.742 | B.136 | C.3 |
| 1.743 | B.137 | C.3 |
| 1.744 | B.138 | C.3 |
| 1.745 | B.139 | C.3 |
| 1.746 | B.140 | C.3 |
| 1.747 | B.141 | C.3 |
| 1.748 | B.142 | C.3 |
| 1.749 | B.143 | C.3 |
| 1.750 | B.144 | C.3 |
| 1.751 | B.145 | C.3 |
| 1.752 | B.146 | C.3 |
| 1.753 | B.147 | C.3 |
| 1.754 | B.148 | C.3 |
| 1.755 | B.149 | C.3 |
| 1.756 | B.150 | C.3 |
| 1.757 | B.151 | C.3 |
| 1.758 | B.152 | C.3 |
| 1.759 | B.153 | C.3 |
| 1.760 | B.154 | C.3 |
| 1.761 | B.155 | C.3 |
| 1.762 | B.156 | C.3 |
| 1.763 | B.157 | C.3 |
| 1.764 | B.158 | C.3 |
| 1.765 | B.159 | C.3 |
| 1.766 | B.160 | C.3 |
| 1.767 | B.161 | C.3 |
| 1.768 | B.162 | C.3 |
| 1.769 | B.163 | C.3 |
| 1.770 | B.164 | C.3 |
| 1.771 | B.165 | C.3 |
| 1.772 | B.166 | C.3 |
| 1.773 | B.167 | C.3 |
| 1.774 | B.168 | C.3 |
| 1.775 | B.169 | C.3 |
| 1.776 | B.170 | C.3 |
| 1.777 | B.171 | C.3 |
| 1.778 | B.172 | C.3 |
| 1.779 | B.173 | C.3 |
| 1.780 | B.174 | C.3 |
| 1.781 | B.175 | C.3 |
| 1.782 | B.176 | C.3 |
| 1.783 | B.177 | C.3 |
| 1.784 | B.178 | C.3 |
| 1.785 | B.179 | C.3 |
| 1.786 | B.180 | C.3 |
| 1.787 | B.181 | C.3 |
| 1.788 | B.182 | C.3 |
| 1.789 | B.183 | C.3 |
| 1.790 | B.184 | C.3 |
| 1.791 | B.185 | C.3 |
| 1.792 | B.186 | C.3 |
| 1.793 | B.187 | C.3 |
| 1.794 | B.188 | C.3 |
| 1.795 | B.189 | C.3 |
| 1.796 | B.190 | C.3 |
| 1.797 | B.191 | C.3 |
| 1.798 | B.192 | C.3 |
| 1.799 | B.193 | C.3 |
| 1.800 | B.194 | C.3 |
| 1.801 | B.195 | C.3 |
| 1.802 | B.196 | C.3 |
| 1.803 | B.197 | C.3 |
| 1.804 | B.198 | C.3 |
| 1.805 | B.199 | C.3 |
| 1.806 | B.200 | C.3 |
| 1.807 | B.201 | C.3 |
| 1.808 | B.202 | C.3 |
| 1.809 | B.1 | C.4 |
| 1.810 | B.2 | C.4 |
| 1.811 | B.3 | C.4 |
| 1.812 | B.4 | C.4 |
| 1.813 | B.5 | C.4 |
| 1.814 | B.6 | C.4 |
| 1.815 | B.7 | C.4 |
| 1.816 | B.8 | C.4 |
| 1.817 | B.9 | C.4 |
| 1.818 | B.10 | C.4 |
| 1.819 | B.11 | C.4 |
| 1.820 | B.12 | C.4 |
| 1.821 | B.13 | C.4 |
| 1.822 | B.14 | C.4 |
| 1.823 | B.15 | C.4 |
| 1.824 | B.16 | C.4 |
| 1.825 | B.17 | C.4 |
| 1.826 | B.18 | C.4 |
| 1.827 | B.19 | C.4 |

TABLE 1-continued (compositions 1.1 to 1.3653):

| comp. no. | herbicide B | safener C |
|---|---|---|
| 1.828 | B.20 | C.4 |
| 1.829 | B.21 | C.4 |
| 1.830 | B.22 | C.4 |
| 1.831 | B.23 | C.4 |
| 1.832 | B.24 | C.4 |
| 1.833 | B.25 | C.4 |
| 1.834 | B.26 | C.4 |
| 1.835 | B.27 | C.4 |
| 1.836 | B.28 | C.4 |
| 1.837 | B.29 | C.4 |
| 1.838 | B.30 | C.4 |
| 1.839 | B.31 | C.4 |
| 1.840 | B.32 | C.4 |
| 1.841 | B.33 | C.4 |
| 1.842 | B.34 | C.4 |
| 1.843 | B.35 | C.4 |
| 1.844 | B.36 | C.4 |
| 1.845 | B.37 | C.4 |
| 1.846 | B.38 | C.4 |
| 1.847 | B.39 | C.4 |
| 1.848 | B.40 | C.4 |
| 1.849 | B.41 | C.4 |
| 1.850 | B.42 | C.4 |
| 1.851 | B.43 | C.4 |
| 1.852 | B.44 | C.4 |
| 1.853 | B.45 | C.4 |
| 1.854 | B.46 | C.4 |
| 1.855 | B.47 | C.4 |
| 1.856 | B.48 | C.4 |
| 1.857 | B.49 | C.4 |
| 1.858 | B.50 | C.4 |
| 1.859 | B.51 | C.4 |
| 1.860 | B.52 | C.4 |
| 1.861 | B.53 | C.4 |
| 1.862 | B.54 | C.4 |
| 1.863 | B.55 | C.4 |
| 1.864 | B.56 | C.4 |
| 1.865 | B.57 | C.4 |
| 1.866 | B.58. | C.4 |
| 1.867 | B.59 | C.4 |
| 1.868 | B.60 | C.4 |
| 1.869 | B.61 | C.4 |
| 1.870 | B.62 | C.4 |
| 1.871 | B.63 | C.4 |
| 1.872 | B.64 | C.4 |
| 1.873 | B.65 | C.4 |
| 1.874 | B.66 | C.4 |
| 1.875 | B.67 | C.4 |
| 1.876 | B.68 | C.4 |
| 1.877 | B.69 | C.4 |
| 1.878 | B.70 | C.4 |
| 1.879 | B.71 | C.4 |
| 1.880 | B.72 | C.4 |
| 1.881 | B.73 | C.4 |
| 1.882 | B.74 | C.4 |
| 1.883 | B.75 | C.4 |
| 1.884 | B.76 | C.4 |
| 1.885 | B.77 | C.4 |
| 1.886 | B.78 | C.4 |
| 1.887 | B.79 | C.4 |
| 1.888 | B.80 | C.4 |
| 1.889 | B.81 | C.4 |
| 1.890 | B.82 | C.4 |
| 1.891 | B.83 | C.4 |
| 1.892 | B.84 | C.4 |
| 1.893 | B.85 | C.4 |
| 1.894 | B.86 | C.4 |
| 1.895 | B.87 | C.4 |
| 1.896 | B.88 | C.4 |
| 1.897 | B.89 | C.4 |
| 1.898 | B.90 | C.4 |
| 1.899 | B.91 | C.4 |
| 1.900 | B.92 | C.4 |
| 1.901 | B.93 | C.4 |
| 1.902 | B.94 | C.4 |
| 1.903 | B.95 | C.4 |
| 1.904 | B.96 | C.4 |
| 1.905 | B.97 | C.4 |
| 1.906 | B.98 | C.4 |
| 1.907 | B.99 | C.4 |
| 1.908 | B.100 | C.4 |
| 1.909 | B.101 | C.4 |
| 1.910 | B.102 | C.4 |
| 1.911 | B.103 | C.4 |
| 1.912 | B.104 | C.4 |
| 1.913 | B.105 | C.4 |
| 1.914 | B.106 | C.4 |
| 1.915 | B.107 | C.4 |
| 1.916 | B.108 | C.4 |
| 1.917 | B.109 | C.4 |
| 1.918 | B.110 | C.4 |
| 1.919 | B.111 | C.4 |
| 1.920 | B.112 | C.4 |
| 1.921 | B.113 | C.4 |
| 1.922 | B.114 | C.4 |
| 1.923 | B.115 | C.4 |
| 1.924 | B.116 | C.4 |
| 1.925 | B.117 | C.4 |
| 1.926 | B.118 | C.4 |
| 1.927 | B.119 | C.4 |
| 1.928 | B.120 | C.4 |
| 1.929 | B.121 | C.4 |
| 1.930 | B.122 | C.4 |
| 1.931 | B.123 | C.4 |
| 1.932 | B.124 | C.4 |
| 1.933 | B.125 | C.4 |
| 1.934 | B.126 | C.4 |
| 1.935 | B.127 | C.4 |
| 1.936 | B.128 | C.4 |
| 1.937 | B.129 | C.4 |
| 1.938 | B.130 | C.4 |
| 1.939 | B.131 | C.4 |
| 1.940 | B.132 | C.4 |
| 1.941 | B.133 | C.4 |
| 1.942 | B.134 | C.4 |
| 1.943 | B.135 | C.4 |
| 1.944 | B.136 | C.4 |
| 1.945 | B.137 | C.4 |
| 1.946 | B.138 | C.4 |
| 1.947 | B.139 | C.4 |
| 1.948 | B.140 | C.4 |
| 1.949 | B.141 | C.4 |
| 1.950 | B.142 | C.4 |
| 1.951 | B.143 | C.4 |
| 1.952 | B.144 | C.4 |
| 1.953 | B.145 | C.4 |
| 1.954 | B.146 | C.4 |
| 1.955 | B.147 | C.4 |
| 1.956 | B.148 | C.4 |
| 1.957 | B.149 | C.4 |
| 1.958 | B.150 | C.4 |
| 1.959 | B.151 | C.4 |
| 1.960 | B.152 | C.4 |
| 1.961 | B.153 | C.4 |
| 1.962 | B.154 | C.4 |
| 1.963 | B.155 | C.4 |
| 1.964 | B.156 | C.4 |
| 1.965 | B.157 | C.4 |
| 1.966 | B.158 | C.4 |
| 1.967 | B.159 | C.4 |
| 1.968 | B.160 | C.4 |
| 1.969 | B.161 | C.4 |
| 1.970 | B.162 | C.4 |
| 1.971 | B.163 | C.4 |
| 1.972 | B.164 | C.4 |
| 1.973 | B.165 | C.4 |
| 1.974 | B.166 | C.4 |
| 1.975 | B.167 | C.4 |
| 1.976 | B.168 | C.4 |
| 1.977 | B.169 | C.4 |

TABLE 1-continued (compositions 1.1 to 1.3653):

| comp. no. | herbicide B | safener C |
|---|---|---|
| 1.978 | B.170 | C.4 |
| 1.979 | B.171 | C.4 |
| 1.980 | B.172 | C.4 |
| 1.981 | B.173 | C.4 |
| 1.982 | B.174 | C.4 |
| 1.983 | B.175 | C.4 |
| 1.984 | B.176 | C.4 |
| 1.985 | B.177 | C.4 |
| 1.986 | B.178 | C.4 |
| 1.987 | B.179 | C.4 |
| 1.988 | B.180 | C.4 |
| 1.989 | B.181 | C.4 |
| 1.990 | B.182 | C.4 |
| 1.991 | B.183 | C.4 |
| 1.992 | B.184 | C.4 |
| 1.993 | B.185 | C.4 |
| 1.994 | B.186 | C.4 |
| 1.995 | B.187 | C.4 |
| 1.996 | B.188 | C.4 |
| 1.997 | B.189 | C.4 |
| 1.998 | B.190 | C.4 |
| 1.999 | B.191 | C.4 |
| 1.1000 | B.192 | C.4 |
| 1.1001 | B.193 | C.4 |
| 1.1002 | B.194 | C.4 |
| 1.1003 | B.195 | C.4 |
| 1.1004 | B.196 | C.4 |
| 1.1005 | B.197 | C.4 |
| 1.1006 | B.198 | C.4 |
| 1.1007 | B.199 | C.4 |
| 1.1008 | B.200 | C.4 |
| 1.1009 | B.201 | C.4 |
| 1.1010 | B.202 | C.4 |
| 1.1011 | B.1 | C.5 |
| 1.1012 | B.2 | C.5 |
| 1.1013 | B.3 | C.5 |
| 1.1014 | B.4 | C.5 |
| 1.1015 | B.5 | C.5 |
| 1.1016 | B.6 | C.5 |
| 1.1017 | B.7 | C.5 |
| 1.1018 | B.8 | C.5 |
| 1.1019 | B.9 | C.5 |
| 1.1020 | B.10 | C.5 |
| 1.1021 | B.11 | C.5 |
| 1.1022 | B.12 | C.5 |
| 1.1023 | B.13 | C.5 |
| 1.1024 | B.14 | C.5 |
| 1.1025 | B.15 | C.5 |
| 1.1026 | B.16 | C.5 |
| 1.1027 | B.17 | C.5 |
| 1.1028 | B.18 | C.5 |
| 1.1029 | B.19 | C.5 |
| 1.1030 | B.20 | C.5 |
| 1.1031 | B.21 | C.5 |
| 1.1032 | B.22 | C.5 |
| 1.1033 | B.23 | C.5 |
| 1.1034 | B.24 | C.5 |
| 1.1035 | B.25 | C.5 |
| 1.1036 | B.26 | C.5 |
| 1.1037 | B.27 | C.5 |
| 1.1038 | B.28 | C.5 |
| 1.1039 | B.29 | C.5 |
| 1.1040 | B.30 | C.5 |
| 1.1041 | B.31 | C.5 |
| 1.1042 | B.32 | C.5 |
| 1.1043 | B.33 | C.5 |
| 1.1044 | B.34 | C.5 |
| 1.1045 | B.35 | C.5 |
| 1.1046 | B.36 | C.5 |
| 1.1047 | B.37 | C.5 |
| 1.1048 | B.38 | C.5 |
| 1.1049 | B.39 | C.5 |
| 1.1050 | B.40 | C.5 |
| 1.1051 | B.41 | C.5 |
| 1.1052 | B.42 | C.5 |
| 1.1053 | B.43 | C.5 |
| 1.1054 | B.44 | C.5 |
| 1.1055 | B.45 | C.5 |
| 1.1056 | B.46 | C.5 |
| 1.1057 | B.47 | C.5 |
| 1.1058 | B.48 | C.5 |
| 1.1059 | B.49 | C.5 |
| 1.1060 | B.50 | C.5 |
| 1.1061 | B.51 | C.5 |
| 1.1062 | B.52 | C.5 |
| 1.1063 | B.53 | C.5 |
| 1.1064 | B.54 | C.5 |
| 1.1065 | B.55 | C.5 |
| 1.1066 | B.56 | C.5 |
| 1.1067 | B.57 | C.5 |
| 1.1068 | B.58. | C.5 |
| 1.1069 | B.59 | C.5 |
| 1.1070 | B.60 | C.5 |
| 1.1071 | B.61 | C.5 |
| 1.1072 | B.62 | C.5 |
| 1.1073 | B.63 | C.5 |
| 1.1074 | B.64 | C.5 |
| 1.1075 | B.65 | C.5 |
| 1.1076 | B.66 | C.5 |
| 1.1077 | B.67 | C.5 |
| 1.1078 | B.68 | C.5 |
| 1.1079 | B.69 | C.5 |
| 1.1080 | B.70 | C.5 |
| 1.1081 | B.71 | C.5 |
| 1.1082 | B.72 | C.5 |
| 1.1083 | B.73 | C.5 |
| 1.1084 | B.74 | C.5 |
| 1.1085 | B.75 | C.5 |
| 1.1086 | B.76 | C.5 |
| 1.1087 | B.77 | C.5 |
| 1.1088 | B.78 | C.5 |
| 1.1089 | B.79 | C.5 |
| 1.1090 | B.80 | C.5 |
| 1.1091 | B.81 | C.5 |
| 1.1092 | B.82 | C.5 |
| 1.1093 | B.83 | C.5 |
| 1.1094 | B.84 | C.5 |
| 1.1095 | B.85 | C.5 |
| 1.1096 | B.86 | C.5 |
| 1.1097 | B.87 | C.5 |
| 1.1098 | B.88 | C.5 |
| 1.1099 | B.89 | C.5 |
| 1.1100 | B.90 | C.5 |
| 1.1101 | B.91 | C.5 |
| 1.1102 | B.92 | C.5 |
| 1.1103 | B.93 | C.5 |
| 1.1104 | B.94 | C.5 |
| 1.1105 | B.95 | C.5 |
| 1.1106 | B.96 | C.5 |
| 1.1107 | B.97 | C.5 |
| 1.1108 | B.98 | C.5 |
| 1.1109 | B.99 | C.5 |
| 1.1110 | B.100 | C.5 |
| 1.1111 | B.101 | C.5 |
| 1.1112 | B.102 | C.5 |
| 1.1113 | B.103 | C.5 |
| 1.1114 | B.104 | C.5 |
| 1.1115 | B.105 | C.5 |
| 1.1116 | B.106 | C.5 |
| 1.1117 | B.107 | C.5 |
| 1.1118 | B.108 | C.5 |
| 1.1119 | B.109 | C.5 |
| 1.1120 | B.110 | C.5 |
| 1.1121 | B.111 | C.5 |
| 1.1122 | B.112 | C.5 |
| 1.1123 | B.113 | C.5 |
| 1.1124 | B.114 | C.5 |
| 1.1125 | B.115 | C.5 |
| 1.1126 | B.116 | C.5 |
| 1.1127 | B.117 | C.5 |

TABLE 1-continued (compositions 1.1 to 1.3653):

| comp. no. | herbicide B | safener C |
|---|---|---|
| 1.1128 | B.118 | C.5 |
| 1.1129 | B.119 | C.5 |
| 1.1130 | B.120 | C.5 |
| 1.1131 | B.121 | C.5 |
| 1.1132 | B.122 | C.5 |
| 1.1133 | B.123 | C.5 |
| 1.1134 | B.124 | C.5 |
| 1.1135 | B.125 | C.5 |
| 1.1136 | B.126 | C.5 |
| 1.1137 | B.127 | C.5 |
| 1.1138 | B.128 | C.5 |
| 1.1139 | B.129 | C.5 |
| 1.1140 | B.130 | C.5 |
| 1.1141 | B.131 | C.5 |
| 1.1142 | B.132 | C.5 |
| 1.1143 | B.133 | C.5 |
| 1.1144 | B.134 | C.5 |
| 1.1145 | B.135 | C.5 |
| 1.1146 | B.136 | C.5 |
| 1.1147 | B.137 | C.5 |
| 1.1148 | B.138 | C.5 |
| 1.1149 | B.139 | C.5 |
| 1.1150 | B.140 | C.5 |
| 1.1151 | B.141 | C.5 |
| 1.1152 | B.142 | C.5 |
| 1.1153 | B.143 | C.5 |
| 1.1154 | B.144 | C.5 |
| 1.1155 | B.145 | C.5 |
| 1.1156 | B.146 | C.5 |
| 1.1157 | B.147 | C.5 |
| 1.1158 | B.148 | C.5 |
| 1.1159 | B.149 | C.5 |
| 1.1160 | B.150 | C.5 |
| 1.1161 | B.151 | C.5 |
| 1.1162 | B.152 | C.5 |
| 1.1163 | B.153 | C.5 |
| 1.1164 | B.154 | C.5 |
| 1.1165 | B.155 | C.5 |
| 1.1166 | B.156 | C.5 |
| 1.1167 | B.157 | C.5 |
| 1.1168 | B.158 | C.5 |
| 1.1169 | B.159 | C.5 |
| 1.1170 | B.160 | C.5 |
| 1.1171 | B.161 | C.5 |
| 1.1172 | B.162 | C.5 |
| 1.1173 | B.163 | C.5 |
| 1.1174 | B.164 | C.5 |
| 1.1175 | B.165 | C.5 |
| 1.1176 | B.166 | C.5 |
| 1.1177 | B.167 | C.5 |
| 1.1178 | B.168 | C.5 |
| 1.1179 | B.169 | C.5 |
| 1.1180 | B.170 | C.5 |
| 1.1181 | B.171 | C.5 |
| 1.1182 | B.172 | C.5 |
| 1.1183 | B.173 | C.5 |
| 1.1184 | B.174 | C.5 |
| 1.1185 | B.175 | C.5 |
| 1.1186 | B.176 | C.5 |
| 1.1187 | B.177 | C.5 |
| 1.1188 | B.178 | C.5 |
| 1.1189 | B.179 | C.5 |
| 1.1190 | B.180 | C.5 |
| 1.1191 | B.181 | C.5 |
| 1.1192 | B.182 | C.5 |
| 1.1193 | B.183 | C.5 |
| 1.1194 | B.184 | C.5 |
| 1.1195 | B.185 | C.5 |
| 1.1196 | B.186 | C.5 |
| 1.1197 | B.187 | C.5 |
| 1.1198 | B.188 | C.5 |
| 1.1199 | B.189 | C.5 |
| 1.1200 | B.190 | C.5 |
| 1.1201 | B.191 | C.5 |
| 1.1202 | B.192 | C.5 |
| 1.1203 | B.193 | C.5 |
| 1.1204 | B.194 | C.5 |
| 1.1205 | B.195 | C.5 |
| 1.1206 | B.196 | C.5 |
| 1.1207 | B.197 | C.5 |
| 1.1208 | B.198 | C.5 |
| 1.1209 | B.199 | C.5 |
| 1.1210 | B.200 | C.5 |
| 1.1211 | B.201 | C.5 |
| 1.1212 | B.202 | C.5 |
| 1.1213 | B.1 | C.6 |
| 1.1214 | B.2 | C.6 |
| 1.1215 | B.3 | C.6 |
| 1.1216 | B.4 | C.6 |
| 1.1217 | B.5 | C.6 |
| 1.1218 | B.6 | C.6 |
| 1.1219 | B.7 | C.6 |
| 1.1220 | B.8 | C.6 |
| 1.1221 | B.9 | C.6 |
| 1.1222 | B.10 | C.6 |
| 1.1223 | B.11 | C.6 |
| 1.1224 | B.12 | C.6 |
| 1.1225 | B.13 | C.6 |
| 1.1226 | B.14 | C.6 |
| 1.1227 | B.15 | C.6 |
| 1.1228 | B.16 | C.6 |
| 1.1229 | B.17 | C.6 |
| 1.1230 | B.18 | C.6 |
| 1.1231 | B.19 | C.6 |
| 1.1232 | B.20 | C.6 |
| 1.1233 | B.21 | C.6 |
| 1.1234 | B.22 | C.6 |
| 1.1235 | B.23 | C.6 |
| 1.1236 | B.24 | C.6 |
| 1.1237 | B.25 | C.6 |
| 1.1238 | B.26 | C.6 |
| 1.1239 | B.27 | C.6 |
| 1.1240 | B.28 | C.6 |
| 1.1241 | B.29 | C.6 |
| 1.1242 | B.30 | C.6 |
| 1.1243 | B.31 | C.6 |
| 1.1244 | B.32 | C.6 |
| 1.1245 | B.33 | C.6 |
| 1.1246 | B.34 | C.6 |
| 1.1247 | B.35 | C.6 |
| 1.1248 | B.36 | C.6 |
| 1.1249 | B.37 | C.6 |
| 1.1250 | B.38 | C.6 |
| 1.1251 | B.39 | C.6 |
| 1.1252 | B.40 | C.6 |
| 1.1253 | B.41 | C.6 |
| 1.1254 | B.42 | C.6 |
| 1.1255 | B.43 | C.6 |
| 1.1256 | B.44 | C.6 |
| 1.1257 | B.45 | C.6 |
| 1.1258 | B.46 | C.6 |
| 1.1259 | B.47 | C.6 |
| 1.1260 | B.48 | C.6 |
| 1.1261 | B.49 | C.6 |
| 1.1262 | B.50 | C.6 |
| 1.1263 | B.51 | C.6 |
| 1.1264 | B.52 | C.6 |
| 1.1265 | B.53 | C.6 |
| 1.1266 | B.54 | C.6 |
| 1.1267 | B.55 | C.6 |
| 1.1268 | B.56 | C.6 |
| 1.1269 | B.57 | C.6 |
| 1.1270 | B.58. | C.6 |
| 1.1271 | B.59 | C.6 |
| 1.1272 | B.60 | C.6 |
| 1.1273 | B.61 | C.6 |
| 1.1274 | B.62 | C.6 |
| 1.1275 | B.63 | C.6 |
| 1.1276 | B.64 | C.6 |
| 1.1277 | B.65 | C.6 |

TABLE 1-continued (compositions 1.1 to 1.3653):

| comp. no. | herbicide B | safener C |
|---|---|---|
| 1.1278 | B.66 | C.6 |
| 1.1279 | B.67 | C.6 |
| 1.1280 | B.68 | C.6 |
| 1.1281 | B.69 | C.6 |
| 1.1282 | B.70 | C.6 |
| 1.1283 | B.71 | C.6 |
| 1.1284 | B.72 | C.6 |
| 1.1285 | B.73 | C.6 |
| 1.1286 | B.74 | C.6 |
| 1.1287 | B.75 | C.6 |
| 1.1288 | B.76 | C.6 |
| 1.1289 | B.77 | C.6 |
| 1.1290 | B.78 | C.6 |
| 1.1291 | B.79 | C.6 |
| 1.1292 | B.80 | C.6 |
| 1.1293 | B.81 | C.6 |
| 1.1294 | B.82 | C.6 |
| 1.1295 | B.83 | C.6 |
| 1.1296 | B.84 | C.6 |
| 1.1297 | B.85 | C.6 |
| 1.1298 | B.86 | C.6 |
| 1.1299 | B.87 | C.6 |
| 1.1300 | B.88 | C.6 |
| 1.1301 | B.89 | C.6 |
| 1.1302 | B.90 | C.6 |
| 1.1303 | B.91 | C.6 |
| 1.1304 | B.92 | C.6 |
| 1.1305 | B.93 | C.6 |
| 1.1306 | B.94 | C.6 |
| 1.1307 | B.95 | C.6 |
| 1.1308 | B.96 | C.6 |
| 1.1309 | B.97 | C.6 |
| 1.1310 | B.98 | C.6 |
| 1.1311 | B.99 | C.6 |
| 1.1312 | B.100 | C.6 |
| 1.1313 | B.101 | C.6 |
| 1.1314 | B.102 | C.6 |
| 1.1315 | B.103 | C.6 |
| 1.1316 | B.104 | C.6 |
| 1.1317 | B.105 | C.6 |
| 1.1318 | B.106 | C.6 |
| 1.1319 | B.107 | C.6 |
| 1.1320 | B.108 | C.6 |
| 1.1321 | B.109 | C.6 |
| 1.1322 | B.110 | C.6 |
| 1.1323 | B.111 | C.6 |
| 1.1324 | B.112 | C.6 |
| 1.1325 | B.113 | C.6 |
| 1.1326 | B.114 | C.6 |
| 1.1327 | B.115 | C.6 |
| 1.1328 | B.116 | C.6 |
| 1.1329 | B.117 | C.6 |
| 1.1330 | B.118 | C.6 |
| 1.1331 | B.119 | C.6 |
| 1.1332 | B.120 | C.6 |
| 1.1333 | B.121 | C.6 |
| 1.1334 | B.122 | C.6 |
| 1.1335 | B.123 | C.6 |
| 1.1336 | B.124 | C.6 |
| 1.1337 | B.125 | C.6 |
| 1.1338 | B.126 | C.6 |
| 1.1339 | B.127 | C.6 |
| 1.1340 | B.128 | C.6 |
| 1.1341 | B.129 | C.6 |
| 1.1342 | B.130 | C.6 |
| 1.1343 | B.131 | C.6 |
| 1.1344 | B.132 | C.6 |
| 1.1345 | B.133 | C.6 |
| 1.1346 | B.134 | C.6 |
| 1.1347 | B.135 | C.6 |
| 1.1348 | B.136 | C.6 |
| 1.1349 | B.137 | C.6 |
| 1.1350 | B.138 | C.6 |
| 1.1351 | B.139 | C.6 |
| 1.1352 | B.140 | C.6 |
| 1.1353 | B.141 | C.6 |
| 1.1354 | B.142 | C.6 |
| 1.1355 | B.143 | C.6 |
| 1.1356 | B.144 | C.6 |
| 1.1357 | B.145 | C.6 |
| 1.1358 | B.146 | C.6 |
| 1.1359 | B.147 | C.6 |
| 1.1360 | B.148 | C.6 |
| 1.1361 | B.149 | C.6 |
| 1.1362 | B.150 | C.6 |
| 1.1363 | B.151 | C.6 |
| 1.1364 | B.152 | C.6 |
| 1.1365 | B.153 | C.6 |
| 1.1366 | B.154 | C.6 |
| 1.1367 | B.155 | C.6 |
| 1.1368 | B.156 | C.6 |
| 1.1369 | B.157 | C.6 |
| 1.1370 | B.158 | C.6 |
| 1.1371 | B.159 | C.6 |
| 1.1372 | B.160 | C.6 |
| 1.1373 | B.161 | C.6 |
| 1.1374 | B.162 | C.6 |
| 1.1375 | B.163 | C.6 |
| 1.1376 | B.164 | C.6 |
| 1.1377 | B.165 | C.6 |
| 1.1378 | B.166 | C.6 |
| 1.1379 | B.167 | C.6 |
| 1.1380 | B.168 | C.6 |
| 1.1381 | B.169 | C.6 |
| 1.1382 | B.170 | C.6 |
| 1.1383 | B.171 | C.6 |
| 1.1384 | B.172 | C.6 |
| 1.1385 | B.173 | C.6 |
| 1.1386 | B.174 | C.6 |
| 1.1387 | B.175 | C.6 |
| 1.1388 | B.176 | C.6 |
| 1.1389 | B.177 | C.6 |
| 1.1390 | B.178 | C.6 |
| 1.1391 | B.179 | C.6 |
| 1.1392 | B.180 | C.6 |
| 1.1393 | B.181 | C.6 |
| 1.1394 | B.182 | C.6 |
| 1.1395 | B.183 | C.6 |
| 1.1396 | B.184 | C.6 |
| 1.1397 | B.185 | C.6 |
| 1.1398 | B.186 | C.6 |
| 1.1399 | B.187 | C.6 |
| 1.1400 | B.188 | C.6 |
| 1.1401 | B.189 | C.6 |
| 1.1402 | B.190 | C.6 |
| 1.1403 | B.191 | C.6 |
| 1.1404 | B.192 | C.6 |
| 1.1405 | B.193 | C.6 |
| 1.1406 | B.194 | C.6 |
| 1.1407 | B.195 | C.6 |
| 1.1408 | B.196 | C.6 |
| 1.1409 | B.197 | C.6 |
| 1.1410 | B.198 | C.6 |
| 1.1411 | B.199 | C.6 |
| 1.1412 | B.200 | C.6 |
| 1.1413 | B.201 | C.6 |
| 1.1414 | B.202 | C.6 |
| 1.1415 | B.1 | C.7 |
| 1.1416 | B.2 | C.7 |
| 1.1417 | B.3 | C.7 |
| 1.1418 | B.4 | C.7 |
| 1.1419 | B.5 | C.7 |
| 1.1420 | B.6 | C.7 |
| 1.1421 | B.7 | C.7 |
| 1.1422 | B.8 | C.7 |
| 1.1423 | B.9 | C.7 |
| 1.1424 | B.10 | C.7 |
| 1.1425 | B.11 | C.7 |
| 1.1426 | B.12 | C.7 |
| 1.1427 | B.13 | C.7 |

TABLE 1-continued (compositions 1.1 to 1.3653):

| comp. no. | herbicide B | safener C |
|---|---|---|
| 1.1428 | B.14 | C.7 |
| 1.1429 | B.15 | C.7 |
| 1.1430 | B.16 | C.7 |
| 1.1431 | B.17 | C.7 |
| 1.1432 | B.18 | C.7 |
| 1.1433 | B.19 | C.7 |
| 1.1434 | B.20 | C.7 |
| 1.1435 | B.21 | C.7 |
| 1.1436 | B.22 | C.7 |
| 1.1437 | B.23 | C.7 |
| 1.1438 | B.24 | C.7 |
| 1.1439 | B.25 | C.7 |
| 1.1440 | B.26 | C.7 |
| 1.1441 | B.27 | C.7 |
| 1.1442 | B.28 | C.7 |
| 1.1443 | B.29 | C.7 |
| 1.1444 | B.30 | C.7 |
| 1.1445 | B.31 | C.7 |
| 1.1446 | B.32 | C.7 |
| 1.1447 | B.33 | C.7 |
| 1.1448 | B.34 | C.7 |
| 1.1449 | B.35 | C.7 |
| 1.1450 | B.36 | C.7 |
| 1.1451 | B.37 | C.7 |
| 1.1452 | B.38 | C.7 |
| 1.1453 | B.39 | C.7 |
| 1.1454 | B.40 | C.7 |
| 1.1455 | B.41 | C.7 |
| 1.1456 | B.42 | C.7 |
| 1.1457 | B.43 | C.7 |
| 1.1458 | B.44 | C.7 |
| 1.1459 | B.45 | C.7 |
| 1.1460 | B.46 | C.7 |
| 1.1461 | B.47 | C.7 |
| 1.1462 | B.48 | C.7 |
| 1.1463 | B.49 | C.7 |
| 1.1464 | B.50 | C.7 |
| 1.1465 | B.51 | C.7 |
| 1.1466 | B.52 | C.7 |
| 1.1467 | B.53 | C.7 |
| 1.1468 | B.54 | C.7 |
| 1.1469 | B.55 | C.7 |
| 1.1470 | B.56 | C.7 |
| 1.1471 | B.57 | C.7 |
| 1.1472 | B.58. | C.7 |
| 1.1473 | B.59 | C.7 |
| 1.1474 | B.60 | C.7 |
| 1.1475 | B.61 | C.7 |
| 1.1476 | B.62 | C.7 |
| 1.1477 | B.63 | C.7 |
| 1.1478 | B.64 | C.7 |
| 1.1479 | B.65 | C.7 |
| 1.1480 | B.66 | C.7 |
| 1.1481 | B.67 | C.7 |
| 1.1482 | B.68 | C.7 |
| 1.1483 | B.69 | C.7 |
| 1.1484 | B.70 | C.7 |
| 1.1485 | B.71 | C.7 |
| 1.1486 | B.72 | C.7 |
| 1.1487 | B.73 | C.7 |
| 1.1488 | B.74 | C.7 |
| 1.1489 | B.75 | C.7 |
| 1.1490 | B.76 | C.7 |
| 1.1491 | B.77 | C.7 |
| 1.1492 | B.78 | C.7 |
| 1.1493 | B.79 | C.7 |
| 1.1494 | B.80 | C.7 |
| 1.1495 | B.81 | C.7 |
| 1.1496 | B.82 | C.7 |
| 1.1497 | B.83 | C.7 |
| 1.1498 | B.84 | C.7 |
| 1.1499 | B.85 | C.7 |
| 1.1500 | B.86 | C.7 |
| 1.1501 | B.87 | C.7 |
| 1.1502 | B.88 | C.7 |
| 1.1503 | B.89 | C.7 |
| 1.1504 | B.90 | C.7 |
| 1.1505 | B.91 | C.7 |
| 1.1506 | B.92 | C.7 |
| 1.1507 | B.93 | C.7 |
| 1.1508 | B.94 | C.7 |
| 1.1509 | B.95 | C.7 |
| 1.1510 | B.96 | C.7 |
| 1.1511 | B.97 | C.7 |
| 1.1512 | B.98 | C.7 |
| 1.1513 | B.99 | C.7 |
| 1.1514 | B.100 | C.7 |
| 1.1515 | B.101 | C.7 |
| 1.1516 | B.102 | C.7 |
| 1.1517 | B.103 | C.7 |
| 1.1518 | B.104 | C.7 |
| 1.1519 | B.105 | C.7 |
| 1.1520 | B.106 | C.7 |
| 1.1521 | B.107 | C.7 |
| 1.1522 | B.108 | C.7 |
| 1.1523 | B.109 | C.7 |
| 1.1524 | B.110 | C.7 |
| 1.1525 | B.111 | C.7 |
| 1.1526 | B.112 | C.7 |
| 1.1527 | B.113 | C.7 |
| 1.1528 | B.114 | C.7 |
| 1.1529 | B.115 | C.7 |
| 1.1530 | B.116 | C.7 |
| 1.1531 | B.117 | C.7 |
| 1.1532 | B.118 | C.7 |
| 1.1533 | B.119 | C.7 |
| 1.1534 | B.120 | C.7 |
| 1.1535 | B.121 | C.7 |
| 1.1536 | B.122 | C.7 |
| 1.1537 | B.123 | C.7 |
| 1.1538 | B.124 | C.7 |
| 1.1539 | B.125 | C.7 |
| 1.1540 | B.126 | C.7 |
| 1.1541 | B.127 | C.7 |
| 1.1542 | B.128 | C.7 |
| 1.1543 | B.129 | C.7 |
| 1.1544 | B.130 | C.7 |
| 1.1545 | B.131 | C.7 |
| 1.1546 | B.132 | C.7 |
| 1.1547 | B.133 | C.7 |
| 1.1548 | B.134 | C.7 |
| 1.1549 | B.135 | C.7 |
| 1.1550 | B.136 | C.7 |
| 1.1551 | B.137 | C.7 |
| 1.1552 | B.138 | C.7 |
| 1.1553 | B.139 | C.7 |
| 1.1554 | B.140 | C.7 |
| 1.1555 | B.141 | C.7 |
| 1.1556 | B.142 | C.7 |
| 1.1557 | B.143 | C.7 |
| 1.1558 | B.144 | C.7 |
| 1.1559 | B.145 | C.7 |
| 1.1560 | B.146 | C.7 |
| 1.1561 | B.147 | C.7 |
| 1.1562 | B.148 | C.7 |
| 1.1563 | B.149 | C.7 |
| 1.1564 | B.150 | C.7 |
| 1.1565 | B.151 | C.7 |
| 1.1566 | B.152 | C.7 |
| 1.1567 | B.153 | C.7 |
| 1.1568 | B.154 | C.7 |
| 1.1569 | B.155 | C.7 |
| 1.1570 | B.156 | C.7 |
| 1.1571 | B.157 | C.7 |
| 1.1572 | B.158 | C.7 |
| 1.1573 | B.159 | C.7 |
| 1.1574 | B.160 | C.7 |
| 1.1575 | B.161 | C.7 |
| 1.1576 | B.162 | C.7 |
| 1.1577 | B.163 | C.7 |

TABLE 1-continued (compositions 1.1 to 1.3653):

| comp. no. | herbicide B | safener C |
|---|---|---|
| 1.1578 | B.164 | C.7 |
| 1.1579 | B.165 | C.7 |
| 1.1580 | B.166 | C.7 |
| 1.1581 | B.167 | C.7 |
| 1.1582 | B.168 | C.7 |
| 1.1583 | B.169 | C.7 |
| 1.1584 | B.170 | C.7 |
| 1.1585 | B.171 | C.7 |
| 1.1586 | B.172 | C.7 |
| 1.1587 | B.173 | C.7 |
| 1.1588 | B.174 | C.7 |
| 1.1589 | B.175 | C.7 |
| 1.1590 | B.176 | C.7 |
| 1.1591 | B.177 | C.7 |
| 1.1592 | B.178 | C.7 |
| 1.1593 | B.179 | C.7 |
| 1.1594 | B.180 | C.7 |
| 1.1595 | B.181 | C.7 |
| 1.1596 | B.182 | C.7 |
| 1.1597 | B.183 | C.7 |
| 1.1598 | B.184 | C.7 |
| 1.1599 | B.185 | C.7 |
| 1.1600 | B.186 | C.7 |
| 1.1601 | B.187 | C.7 |
| 1.1602 | B.188 | C.7 |
| 1.1603 | B.189 | C.7 |
| 1.1604 | B.190 | C.7 |
| 1.1605 | B.191 | C.7 |
| 1.1606 | B.192 | C.7 |
| 1.1607 | B.193 | C.7 |
| 1.1608 | B.194 | C.7 |
| 1.1609 | B.195 | C.7 |
| 1.1610 | B.196 | C.7 |
| 1.1611 | B.197 | C.7 |
| 1.1612 | B.198 | C.7 |
| 1.1613 | B.199 | C.7 |
| 1.1614 | B.200 | C.7 |
| 1.1615 | B.201 | C.7 |
| 1.1616 | B.202 | C.7 |
| 1.1617 | B.1 | C.8 |
| 1.1618 | B.2 | C.8 |
| 1.1619 | B.3 | C.8 |
| 1.1620 | B.4 | C.8 |
| 1.1621 | B.5 | C.8 |
| 1.1622 | B.6 | C.8 |
| 1.1623 | B.7 | C.8 |
| 1.1624 | B.8 | C.8 |
| 1.1625 | B.9 | C.8 |
| 1.1626 | B.10 | C.8 |
| 1.1627 | B.11 | C.8 |
| 1.1628 | B.12 | C.8 |
| 1.1629 | B.13 | C.8 |
| 1.1630 | B.14 | C.8 |
| 1.1631 | B.15 | C.8 |
| 1.1632 | B.16 | C.8 |
| 1.1633 | B.17 | C.8 |
| 1.1634 | B.18 | C.8 |
| 1.1635 | B.19 | C.8 |
| 1.1636 | B.20 | C.8 |
| 1.1637 | B.21 | C.8 |
| 1.1638 | B.22 | C.8 |
| 1.1639 | B.23 | C.8 |
| 1.1640 | B.24 | C.8 |
| 1.1641 | B.25 | C.8 |
| 1.1642 | B.26 | C.8 |
| 1.1643 | B.27 | C.8 |
| 1.1644 | B.28 | C.8 |
| 1.1645 | B.29 | C.8 |
| 1.1646 | B.30 | C.8 |
| 1.1647 | B.31 | C.8 |
| 1.1648 | B.32 | C.8 |
| 1.1649 | B.33 | C.8 |
| 1.1650 | B.34 | C.8 |
| 1.1651 | B.35 | C.8 |
| 1.1652 | B.36 | C.8 |
| 1.1653 | B.37 | C.8 |
| 1.1654 | B.38 | C.8 |
| 1.1655 | B.39 | C.8 |
| 1.1656 | B.40 | C.8 |
| 1.1657 | B.41 | C.8 |
| 1.1658 | B.42 | C.8 |
| 1.1659 | B.43 | C.8 |
| 1.1660 | B.44 | C.8 |
| 1.1661 | B.45 | C.8 |
| 1.1662 | B.46 | C.8 |
| 1.1663 | B.47 | C.8 |
| 1.1664 | B.48 | C.8 |
| 1.1665 | B.49 | C.8 |
| 1.1666 | B.50 | C.8 |
| 1.1667 | B.51 | C.8 |
| 1.1668 | B.52 | C.8 |
| 1.1669 | B.53 | C.8 |
| 1.1670 | B.54 | C.8 |
| 1.1671 | B.55 | C.8 |
| 1.1672 | B.56 | C.8 |
| 1.1673 | B.57 | C.8 |
| 1.1674 | B.58. | C.8 |
| 1.1675 | B.59 | C.8 |
| 1.1676 | B.60 | C.8 |
| 1.1677 | B.61 | C.8 |
| 1.1678 | B.62 | C.8 |
| 1.1679 | B.63 | C.8 |
| 1.1680 | B.64 | C.8 |
| 1.1681 | B.65 | C.8 |
| 1.1682 | B.66 | C.8 |
| 1.1683 | B.67 | C.8 |
| 1.1684 | B.68 | C.8 |
| 1.1685 | B.69 | C.8 |
| 1.1686 | B.70 | C.8 |
| 1.1687 | B.71 | C.8 |
| 1.1688 | B.72 | C.8 |
| 1.1689 | B.73 | C.8 |
| 1.1690 | B.74 | C.8 |
| 1.1691 | B.75 | C.8 |
| 1.1692 | B.76 | C.8 |
| 1.1693 | B.77 | C.8 |
| 1.1694 | B.78 | C.8 |
| 1.1695 | B.79 | C.8 |
| 1.1696 | B.80 | C.8 |
| 1.1697 | B.81 | C.8 |
| 1.1698 | B.82 | C.8 |
| 1.1699 | B.83 | C.8 |
| 1.1700 | B.84 | C.8 |
| 1.1701 | B.85 | C.8 |
| 1.1702 | B.86 | C.8 |
| 1.1703 | B.87 | C.8 |
| 1.1704 | B.88 | C.8 |
| 1.1705 | B.89 | C.8 |
| 1.1706 | B.90 | C.8 |
| 1.1707 | B.91 | C.8 |
| 1.1708 | B.92 | C.8 |
| 1.1709 | B.93 | C.8 |
| 1.1710 | B.94 | C.8 |
| 1.1711 | B.95 | C.8 |
| 1.1712 | B.96 | C.8 |
| 1.1713 | B.97 | C.8 |
| 1.1714 | B.98 | C.8 |
| 1.1715 | B.99 | C.8 |
| 1.1716 | B.100 | C.8 |
| 1.1717 | B.101 | C.8 |
| 1.1718 | B.102 | C.8 |
| 1.1719 | B.103 | C.8 |
| 1.1720 | B.104 | C.8 |
| 1.1721 | B.105 | C.8 |
| 1.1722 | B.106 | C.8 |
| 1.1723 | B.107 | C.8 |
| 1.1724 | B.108 | C.8 |
| 1.1725 | B.109 | C.8 |
| 1.1726 | B.110 | C.8 |
| 1.1727 | B.111 | C.8 |

TABLE 1-continued (compositions 1.1 to 1.3653):

| comp. no. | herbicide B | safener C |
|---|---|---|
| 1.1728 | B.112 | C.8 |
| 1.1729 | B.113 | C.8 |
| 1.1730 | B.114 | C.8 |
| 1.1731 | B.115 | C.8 |
| 1.1732 | B.116 | C.8 |
| 1.1733 | B.117 | C.8 |
| 1.1734 | B.118 | C.8 |
| 1.1735 | B.119 | C.8 |
| 1.1736 | B.120 | C.8 |
| 1.1737 | B.121 | C.8 |
| 1.1738 | B.122 | C.8 |
| 1.1739 | B.123 | C.8 |
| 1.1740 | B.124 | C.8 |
| 1.1741 | B.125 | C.8 |
| 1.1742 | B.126 | C.8 |
| 1.1743 | B.127 | C.8 |
| 1.1744 | B.128 | C.8 |
| 1.1745 | B.129 | C.8 |
| 1.1746 | B.130 | C.8 |
| 1.1747 | B.131 | C.8 |
| 1.1748 | B.132 | C.8 |
| 1.1749 | B.133 | C.8 |
| 1.1750 | B.134 | C.8 |
| 1.1751 | B.135 | C.8 |
| 1.1752 | B.136 | C.8 |
| 1.1753 | B.137 | C.8 |
| 1.1754 | B.138 | C.8 |
| 1.1755 | B.139 | C.8 |
| 1.1756 | B.140 | C.8 |
| 1.1757 | B.141 | C.8 |
| 1.1758 | B.142 | C.8 |
| 1.1759 | B.143 | C.8 |
| 1.1760 | B.144 | C.8 |
| 1.1761 | B.145 | C.8 |
| 1.1762 | B.146 | C.8 |
| 1.1763 | B.147 | C.8 |
| 1.1764 | B.148 | C.8 |
| 1.1765 | B.149 | C.8 |
| 1.1766 | B.150 | C.8 |
| 1.1767 | B.151 | C.8 |
| 1.1768 | B.152 | C.8 |
| 1.1769 | B.153 | C.8 |
| 1.1770 | B.154 | C.8 |
| 1.1771 | B.155 | C.8 |
| 1.1772 | B.156 | C.8 |
| 1.1773 | B.157 | C.8 |
| 1.1774 | B.158 | C.8 |
| 1.1775 | B.159 | C.8 |
| 1.1776 | B.160 | C.8 |
| 1.1777 | B.161 | C.8 |
| 1.1778 | B.162 | C.8 |
| 1.1779 | B.163 | C.8 |
| 1.1780 | B.164 | C.8 |
| 1.1781 | B.165 | C.8 |
| 1.1782 | B.166 | C.8 |
| 1.1783 | B.167 | C.8 |
| 1.1784 | B.168 | C.8 |
| 1.1785 | B.169 | C.8 |
| 1.1786 | B.170 | C.8 |
| 1.1787 | B.171 | C.8 |
| 1.1788 | B.172 | C.8 |
| 1.1789 | B.173 | C.8 |
| 1.1790 | B.174 | C.8 |
| 1.1791 | B.175 | C.8 |
| 1.1792 | B.176 | C.8 |
| 1.1793 | B.177 | C.8 |
| 1.1794 | B.178 | C.8 |
| 1.1795 | B.179 | C.8 |
| 1.1796 | B.180 | C.8 |
| 1.1797 | B.181 | C.8 |
| 1.1798 | B.182 | C.8 |
| 1.1799 | B.183 | C.8 |
| 1.1800 | B.184 | C.8 |
| 1.1801 | B.185 | C.8 |
| 1.1802 | B.186 | C.8 |
| 1.1803 | B.187 | C.8 |
| 1.1804 | B.188 | C.8 |
| 1.1805 | B.189 | C.8 |
| 1.1806 | B.190 | C.8 |
| 1.1807 | B.191 | C.8 |
| 1.1808 | B.192 | C.8 |
| 1.1809 | B.193 | C.8 |
| 1.1810 | B.194 | C.8 |
| 1.1811 | B.195 | C.8 |
| 1.1812 | B.196 | C.8 |
| 1.1813 | B.197 | C.8 |
| 1.1814 | B.198 | C.8 |
| 1.1815 | B.199 | C.8 |
| 1.1816 | B.200 | C.8 |
| 1.1817 | B.201 | C.8 |
| 1.1818 | B.202 | C.8 |
| 1.1819 | B.1 | C.9 |
| 1.1820 | B.2 | C.9 |
| 1.1821 | B.3 | C.9 |
| 1.1822 | B.4 | C.9 |
| 1.1823 | B.5 | C.9 |
| 1.1824 | B.6 | C.9 |
| 1.1825 | B.7 | C.9 |
| 1.1826 | B.8 | C.9 |
| 1.1827 | B.9 | C.9 |
| 1.1828 | B.10 | C.9 |
| 1.1829 | B.11 | C.9 |
| 1.1830 | B.12 | C.9 |
| 1.1831 | B.13 | C.9 |
| 1.1832 | B.14 | C.9 |
| 1.1833 | B.15 | C.9 |
| 1.1834 | B.16 | C.9 |
| 1.1835 | B.17 | C.9 |
| 1.1836 | B.18 | C.9 |
| 1.1837 | B.19 | C.9 |
| 1.1838 | B.20 | C.9 |
| 1.1839 | B.21 | C.9 |
| 1.1840 | B.22 | C.9 |
| 1.1841 | B.23 | C.9 |
| 1.1842 | B.24 | C.9 |
| 1.1843 | B.25 | C.9 |
| 1.1844 | B.26 | C.9 |
| 1.1845 | B.27 | C.9 |
| 1.1846 | B.28 | C.9 |
| 1.1847 | B.29 | C.9 |
| 1.1848 | B.30 | C.9 |
| 1.1849 | B.31 | C.9 |
| 1.1850 | B.32 | C.9 |
| 1.1851 | B.33 | C.9 |
| 1.1852 | B.34 | C.9 |
| 1.1853 | B.35 | C.9 |
| 1.1854 | B.36 | C.9 |
| 1.1855 | B.37 | C.9 |
| 1.1856 | B.38 | C.9 |
| 1.1857 | B.39 | C.9 |
| 1.1858 | B.40 | C.9 |
| 1.1859 | B.41 | C.9 |
| 1.1860 | B.42 | C.9 |
| 1.1861 | B.43 | C.9 |
| 1.1862 | B.44 | C.9 |
| 1.1863 | B.45 | C.9 |
| 1.1864 | B.46 | C.9 |
| 1.1865 | B.47 | C.9 |
| 1.1866 | B.48 | C.9 |
| 1.1867 | B.49 | C.9 |
| 1.1868 | B.50 | C.9 |
| 1.1869 | B.51 | C.9 |
| 1.1870 | B.52 | C.9 |
| 1.1871 | B.53 | C.9 |
| 1.1872 | B.54 | C.9 |
| 1.1873 | B.55 | C.9 |
| 1.1874 | B.56 | C.9 |
| 1.1875 | B.57 | C.9 |
| 1.1876 | B.58. | C.9 |
| 1.1877 | B.59 | C.9 |

TABLE 1-continued (compositions 1.1 to 1.3653):

| comp. no. | herbicide B | safener C |
|---|---|---|
| 1.1878 | B.60 | C.9 |
| 1.1879 | B.61 | C.9 |
| 1.1880 | B.62 | C.9 |
| 1.1881 | B.63 | C.9 |
| 1.1882 | B.64 | C.9 |
| 1.1883 | B.65 | C.9 |
| 1.1884 | B.66 | C.9 |
| 1.1885 | B.67 | C.9 |
| 1.1886 | B.68 | C.9 |
| 1.1887 | B.69 | C.9 |
| 1.1888 | B.70 | C.9 |
| 1.1889 | B.71 | C.9 |
| 1.1890 | B.72 | C.9 |
| 1.1891 | B.73 | C.9 |
| 1.1892 | B.74 | C.9 |
| 1.1893 | B.75 | C.9 |
| 1.1894 | B.76 | C.9 |
| 1.1895 | B.77 | C.9 |
| 1.1896 | B.78 | C.9 |
| 1.1897 | B.79 | C.9 |
| 1.1898 | B.80 | C.9 |
| 1.1899 | B.81 | C.9 |
| 1.1900 | B.82 | C.9 |
| 1.1901 | B.83 | C.9 |
| 1.1902 | B.84 | C.9 |
| 1.1903 | B.85 | C.9 |
| 1.1904 | B.86 | C.9 |
| 1.1905 | B.87 | C.9 |
| 1.1906 | B.88 | C.9 |
| 1.1907 | B.89 | C.9 |
| 1.1908 | B.90 | C.9 |
| 1.1909 | B.91 | C.9 |
| 1.1910 | B.92 | C.9 |
| 1.1911 | B.93 | C.9 |
| 1.1912 | B.94 | C.9 |
| 1.1913 | B.95 | C.9 |
| 1.1914 | B.96 | C.9 |
| 1.1915 | B.97 | C.9 |
| 1.1916 | B.98 | C.9 |
| 1.1917 | B.99 | C.9 |
| 1.1918 | B.100 | C.9 |
| 1.1919 | B.101 | C.9 |
| 1.1920 | B.102 | C.9 |
| 1.1921 | B.103 | C.9 |
| 1.1922 | B.104 | C.9 |
| 1.1923 | B.105 | C.9 |
| 1.1924 | B.106 | C.9 |
| 1.1925 | B.107 | C.9 |
| 1.1926 | B.108 | C.9 |
| 1.1927 | B.109 | C.9 |
| 1.1928 | B.110 | C.9 |
| 1.1929 | B.111 | C.9 |
| 1.1930 | B.112 | C.9 |
| 1.1931 | B.113 | C.9 |
| 1.1932 | B.114 | C.9 |
| 1.1933 | B.115 | C.9 |
| 1.1934 | B.116 | C.9 |
| 1.1935 | B.117 | C.9 |
| 1.1936 | B.118 | C.9 |
| 1.1937 | B.119 | C.9 |
| 1.1938 | B.120 | C.9 |
| 1.1939 | B.121 | C.9 |
| 1.1940 | B.122 | C.9 |
| 1.1941 | B.123 | C.9 |
| 1.1942 | B.124 | C.9 |
| 1.1943 | B.125 | C.9 |
| 1.1944 | B.126 | C.9 |
| 1.1945 | B.127 | C.9 |
| 1.1946 | B.128 | C.9 |
| 1.1947 | B.129 | C.9 |
| 1.1948 | B.130 | C.9 |
| 1.1949 | B.131 | C.9 |
| 1.1950 | B.132 | C.9 |
| 1.1951 | B.133 | C.9 |
| 1.1952 | B.134 | C.9 |
| 1.1953 | B.135 | C.9 |
| 1.1954 | B.136 | C.9 |
| 1.1955 | B.137 | C.9 |
| 1.1956 | B.138 | C.9 |
| 1.1957 | B.139 | C.9 |
| 1.1958 | B.140 | C.9 |
| 1.1959 | B.141 | C.9 |
| 1.1960 | B.142 | C.9 |
| 1.1961 | B.143 | C.9 |
| 1.1962 | B.144 | C.9 |
| 1.1963 | B.145 | C.9 |
| 1.1964 | B.146 | C.9 |
| 1.1965 | B.147 | C.9 |
| 1.1966 | B.148 | C.9 |
| 1.1967 | B.149 | C.9 |
| 1.1968 | B.150 | C.9 |
| 1.1969 | B.151 | C.9 |
| 1.1970 | B.152 | C.9 |
| 1.1971 | B.153 | C.9 |
| 1.1972 | B.154 | C.9 |
| 1.1973 | B.155 | C.9 |
| 1.1974 | B.156 | C.9 |
| 1.1975 | B.157 | C.9 |
| 1.1976 | B.158 | C.9 |
| 1.1977 | B.159 | C.9 |
| 1.1978 | B.160 | C.9 |
| 1.1979 | B.161 | C.9 |
| 1.1980 | B.162 | C.9 |
| 1.1981 | B.163 | C.9 |
| 1.1982 | B.164 | C.9 |
| 1.1983 | B.165 | C.9 |
| 1.1984 | B.166 | C.9 |
| 1.1985 | B.167 | C.9 |
| 1.1986 | B.168 | C.9 |
| 1.1987 | B.169 | C.9 |
| 1.1988 | B.170 | C.9 |
| 1.1989 | B.171 | C.9 |
| 1.1990 | B.172 | C.9 |
| 1.1991 | B.173 | C.9 |
| 1.1992 | B.174 | C.9 |
| 1.1993 | B.175 | C.9 |
| 1.1994 | B.176 | C.9 |
| 1.1995 | B.177 | C.9 |
| 1.1996 | B.178 | C.9 |
| 1.1997 | B.179 | C.9 |
| 1.1998 | B.180 | C.9 |
| 1.1999 | B.181 | C.9 |
| 1.2000 | B.182 | C.9 |
| 1.2001 | B.183 | C.9 |
| 1.2002 | B.184 | C.9 |
| 1.2003 | B.185 | C.9 |
| 1.2004 | B.186 | C.9 |
| 1.2005 | B.187 | C.9 |
| 1.2006 | B.188 | C.9 |
| 1.2007 | B.189 | C.9 |
| 1.2008 | B.190 | C.9 |
| 1.2009 | B.191 | C.9 |
| 1.2010 | B.192 | C.9 |
| 1.2011 | B.193 | C.9 |
| 1.2012 | B.194 | C.9 |
| 1.2013 | B.195 | C.9 |
| 1.2014 | B.196 | C.9 |
| 1.2015 | B.197 | C.9 |
| 1.2016 | B.198 | C.9 |
| 1.2017 | B.199 | C.9 |
| 1.2018 | B.200 | C.9 |
| 1.2019 | B.201 | C.9 |
| 1.2020 | B.202 | C.9 |
| 1.2021 | B.1 | C.10 |
| 1.2022 | B.2 | C.10 |
| 1.2023 | B.3 | C.10 |
| 1.2024 | B.4 | C.10 |
| 1.2025 | B.5 | C.10 |
| 1.2026 | B.6 | C.10 |
| 1.2027 | B.7 | C.10 |

TABLE 1-continued (compositions 1.1 to 1.3653):

| comp. no. | herbicide B | safener C |
|---|---|---|
| 1.2028 | B.8 | C.10 |
| 1.2029 | B.9 | C.10 |
| 1.2030 | B.10 | C.10 |
| 1.2031 | B.11 | C.10 |
| 1.2032 | B.12 | C.10 |
| 1.2033 | B.13 | C.10 |
| 1.2034 | B.14 | C.10 |
| 1.2035 | B.15 | C.10 |
| 1.2036 | B.16 | C.10 |
| 1.2037 | B.17 | C.10 |
| 1.2038 | B.18 | C.10 |
| 1.2039 | B.19 | C.10 |
| 1.2040 | B.20 | C.10 |
| 1.2041 | B.21 | C.10 |
| 1.2042 | B.22 | C.10 |
| 1.2043 | B.23 | C.10 |
| 1.2044 | B.24 | C.10 |
| 1.2045 | B.25 | C.10 |
| 1.2046 | B.26 | C.10 |
| 1.2047 | B.27 | C.10 |
| 1.2048 | B.28 | C.10 |
| 1.2049 | B.29 | C.10 |
| 1.2050 | B.30 | C.10 |
| 1.2051 | B.31 | C.10 |
| 1.2052 | B.32 | C.10 |
| 1.2053 | B.33 | C.10 |
| 1.2054 | B.34 | C.10 |
| 1.2055 | B.35 | C.10 |
| 1.2056 | B.36 | C.10 |
| 1.2057 | B.37 | C.10 |
| 1.2058 | B.38 | C.10 |
| 1.2059 | B.39 | C.10 |
| 1.2060 | B.40 | C.10 |
| 1.2061 | B.41 | C.10 |
| 1.2062 | B.42 | C.10 |
| 1.2063 | B.43 | C.10 |
| 1.2064 | B.44 | C.10 |
| 1.2065 | B.45 | C.10 |
| 1.2066 | B.46 | C.10 |
| 1.2067 | B.47 | C.10 |
| 1.2068 | B.48 | C.10 |
| 1.2069 | B.49 | C.10 |
| 1.2070 | B.50 | C.10 |
| 1.2071 | B.51 | C.10 |
| 1.2072 | B.52 | C.10 |
| 1.2073 | B.53 | C.10 |
| 1.2074 | B.54 | C.10 |
| 1.2075 | B.55 | C.10 |
| 1.2076 | B.56 | C.10 |
| 1.2077 | B.57 | C.10 |
| 1.2078 | B.58. | C.10 |
| 1.2079 | B.59 | C.10 |
| 1.2080 | B.60 | C.10 |
| 1.2081 | B.61 | C.10 |
| 1.2082 | B.62 | C.10 |
| 1.2083 | B.63 | C.10 |
| 1.2084 | B.64 | C.10 |
| 1.2085 | B.65 | C.10 |
| 1.2086 | B.66 | C.10 |
| 1.2087 | B.67 | C.10 |
| 1.2088 | B.68 | C.10 |
| 1.2089 | B.69 | C.10 |
| 1.2090 | B.70 | C.10 |
| 1.2091 | B.71 | C.10 |
| 1.2092 | B.72 | C.10 |
| 1.2093 | B.73 | C.10 |
| 1.2094 | B.74 | C.10 |
| 1.2095 | B.75 | C.10 |
| 1.2096 | B.76 | C.10 |
| 1.2097 | B.77 | C.10 |
| 1.2098 | B.78 | C.10 |
| 1.2099 | B.79 | C.10 |
| 1.2100 | B.80 | C.10 |
| 1.2101 | B.81 | C.10 |
| 1.2102 | B.82 | C.10 |
| 1.2103 | B.83 | C.10 |
| 1.2104 | B.84 | C.10 |
| 1.2105 | B.85 | C.10 |
| 1.2106 | B.86 | C.10 |
| 1.2107 | B.87 | C.10 |
| 1.2108 | B.88 | C.10 |
| 1.2109 | B.89 | C.10 |
| 1.2110 | B.90 | C.10 |
| 1.2111 | B.91 | C.10 |
| 1.2112 | B.92 | C.10 |
| 1.2113 | B.93 | C.10 |
| 1.2114 | B.94 | C.10 |
| 1.2115 | B.95 | C.10 |
| 1.2116 | B.96 | C.10 |
| 1.2117 | B.97 | C.10 |
| 1.2118 | B.98 | C.10 |
| 1.2119 | B.99 | C.10 |
| 1.2120 | B.100 | C.10 |
| 1.2121 | B.101 | C.10 |
| 1.2122 | B.102 | C.10 |
| 1.2123 | B.103 | C.10 |
| 1.2124 | B.104 | C.10 |
| 1.2125 | B.105 | C.10 |
| 1.2126 | B.106 | C.10 |
| 1.2127 | B.107 | C.10 |
| 1.2128 | B.108 | C.10 |
| 1.2129 | B.109 | C.10 |
| 1.2130 | B.110 | C.10 |
| 1.2131 | B.111 | C.10 |
| 1.2132 | B.112 | C.10 |
| 1.2133 | B.113 | C.10 |
| 1.2134 | B.114 | C.10 |
| 1.2135 | B.115 | C.10 |
| 1.2136 | B.116 | C.10 |
| 1.2137 | B.117 | C.10 |
| 1.2138 | B.118 | C.10 |
| 1.2139 | B.119 | C.10 |
| 1.2140 | B.120 | C.10 |
| 1.2141 | B.121 | C.10 |
| 1.2142 | B.122 | C.10 |
| 1.2143 | B.123 | C.10 |
| 1.2144 | B.124 | C.10 |
| 1.2145 | B.125 | C.10 |
| 1.2146 | B.126 | C.10 |
| 1.2147 | B.127 | C.10 |
| 1.2148 | B.128 | C.10 |
| 1.2149 | B.129 | C.10 |
| 1.2150 | B.130 | C.10 |
| 1.2151 | B.131 | C.10 |
| 1.2152 | B.132 | C.10 |
| 1.2153 | B.133 | C.10 |
| 1.2154 | B.134 | C.10 |
| 1.2155 | B.135 | C.10 |
| 1.2156 | B.136 | C.10 |
| 1.2157 | B.137 | C.10 |
| 1.2158 | B.138 | C.10 |
| 1.2159 | B.139 | C.10 |
| 1.2160 | B.140 | C.10 |
| 1.2161 | B.141 | C.10 |
| 1.2162 | B.142 | C.10 |
| 1.2163 | B.143 | C.10 |
| 1.2164 | B.144 | C.10 |
| 1.2165 | B.145 | C.10 |
| 1.2166 | B.146 | C.10 |
| 1.2167 | B.147 | C.10 |
| 1.2168 | B.148 | C.10 |
| 1.2169 | B.149 | C.10 |
| 1.2170 | B.150 | C.10 |
| 1.2171 | B.151 | C.10 |
| 1.2172 | B.152 | C.10 |
| 1.2173 | B.153 | C.10 |
| 1.2174 | B.154 | C.10 |
| 1.2175 | B.155 | C.10 |
| 1.2176 | B.156 | C.10 |
| 1.2177 | B.157 | C.10 |

TABLE 1-continued (compositions 1.1 to 1.3653):

| comp. no. | herbicide B | safener C |
|---|---|---|
| 1.2178 | B.158 | C.10 |
| 1.2179 | B.159 | C.10 |
| 1.2180 | B.160 | C.10 |
| 1.2181 | B.161 | C.10 |
| 1.2182 | B.162 | C.10 |
| 1.2183 | B.163 | C.10 |
| 1.2184 | B.164 | C.10 |
| 1.2185 | B.165 | C.10 |
| 1.2186 | B.166 | C.10 |
| 1.2187 | B.167 | C.10 |
| 1.2188 | B.168 | C.10 |
| 1.2189 | B.169 | C.10 |
| 1.2190 | B.170 | C.10 |
| 1.2191 | B.171 | C.10 |
| 1.2192 | B.172 | C.10 |
| 1.2193 | B.173 | C.10 |
| 1.2194 | B.174 | C.10 |
| 1.2195 | B.175 | C.10 |
| 1.2196 | B.176 | C.10 |
| 1.2197 | B.177 | C.10 |
| 1.2198 | B.178 | C.10 |
| 1.2199 | B.179 | C.10 |
| 1.2200 | B.180 | C.10 |
| 1.2201 | B.181 | C.10 |
| 1.2202 | B.182 | C.10 |
| 1.2203 | B.183 | C.10 |
| 1.2204 | B.184 | C.10 |
| 1.2205 | B.185 | C.10 |
| 1.2206 | B.186 | C.10 |
| 1.2207 | B.187 | C.10 |
| 1.2208 | B.188 | C.10 |
| 1.2209 | B.189 | C.10 |
| 1.2210 | B.190 | C.10 |
| 1.2211 | B.191 | C.10 |
| 1.2212 | B.192 | C.10 |
| 1.2213 | B.193 | C.10 |
| 1.2214 | B.194 | C.10 |
| 1.2215 | B.195 | C.10 |
| 1.2216 | B.196 | C.10 |
| 1.2217 | B.197 | C.10 |
| 1.2218 | B.198 | C.10 |
| 1.2219 | B.199 | C.10 |
| 1.2220 | B.200 | C.10 |
| 1.2221 | B.201 | C.10 |
| 1.2222 | B.202 | C.10 |
| 1.2223 | B.1 | C.11 |
| 1.2224 | B.2 | C.11 |
| 1.2225 | B.3 | C.11 |
| 1.2226 | B.4 | C.11 |
| 1.2227 | B.5 | C.11 |
| 1.2228 | B.6 | C.11 |
| 1.2229 | B.7 | C.11 |
| 1.2230 | B.8 | C.11 |
| 1.2231 | B.9 | C.11 |
| 1.2232 | B.10 | C.11 |
| 1.2233 | B.11 | C.11 |
| 1.2234 | B.12 | C.11 |
| 1.2235 | B.13 | C.11 |
| 1.2236 | B.14 | C.11 |
| 1.2237 | B.15 | C.11 |
| 1.2238 | B.16 | C.11 |
| 1.2239 | B.17 | C.11 |
| 1.2240 | B.18 | C.11 |
| 1.2241 | B.19 | C.11 |
| 1.2242 | B.20 | C.11 |
| 1.2243 | B.21 | C.11 |
| 1.2244 | B.22 | C.11 |
| 1.2245 | B.23 | C.11 |
| 1.2246 | B.24 | C.11 |
| 1.2247 | B.25 | C.11 |
| 1.2248 | B.26 | C.11 |
| 1.2249 | B.27 | C.11 |
| 1.2250 | B.28 | C.11 |
| 1.2251 | B.29 | C.11 |
| 1.2252 | B.30 | C.11 |
| 1.2253 | B.31 | C.11 |
| 1.2254 | B.32 | C.11 |
| 1.2255 | B.33 | C.11 |
| 1.2256 | B.34 | C.11 |
| 1.2257 | B.35 | C.11 |
| 1.2258 | B.36 | C.11 |
| 1.2259 | B.37 | C.11 |
| 1.2260 | B.38 | C.11 |
| 1.2261 | B.39 | C.11 |
| 1.2262 | B.40 | C.11 |
| 1.2263 | B.41 | C.11 |
| 1.2264 | B.42 | C.11 |
| 1.2265 | B.43 | C.11 |
| 1.2266 | B.44 | C.11 |
| 1.2267 | B.45 | C.11 |
| 1.2268 | B.46 | C.11 |
| 1.2269 | B.47 | C.11 |
| 1.2270 | B.48 | C.11 |
| 1.2271 | B.49 | C.11 |
| 1.2272 | B.50 | C.11 |
| 1.2273 | B.51 | C.11 |
| 1.2274 | B.52 | C.11 |
| 1.2275 | B.53 | C.11 |
| 1.2276 | B.54 | C.11 |
| 1.2277 | B.55 | C.11 |
| 1.2278 | B.56 | C.11 |
| 1.2279 | B.57 | C.11 |
| 1.2280 | B.58. | C.11 |
| 1.2281 | B.59 | C.11 |
| 1.2282 | B.60 | C.11 |
| 1.2283 | B.61 | C.11 |
| 1.2284 | B.62 | C.11 |
| 1.2285 | B.63 | C.11 |
| 1.2286 | B.64 | C.11 |
| 1.2287 | B.65 | C.11 |
| 1.2288 | B.66 | C.11 |
| 1.2289 | B.67 | C.11 |
| 1.2290 | B.68 | C.11 |
| 1.2291 | B.69 | C.11 |
| 1.2292 | B.70 | C.11 |
| 1.2293 | B.71 | C.11 |
| 1.2294 | B.72 | C.11 |
| 1.2295 | B.73 | C.11 |
| 1.2296 | B.74 | C.11 |
| 1.2297 | B.75 | C.11 |
| 1.2298 | B.76 | C.11 |
| 1.2299 | B.77 | C.11 |
| 1.2300 | B.78 | C.11 |
| 1.2301 | B.79 | C.11 |
| 1.2302 | B.80 | C.11 |
| 1.2303 | B.81 | C.11 |
| 1.2304 | B.82 | C.11 |
| 1.2305 | B.83 | C.11 |
| 1.2306 | B.84 | C.11 |
| 1.2307 | B.85 | C.11 |
| 1.2308 | B.86 | C.11 |
| 1.2309 | B.87 | C.11 |
| 1.2310 | B.88 | C.11 |
| 1.2311 | B.89 | C.11 |
| 1.2312 | B.90 | C.11 |
| 1.2313 | B.91 | C.11 |
| 1.2314 | B.92 | C.11 |
| 1.2315 | B.93 | C.11 |
| 1.2316 | B.94 | C.11 |
| 1.2317 | B.95 | C.11 |
| 1.2318 | B.96 | C.11 |
| 1.2319 | B.97 | C.11 |
| 1.2320 | B.98 | C.11 |
| 1.2321 | B.99 | C.11 |
| 1.2322 | B.100 | C.11 |
| 1.2323 | B.101 | C.11 |
| 1.2324 | B.102 | C.11 |
| 1.2325 | B.103 | C.11 |
| 1.2326 | B.104 | C.11 |
| 1.2327 | B.105 | C.11 |

TABLE 1-continued (compositions 1.1 to 1.3653):

| comp. no. | herbicide B | safener C |
|---|---|---|
| 1.2328 | B.106 | C.11 |
| 1.2329 | B.107 | C.11 |
| 1.2330 | B.108 | C.11 |
| 1.2331 | B.109 | C.11 |
| 1.2332 | B.110 | C.11 |
| 1.2333 | B.111 | C.11 |
| 1.2334 | B.112 | C.11 |
| 1.2335 | B.113 | C.11 |
| 1.2336 | B.114 | C.11 |
| 1.2337 | B.115 | C.11 |
| 1.2338 | B.116 | C.11 |
| 1.2339 | B.117 | C.11 |
| 1.2340 | B.118 | C.11 |
| 1.2341 | B.119 | C.11 |
| 1.2342 | B.120 | C.11 |
| 1.2343 | B.121 | C.11 |
| 1.2344 | B.122 | C.11 |
| 1.2345 | B.123 | C.11 |
| 1.2346 | B.124 | C.11 |
| 1.2347 | B.125 | C.11 |
| 1.2348 | B.126 | C.11 |
| 1.2349 | B.127 | C.11 |
| 1.2350 | B.128 | C.11 |
| 1.2351 | B.129 | C.11 |
| 1.2352 | B.130 | C.11 |
| 1.2353 | B.131 | C.11 |
| 1.2354 | B.132 | C.11 |
| 1.2355 | B.133 | C.11 |
| 1.2356 | B.134 | C.11 |
| 1.2357 | B.135 | C.11 |
| 1.2358 | B.136 | C.11 |
| 1.2359 | B.137 | C.11 |
| 1.2360 | B.138 | C.11 |
| 1.2361 | B.139 | C.11 |
| 1.2362 | B.140 | C.11 |
| 1.2363 | B.141 | C.11 |
| 1.2364 | B.142 | C.11 |
| 1.2365 | B.143 | C.11 |
| 1.2366 | B.144 | C.11 |
| 1.2367 | B.145 | C.11 |
| 1.2368 | B.146 | C.11 |
| 1.2369 | B.147 | C.11 |
| 1.2370 | B.148 | C.11 |
| 1.2371 | B.149 | C.11 |
| 1.2372 | B.150 | C.11 |
| 1.2373 | B.151 | C.11 |
| 1.2374 | B.152 | C.11 |
| 1.2375 | B.153 | C.11 |
| 1.2376 | B.154 | C.11 |
| 1.2377 | B.155 | C.11 |
| 1.2378 | B.156 | C.11 |
| 1.2379 | B.157 | C.11 |
| 1.2380 | B.158 | C.11 |
| 1.2381 | B.159 | C.11 |
| 1.2382 | B.160 | C.11 |
| 1.2383 | B.161 | C.11 |
| 1.2384 | B.162 | C.11 |
| 1.2385 | B.163 | C.11 |
| 1.2386 | B.164 | C.11 |
| 1.2387 | B.165 | C.11 |
| 1.2388 | B.166 | C.11 |
| 1.2389 | B.167 | C.11 |
| 1.2390 | B.168 | C.11 |
| 1.2391 | B.169 | C.11 |
| 1.2392 | B.170 | C.11 |
| 1.2393 | B.171 | C.11 |
| 1.2394 | B.172 | C.11 |
| 1.2395 | B.173 | C.11 |
| 1.2396 | B.174 | C.11 |
| 1.2397 | B.175 | C.11 |
| 1.2398 | B.176 | C.11 |
| 1.2399 | B.177 | C.11 |
| 1.2400 | B.178 | C.11 |
| 1.2401 | B.179 | C.11 |
| 1.2402 | B.180 | C.11 |
| 1.2403 | B.181 | C.11 |
| 1.2404 | B.182 | C.11 |
| 1.2405 | B.183 | C.11 |
| 1.2406 | B.184 | C.11 |
| 1.2407 | B.185 | C.11 |
| 1.2408 | B.186 | C.11 |
| 1.2409 | B.187 | C.11 |
| 1.2410 | B.188 | C.11 |
| 1.2411 | B.189 | C.11 |
| 1.2412 | B.190 | C.11 |
| 1.2413 | B.191 | C.11 |
| 1.2414 | B.192 | C.11 |
| 1.2415 | B.193 | C.11 |
| 1.2416 | B.194 | C.11 |
| 1.2417 | B.195 | C.11 |
| 1.2418 | B.196 | C.11 |
| 1.2419 | B.197 | C.11 |
| 1.2420 | B.198 | C.11 |
| 1.2421 | B.199 | C.11 |
| 1.2422 | B.200 | C.11 |
| 1.2423 | B.201 | C.11 |
| 1.2424 | B.202 | C.11 |
| 1.2425 | B.1 | C.12 |
| 1.2426 | B.2 | C.12 |
| 1.2427 | B.3 | C.12 |
| 1.2428 | B.4 | C.12 |
| 1.2429 | B.5 | C.12 |
| 1.2430 | B.6 | C.12 |
| 1.2431 | B.7 | C.12 |
| 1.2432 | B.8 | C.12 |
| 1.2433 | B.9 | C.12 |
| 1.2434 | B.10 | C.12 |
| 1.2435 | B.11 | C.12 |
| 1.2436 | B.12 | C.12 |
| 1.2437 | B.13 | C.12 |
| 1.2438 | B.14 | C.12 |
| 1.2439 | B.15 | C.12 |
| 1.2440 | B.16 | C.12 |
| 1.2441 | B.17 | C.12 |
| 1.2442 | B.18 | C.12 |
| 1.2443 | B.19 | C.12 |
| 1.2444 | B.20 | C.12 |
| 1.2445 | B.21 | C.12 |
| 1.2446 | B.22 | C.12 |
| 1.2447 | B.23 | C.12 |
| 1.2448 | B.24 | C.12 |
| 1.2449 | B.25 | C.12 |
| 1.2450 | B.26 | C.12 |
| 1.2451 | B.27 | C.12 |
| 1.2452 | B.28 | C.12 |
| 1.2453 | B.29 | C.12 |
| 1.2454 | B.30 | C.12 |
| 1.2455 | B.31 | C.12 |
| 1.2456 | B.32 | C.12 |
| 1.2457 | B.33 | C.12 |
| 1.2458 | B.34 | C.12 |
| 1.2459 | B.35 | C.12 |
| 1.2460 | B.36 | C.12 |
| 1.2461 | B.37 | C.12 |
| 1.2462 | B.38 | C.12 |
| 1.2463 | B.39 | C.12 |
| 1.2464 | B.40 | C.12 |
| 1.2465 | B.41 | C.12 |
| 1.2466 | B.42 | C.12 |
| 1.2467 | B.43 | C.12 |
| 1.2468 | B.44 | C.12 |
| 1.2469 | B.45 | C.12 |
| 1.2470 | B.46 | C.12 |
| 1.2471 | B.47 | C.12 |
| 1.2472 | B.48 | C.12 |
| 1.2473 | B.49 | C.12 |
| 1.2474 | B.50 | C.12 |
| 1.2475 | B.51 | C.12 |
| 1.2476 | B.52 | C.12 |
| 1.2477 | B.53 | C.12 |

TABLE 1-continued (compositions 1.1 to 1.3653):

| comp. no. | herbicide B | safener C |
|---|---|---|
| 1.2478 | B.54 | C.12 |
| 1.2479 | B.55 | C.12 |
| 1.2480 | B.56 | C.12 |
| 1.2481 | B.57 | C.12 |
| 1.2482 | B.58. | C.12 |
| 1.2483 | B.59 | C.12 |
| 1.2484 | B.60 | C.12 |
| 1.2485 | B.61 | C.12 |
| 1.2486 | B.62 | C.12 |
| 1.2487 | B.63 | C.12 |
| 1.2488 | B.64 | C.12 |
| 1.2489 | B.65 | C.12 |
| 1.2490 | B.66 | C.12 |
| 1.2491 | B.67 | C.12 |
| 1.2492 | B.68 | C.12 |
| 1.2493 | B.69 | C.12 |
| 1.2494 | B.70 | C.12 |
| 1.2495 | B.71 | C.12 |
| 1.2496 | B.72 | C.12 |
| 1.2497 | B.73 | C.12 |
| 1.2498 | B.74 | C.12 |
| 1.2499 | B.75 | C.12 |
| 1.2500 | B.76 | C.12 |
| 1.2501 | B.77 | C.12 |
| 1.2502 | B.78 | C.12 |
| 1.2503 | B.79 | C.12 |
| 1.2504 | B.80 | C.12 |
| 1.2505 | B.81 | C.12 |
| 1.2506 | B.82 | C.12 |
| 1.2507 | B.83 | C.12 |
| 1.2508 | B.84 | C.12 |
| 1.2509 | B.85 | C.12 |
| 1.2510 | B.86 | C.12 |
| 1.2511 | B.87 | C.12 |
| 1.2512 | B.88 | C.12 |
| 1.2513 | B.89 | C.12 |
| 1.2514 | B.90 | C.12 |
| 1.2515 | B.91 | C.12 |
| 1.2516 | B.92 | C.12 |
| 1.2517 | B.93 | C.12 |
| 1.2518 | B.94 | C.12 |
| 1.2519 | B.95 | C.12 |
| 1.2520 | B.96 | C.12 |
| 1.2521 | B.97 | C.12 |
| 1.2522 | B.98 | C.12 |
| 1.2523 | B.99 | C.12 |
| 1.2524 | B.100 | C.12 |
| 1.2525 | B.101 | C.12 |
| 1.2526 | B.102 | C.12 |
| 1.2527 | B.103 | C.12 |
| 1.2528 | B.104 | C.12 |
| 1.2529 | B.105 | C.12 |
| 1.2530 | B.106 | C.12 |
| 1.2531 | B.107 | C.12 |
| 1.2532 | B.108 | C.12 |
| 1.2533 | B.109 | C.12 |
| 1.2534 | B.110 | C.12 |
| 1.2535 | B.111 | C.12 |
| 1.2536 | B.112 | C.12 |
| 1.2537 | B.113 | C.12 |
| 1.2538 | B.114 | C.12 |
| 1.2539 | B.115 | C.12 |
| 1.2540 | B.116 | C.12 |
| 1.2541 | B.117 | C.12 |
| 1.2542 | B.118 | C.12 |
| 1.2543 | B.119 | C.12 |
| 1.2544 | B.120 | C.12 |
| 1.2545 | B.121 | C.12 |
| 1.2546 | B.122 | C.12 |
| 1.2547 | B.123 | C.12 |
| 1.2548 | B.124 | C.12 |
| 1.2549 | B.125 | C.12 |
| 1.2550 | B.126 | C.12 |
| 1.2551 | B.127 | C.12 |
| 1.2552 | B.128 | C.12 |
| 1.2553 | B.129 | C.12 |
| 1.2554 | B.130 | C.12 |
| 1.2555 | B.131 | C.12 |
| 1.2556 | B.132 | C.12 |
| 1.2557 | B.133 | C.12 |
| 1.2558 | B.134 | C.12 |
| 1.2559 | B.135 | C.12 |
| 1.2560 | B.136 | C.12 |
| 1.2561 | B.137 | C.12 |
| 1.2562 | B.138 | C.12 |
| 1.2563 | B.139 | C.12 |
| 1.2564 | B.140 | C.12 |
| 1.2565 | B.141 | C.12 |
| 1.2566 | B.142 | C.12 |
| 1.2567 | B.143 | C.12 |
| 1.2568 | B.144 | C.12 |
| 1.2569 | B.145 | C.12 |
| 1.2570 | B.146 | C.12 |
| 1.2571 | B.147 | C.12 |
| 1.2572 | B.148 | C.12 |
| 1.2573 | B.149 | C.12 |
| 1.2574 | B.150 | C.12 |
| 1.2575 | B.151 | C.12 |
| 1.2576 | B.152 | C.12 |
| 1.2577 | B.153 | C.12 |
| 1.2578 | B.154 | C.12 |
| 1.2579 | B.155 | C.12 |
| 1.2580 | B.156 | C.12 |
| 1.2581 | B.157 | C.12 |
| 1.2582 | B.158 | C.12 |
| 1.2583 | B.159 | C.12 |
| 1.2584 | B.160 | C.12 |
| 1.2585 | B.161 | C.12 |
| 1.2586 | B.162 | C.12 |
| 1.2587 | B.163 | C.12 |
| 1.2588 | B.164 | C.12 |
| 1.2589 | B.165 | C.12 |
| 1.2590 | B.166 | C.12 |
| 1.2591 | B.167 | C.12 |
| 1.2592 | B.168 | C.12 |
| 1.2593 | B.169 | C.12 |
| 1.2594 | B.170 | C.12 |
| 1.2595 | B.171 | C.12 |
| 1.2596 | B.172 | C.12 |
| 1.2597 | B.173 | C.12 |
| 1.2598 | B.174 | C.12 |
| 1.2599 | B.175 | C.12 |
| 1.2600 | B.176 | C.12 |
| 1.2601 | B.177 | C.12 |
| 1.2602 | B.178 | C.12 |
| 1.2603 | B.179 | C.12 |
| 1.2604 | B.180 | C.12 |
| 1.2605 | B.181 | C.12 |
| 1.2606 | B.182 | C.12 |
| 1.2607 | B.183 | C.12 |
| 1.2608 | B.184 | C.12 |
| 1.2609 | B.185 | C.12 |
| 1.2610 | B.186 | C.12 |
| 1.2611 | B.187 | C.12 |
| 1.2612 | B.188 | C.12 |
| 1.2613 | B.189 | C.12 |
| 1.2614 | B.190 | C.12 |
| 1.2615 | B.191 | C.12 |
| 1.2616 | B.192 | C.12 |
| 1.2617 | B.193 | C.12 |
| 1.2618 | B.194 | C.12 |
| 1.2619 | B.195 | C.12 |
| 1.2620 | B.196 | C.12 |
| 1.2621 | B.197 | C.12 |
| 1.2622 | B.198 | C.12 |
| 1.2623 | B.199 | C.12 |
| 1.2624 | B.200 | C.12 |
| 1.2625 | B.201 | C.12 |
| 1.2626 | B.202 | C.12 |
| 1.2627 | B.1 | C.13 |

TABLE 1-continued (compositions 1.1 to 1.3653):

| comp. no. | herbicide B | safener C |
|---|---|---|
| 1.2628 | B.2 | C.13 |
| 1.2629 | B.3 | C.13 |
| 1.2630 | B.4 | C.13 |
| 1.2631 | B.5 | C.13 |
| 1.2632 | B.6 | C.13 |
| 1.2633 | B.7 | C.13 |
| 1.2634 | B.8 | C.13 |
| 1.2635 | B.9 | C.13 |
| 1.2636 | B.10 | C.13 |
| 1.2637 | B.11 | C.13 |
| 1.2638 | B.12 | C.13 |
| 1.2639 | B.13 | C.13 |
| 1.2640 | B.14 | C.13 |
| 1.2641 | B.15 | C.13 |
| 1.2642 | B.16 | C.13 |
| 1.2643 | B.17 | C.13 |
| 1.2644 | B.18 | C.13 |
| 1.2645 | B.19 | C.13 |
| 1.2646 | B.20 | C.13 |
| 1.2647 | B.21 | C.13 |
| 1.2648 | B.22 | C.13 |
| 1.2649 | B.23 | C.13 |
| 1.2650 | B.24 | C.13 |
| 1.2651 | B.25 | C.13 |
| 1.2652 | B.26 | C.13 |
| 1.2653 | B.27 | C.13 |
| 1.2654 | B.28 | C.13 |
| 1.2655 | B.29 | C.13 |
| 1.2656 | B.30 | C.13 |
| 1.2657 | B.31 | C.13 |
| 1.2658 | B.32 | C.13 |
| 1.2659 | B.33 | C.13 |
| 1.2660 | B.34 | C.13 |
| 1.2661 | B.35 | C.13 |
| 1.2662 | B.36 | C.13 |
| 1.2663 | B.37 | C.13 |
| 1.2664 | B.38 | C.13 |
| 1.2665 | B.39 | C.13 |
| 1.2666 | B.40 | C.13 |
| 1.2667 | B.41 | C.13 |
| 1.2668 | B.42 | C.13 |
| 1.2669 | B.43 | C.13 |
| 1.2670 | B.44 | C.13 |
| 1.2671 | B.45 | C.13 |
| 1.2672 | B.46 | C.13 |
| 1.2673 | B.47 | C.13 |
| 1.2674 | B.48 | C.13 |
| 1.2675 | B.49 | C.13 |
| 1.2676 | B.50 | C.13 |
| 1.2677 | B.51 | C.13 |
| 1.2678 | B.52 | C.13 |
| 1.2679 | B.53 | C.13 |
| 1.2680 | B.54 | C.13 |
| 1.2681 | B.55 | C.13 |
| 1.2682 | B.56 | C.13 |
| 1.2683 | B.57 | C.13 |
| 1.2684 | B.58. | C.13 |
| 1.2685 | B.59 | C.13 |
| 1.2686 | B.60 | C.13 |
| 1.2687 | B.61 | C.13 |
| 1.2688 | B.62 | C.13 |
| 1.2689 | B.63 | C.13 |
| 1.2690 | B.64 | C.13 |
| 1.2691 | B.65 | C.13 |
| 1.2692 | B.66 | C.13 |
| 1.2693 | B.67 | C.13 |
| 1.2694 | B.68 | C.13 |
| 1.2695 | B.69 | C.13 |
| 1.2696 | B.70 | C.13 |
| 1.2697 | B.71 | C.13 |
| 1.2698 | B.72 | C.13 |
| 1.2699 | B.73 | C.13 |
| 1.2700 | B.74 | C.13 |
| 1.2701 | B.75 | C.13 |
| 1.2702 | B.76 | C.13 |
| 1.2703 | B.77 | C.13 |
| 1.2704 | B.78 | C.13 |
| 1.2705 | B.79 | C.13 |
| 1.2706 | B.80 | C.13 |
| 1.2707 | B.81 | C.13 |
| 1.2708 | B.82 | C.13 |
| 1.2709 | B.83 | C.13 |
| 1.2710 | B.84 | C.13 |
| 1.2711 | B.85 | C.13 |
| 1.2712 | B.86 | C.13 |
| 1.2713 | B.87 | C.13 |
| 1.2714 | B.88 | C.13 |
| 1.2715 | B.89 | C.13 |
| 1.2716 | B.90 | C.13 |
| 1.2717 | B.91 | C.13 |
| 1.2718 | B.92 | C.13 |
| 1.2719 | B.93 | C.13 |
| 1.2720 | B.94 | C.13 |
| 1.2721 | B.95 | C.13 |
| 1.2722 | B.96 | C.13 |
| 1.2723 | B.97 | C.13 |
| 1.2724 | B.98 | C.13 |
| 1.2725 | B.99 | C.13 |
| 1.2726 | B.100 | C.13 |
| 1.2727 | B.101 | C.13 |
| 1.2728 | B.102 | C.13 |
| 1.2729 | B.103 | C.13 |
| 1.2730 | B.104 | C.13 |
| 1.2731 | B.105 | C.13 |
| 1.2732 | B.106 | C.13 |
| 1.2733 | B.107 | C.13 |
| 1.2734 | B.108 | C.13 |
| 1.2735 | B.109 | C.13 |
| 1.2736 | B.110 | C.13 |
| 1.2737 | B.111 | C.13 |
| 1.2738 | B.112 | C.13 |
| 1.2739 | B.113 | C.13 |
| 1.2740 | B.114 | C.13 |
| 1.2741 | B.115 | C.13 |
| 1.2742 | B.116 | C.13 |
| 1.2743 | B.117 | C.13 |
| 1.2744 | B.118 | C.13 |
| 1.2745 | B.119 | C.13 |
| 1.2746 | B.120 | C.13 |
| 1.2747 | B.121 | C.13 |
| 1.2748 | B.122 | C.13 |
| 1.2749 | B.123 | C.13 |
| 1.2750 | B.124 | C.13 |
| 1.2751 | B.125 | C.13 |
| 1.2752 | B.126 | C.13 |
| 1.2753 | B.127 | C.13 |
| 1.2754 | B.128 | C.13 |
| 1.2755 | B.129 | C.13 |
| 1.2756 | B.130 | C.13 |
| 1.2757 | B.131 | C.13 |
| 1.2758 | B.132 | C.13 |
| 1.2759 | B.133 | C.13 |
| 1.2760 | B.134 | C.13 |
| 1.2761 | B.135 | C.13 |
| 1.2762 | B.136 | C.13 |
| 1.2763 | B.137 | C.13 |
| 1.2764 | B.138 | C.13 |
| 1.2765 | B.139 | C.13 |
| 1.2766 | B.140 | C.13 |
| 1.2767 | B.141 | C.13 |
| 1.2768 | B.142 | C.13 |
| 1.2769 | B.143 | C.13 |
| 1.2770 | B.144 | C.13 |
| 1.2771 | B.145 | C.13 |
| 1.2772 | B.146 | C.13 |
| 1.2773 | B.147 | C.13 |
| 1.2774 | B.148 | C.13 |
| 1.2775 | B.149 | C.13 |
| 1.2776 | B.150 | C.13 |
| 1.2777 | B.151 | C.13 |

TABLE 1-continued (compositions 1.1 to 1.3653):

| comp. no. | herbicide B | safener C |
|---|---|---|
| 1.2778 | B.152 | C.13 |
| 1.2779 | B.153 | C.13 |
| 1.2780 | B.154 | C.13 |
| 1.2781 | B.155 | C.13 |
| 1.2782 | B.156 | C.13 |
| 1.2783 | B.157 | C.13 |
| 1.2784 | B.158 | C.13 |
| 1.2785 | B.159 | C.13 |
| 1.2786 | B.160 | C.13 |
| 1.2787 | B.161 | C.13 |
| 1.2788 | B.162 | C.13 |
| 1.2789 | B.163 | C.13 |
| 1.2790 | B.164 | C.13 |
| 1.2791 | B.165 | C.13 |
| 1.2792 | B.166 | C.13 |
| 1.2793 | B.167 | C.13 |
| 1.2794 | B.168 | C.13 |
| 1.2795 | B.169 | C.13 |
| 1.2796 | B.170 | C.13 |
| 1.2797 | B.171 | C.13 |
| 1.2798 | B.172 | C.13 |
| 1.2799 | B.173 | C.13 |
| 1.2800 | B.174 | C.13 |
| 1.2801 | B.175 | C.13 |
| 1.2802 | B.176 | C.13 |
| 1.2803 | B.177 | C.13 |
| 1.2804 | B.178 | C.13 |
| 1.2805 | B.179 | C.13 |
| 1.2806 | B.180 | C.13 |
| 1.2807 | B.181 | C.13 |
| 1.2808 | B.182 | C.13 |
| 1.2809 | B.183 | C.13 |
| 1.2810 | B.184 | C.13 |
| 1.2811 | B.185 | C.13 |
| 1.2812 | B.186 | C.13 |
| 1.2813 | B.187 | C.13 |
| 1.2814 | B.188 | C.13 |
| 1.2815 | B.189 | C.13 |
| 1.2816 | B.190 | C.13 |
| 1.2817 | B.191 | C.13 |
| 1.2818 | B.192 | C.13 |
| 1.2819 | B.193 | C.13 |
| 1.2820 | B.194 | C.13 |
| 1.2821 | B.195 | C.13 |
| 1.2822 | B.196 | C.13 |
| 1.2823 | B.197 | C.13 |
| 1.2824 | B.198 | C.13 |
| 1.2825 | B.199 | C.13 |
| 1.2826 | B.200 | C.13 |
| 1.2827 | B.201 | C.13 |
| 1.2828 | B.202 | C.13 |
| 1.2829 | B.1 | C.14 |
| 1.2830 | B.2 | C.14 |
| 1.2831 | B.3 | C.14 |
| 1.2832 | B.4 | C.14 |
| 1.2833 | B.5 | C.14 |
| 1.2834 | B.6 | C.14 |
| 1.2835 | B.7 | C.14 |
| 1.2836 | B.8 | C.14 |
| 1.2837 | B.9 | C.14 |
| 1.2838 | B.10 | C.14 |
| 1.2839 | B.11 | C.14 |
| 1.2840 | B.12 | C.14 |
| 1.2841 | B.13 | C.14 |
| 1.2842 | B.14 | C.14 |
| 1.2843 | B.15 | C.14 |
| 1.2844 | B.16 | C.14 |
| 1.2845 | B.17 | C.14 |
| 1.2846 | B.18 | C.14 |
| 1.2847 | B.19 | C.14 |
| 1.2848 | B.20 | C.14 |
| 1.2849 | B.21 | C.14 |
| 1.2850 | B.22 | C.14 |
| 1.2851 | B.23 | C.14 |
| 1.2852 | B.24 | C.14 |
| 1.2853 | B.25 | C.14 |
| 1.2854 | B.26 | C.14 |
| 1.2855 | B.27 | C.14 |
| 1.2856 | B.28 | C.14 |
| 1.2857 | B.29 | C.14 |
| 1.2858 | B.30 | C.14 |
| 1.2859 | B.31 | C.14 |
| 1.2860 | B.32 | C.14 |
| 1.2861 | B.33 | C.14 |
| 1.2862 | B.34 | C.14 |
| 1.2863 | B.35 | C.14 |
| 1.2864 | B.36 | C.14 |
| 1.2865 | B.37 | C.14 |
| 1.2866 | B.38 | C.14 |
| 1.2867 | B.39 | C.14 |
| 1.2868 | B.40 | C.14 |
| 1.2869 | B.41 | C.14 |
| 1.2870 | B.42 | C.14 |
| 1.2871 | B.43 | C.14 |
| 1.2872 | B.44 | C.14 |
| 1.2873 | B.45 | C.14 |
| 1.2874 | B.46 | C.14 |
| 1.2875 | B.47 | C.14 |
| 1.2876 | B.48 | C.14 |
| 1.2877 | B.49 | C.14 |
| 1.2878 | B.50 | C.14 |
| 1.2879 | B.51 | C.14 |
| 1.2880 | B.52 | C.14 |
| 1.2881 | B.53 | C.14 |
| 1.2882 | B.54 | C.14 |
| 1.2883 | B.55 | C.14 |
| 1.2884 | B.56 | C.14 |
| 1.2885 | B.57 | C.14 |
| 1.2886 | B.58. | C.14 |
| 1.2887 | B.59 | C.14 |
| 1.2888 | B.60 | C.14 |
| 1.2889 | B.61 | C.14 |
| 1.2890 | B.62 | C.14 |
| 1.2891 | B.63 | C.14 |
| 1.2892 | B.64 | C.14 |
| 1.2893 | B.65 | C.14 |
| 1.2894 | B.66 | C.14 |
| 1.2895 | B.67 | C.14 |
| 1.2896 | B.68 | C.14 |
| 1.2897 | B.69 | C.14 |
| 1.2898 | B.70 | C.14 |
| 1.2899 | B.71 | C.14 |
| 1.2900 | B.72 | C.14 |
| 1.2901 | B.73 | C.14 |
| 1.2902 | B.74 | C.14 |
| 1.2903 | B.75 | C.14 |
| 1.2904 | B.76 | C.14 |
| 1.2905 | B.77 | C.14 |
| 1.2906 | B.78 | C.14 |
| 1.2907 | B.79 | C.14 |
| 1.2908 | B.80 | C.14 |
| 1.2909 | B.81 | C.14 |
| 1.2910 | B.82 | C.14 |
| 1.2911 | B.83 | C.14 |
| 1.2912 | B.84 | C.14 |
| 1.2913 | B.85 | C.14 |
| 1.2914 | B.86 | C.14 |
| 1.2915 | B.87 | C.14 |
| 1.2916 | B.88 | C.14 |
| 1.2917 | B.89 | C.14 |
| 1.2918 | B.90 | C.14 |
| 1.2919 | B.91 | C.14 |
| 1.2920 | B.92 | C.14 |
| 1.2921 | B.93 | C.14 |
| 1.2922 | B.94 | C.14 |
| 1.2923 | B.95 | C.14 |
| 1.2924 | B.96 | C.14 |
| 1.2925 | B.97 | C.14 |
| 1.2926 | B.98 | C.14 |
| 1.2927 | B.99 | C.14 |

TABLE 1-continued (compositions 1.1 to 1.3653):

| comp. no. | herbicide B | safener C |
|---|---|---|
| 1.2928 | B.100 | C.14 |
| 1.2929 | B.101 | C.14 |
| 1.2930 | B.102 | C.14 |
| 1.2931 | B.103 | C.14 |
| 1.2932 | B.104 | C.14 |
| 1.2933 | B.105 | C.14 |
| 1.2934 | B.106 | C.14 |
| 1.2935 | B.107 | C.14 |
| 1.2936 | B.108 | C.14 |
| 1.2937 | B.109 | C.14 |
| 1.2938 | B.110 | C.14 |
| 1.2939 | B.111 | C.14 |
| 1.2940 | B.112 | C.14 |
| 1.2941 | B.113 | C.14 |
| 1.2942 | B.114 | C.14 |
| 1.2943 | B.115 | C.14 |
| 1.2944 | B.116 | C.14 |
| 1.2945 | B.117 | C.14 |
| 1.2946 | B.118 | C.14 |
| 1.2947 | B.119 | C.14 |
| 1.2948 | B.120 | C.14 |
| 1.2949 | B.121 | C.14 |
| 1.2950 | B.122 | C.14 |
| 1.2951 | B.123 | C.14 |
| 1.2952 | B.124 | C.14 |
| 1.2953 | B.125 | C.14 |
| 1.2954 | B.126 | C.14 |
| 1.2955 | B.127 | C.14 |
| 1.2956 | B.128 | C.14 |
| 1.2957 | B.129 | C.14 |
| 1.2958 | B.130 | C.14 |
| 1.2959 | B.131 | C.14 |
| 1.2960 | B.132 | C.14 |
| 1.2961 | B.133 | C.14 |
| 1.2962 | B.134 | C.14 |
| 1.2963 | B.135 | C.14 |
| 1.2964 | B.136 | C.14 |
| 1.2965 | B.137 | C.14 |
| 1.2966 | B.138 | C.14 |
| 1.2967 | B.139 | C.14 |
| 1.2968 | B.140 | C.14 |
| 1.2969 | B.141 | C.14 |
| 1.2970 | B.142 | C.14 |
| 1.2971 | B.143 | C.14 |
| 1.2972 | B.144 | C.14 |
| 1.2973 | B.145 | C.14 |
| 1.2974 | B.146 | C.14 |
| 1.2975 | B.147 | C.14 |
| 1.2976 | B.148 | C.14 |
| 1.2977 | B.149 | C.14 |
| 1.2978 | B.150 | C.14 |
| 1.2979 | B.151 | C.14 |
| 1.2980 | B.152 | C.14 |
| 1.2981 | B.153 | C.14 |
| 1.2982 | B.154 | C.14 |
| 1.2983 | B.155 | C.14 |
| 1.2984 | B.156 | C.14 |
| 1.2985 | B.157 | C.14 |
| 1.2986 | B.158 | C.14 |
| 1.2987 | B.159 | C.14 |
| 1.2988 | B.160 | C.14 |
| 1.2989 | B.161 | C.14 |
| 1.2990 | B.162 | C.14 |
| 1.2991 | B.163 | C.14 |
| 1.2992 | B.164 | C.14 |
| 1.2993 | B.165 | C.14 |
| 1.2994 | B.166 | C.14 |
| 1.2995 | B.167 | C.14 |
| 1.2996 | B.168 | C.14 |
| 1.2997 | B.169 | C.14 |
| 1.2998 | B.170 | C.14 |
| 1.2999 | B.171 | C.14 |
| 1.3000 | B.172 | C.14 |
| 1.3001 | B.173 | C.14 |
| 1.3002 | B.174 | C.14 |
| 1.3003 | B.175 | C.14 |
| 1.3004 | B.176 | C.14 |
| 1.3005 | B.177 | C.14 |
| 1.3006 | B.178 | C.14 |
| 1.3007 | B.179 | C.14 |
| 1.3008 | B.180 | C.14 |
| 1.3009 | B.181 | C.14 |
| 1.3010 | B.182 | C.14 |
| 1.3011 | B.183 | C.14 |
| 1.3012 | B.184 | C.14 |
| 1.3013 | B.185 | C.14 |
| 1.3014 | B.186 | C.14 |
| 1.3015 | B.187 | C.14 |
| 1.3016 | B.188 | C.14 |
| 1.3017 | B.189 | C.14 |
| 1.3018 | B.190 | C.14 |
| 1.3019 | B.191 | C.14 |
| 1.3020 | B.192 | C.14 |
| 1.3021 | B.193 | C.14 |
| 1.3022 | B.194 | C.14 |
| 1.3023 | B.195 | C.14 |
| 1.3024 | B.196 | C.14 |
| 1.3025 | B.197 | C.14 |
| 1.3026 | B.198 | C.14 |
| 1.3027 | B.199 | C.14 |
| 1.3028 | B.200 | C.14 |
| 1.3029 | B.201 | C.14 |
| 1.3030 | B.202 | C.14 |
| 1.3031 | B.1 | C.15 |
| 1.3032 | B.2 | C.15 |
| 1.3033 | B.3 | C.15 |
| 1.3034 | B.4 | C.15 |
| 1.3035 | B.5 | C.15 |
| 1.3036 | B.6 | C.15 |
| 1.3037 | B.7 | C.15 |
| 1.3038 | B.8 | C.15 |
| 1.3039 | B.9 | C.15 |
| 1.3040 | B.10 | C.15 |
| 1.3041 | B.11 | C.15 |
| 1.3042 | B.12 | C.15 |
| 1.3043 | B.13 | C.15 |
| 1.3044 | B.14 | C.15 |
| 1.3045 | B.15 | C.15 |
| 1.3046 | B.16 | C.15 |
| 1.3047 | B.17 | C.15 |
| 1.3048 | B.18 | C.15 |
| 1.3049 | B.19 | C.15 |
| 1.3050 | B.20 | C.15 |
| 1.3051 | B.21 | C.15 |
| 1.3052 | B.22 | C.15 |
| 1.3053 | B.23 | C.15 |
| 1.3054 | B.24 | C.15 |
| 1.3055 | B.25 | C.15 |
| 1.3056 | B.26 | C.15 |
| 1.3057 | B.27 | C.15 |
| 1.3058 | B.28 | C.15 |
| 1.3059 | B.29 | C.15 |
| 1.3060 | B.30 | C.15 |
| 1.3061 | B.31 | C.15 |
| 1.3062 | B.32 | C.15 |
| 1.3063 | B.33 | C.15 |
| 1.3064 | B.34 | C.15 |
| 1.3065 | B.35 | C.15 |
| 1.3066 | B.36 | C.15 |
| 1.3067 | B.37 | C.15 |
| 1.3068 | B.38 | C.15 |
| 1.3069 | B.39 | C.15 |
| 1.3070 | B.40 | C.15 |
| 1.3071 | B.41 | C.15 |
| 1.3072 | B.42 | C.15 |
| 1.3073 | B.43 | C.15 |
| 1.3074 | B.44 | C.15 |
| 1.3075 | B.45 | C.15 |
| 1.3076 | B.46 | C.15 |
| 1.3077 | B.47 | C.15 |

TABLE 1-continued (compositions 1.1 to 1.3653):

| comp. no. | herbicide B | safener C |
|---|---|---|
| 1.3078 | B.48 | C.15 |
| 1.3079 | B.49 | C.15 |
| 1.3080 | B.50 | C.15 |
| 1.3081 | B.51 | C.15 |
| 1.3082 | B.52 | C.15 |
| 1.3083 | B.53 | C.15 |
| 1.3084 | B.54 | C.15 |
| 1.3085 | B.55 | C.15 |
| 1.3086 | B.56 | C.15 |
| 1.3087 | B.57 | C.15 |
| 1.3088 | B.58. | C.15 |
| 1.3089 | B.59 | C.15 |
| 1.3090 | B.60 | C.15 |
| 1.3091 | B.61 | C.15 |
| 1.3092 | B.62 | C.15 |
| 1.3093 | B.63 | C.15 |
| 1.3094 | B.64 | C.15 |
| 1.3095 | B.65 | C.15 |
| 1.3096 | B.66 | C.15 |
| 1.3097 | B.67 | C.15 |
| 1.3098 | B.68 | C.15 |
| 1.3099 | B.69 | C.15 |
| 1.3100 | B.70 | C.15 |
| 1.3101 | B.71 | C.15 |
| 1.3102 | B.72 | C.15 |
| 1.3103 | B.73 | C.15 |
| 1.3104 | B.74 | C.15 |
| 1.3105 | B.75 | C.15 |
| 1.3106 | B.76 | C.15 |
| 1.3107 | B.77 | C.15 |
| 1.3108 | B.78 | C.15 |
| 1.3109 | B.79 | C.15 |
| 1.3110 | B.80 | C.15 |
| 1.3111 | B.81 | C.15 |
| 1.3112 | B.82 | C.15 |
| 1.3113 | B.83 | C.15 |
| 1.3114 | B.84 | C.15 |
| 1.3115 | B.85 | C.15 |
| 1.3116 | B.86 | C.15 |
| 1.3117 | B.87 | C.15 |
| 1.3118 | B.88 | C.15 |
| 1.3119 | B.89 | C.15 |
| 1.3120 | B.90 | C.15 |
| 1.3121 | B.91 | C.15 |
| 1.3122 | B.92 | C.15 |
| 1.3123 | B.93 | C.15 |
| 1.3124 | B.94 | C.15 |
| 1.3125 | B.95 | C.15 |
| 1.3126 | B.96 | C.15 |
| 1.3127 | B.97 | C.15 |
| 1.3128 | B.98 | C.15 |
| 1.3129 | B.99 | C.15 |
| 1.3130 | B.100 | C.15 |
| 1.3131 | B.101 | C.15 |
| 1.3132 | B.102 | C.15 |
| 1.3133 | B.103 | C.15 |
| 1.3134 | B.104 | C.15 |
| 1.3135 | B.105 | C.15 |
| 1.3136 | B.106 | C.15 |
| 1.3137 | B.107 | C.15 |
| 1.3138 | B.108 | C.15 |
| 1.3139 | B.109 | C.15 |
| 1.3140 | B.110 | C.15 |
| 1.3141 | B.111 | C.15 |
| 1.3142 | B.112 | C.15 |
| 1.3143 | B.113 | C.15 |
| 1.3144 | B.114 | C.15 |
| 1.3145 | B.115 | C.15 |
| 1.3146 | B.116 | C.15 |
| 1.3147 | B.117 | C.15 |
| 1.3148 | B.118 | C.15 |
| 1.3149 | B.119 | C.15 |
| 1.3150 | B.120 | C.15 |
| 1.3151 | B.121 | C.15 |
| 1.3152 | B.122 | C.15 |
| 1.3153 | B.123 | C.15 |
| 1.3154 | B.124 | C.15 |
| 1.3155 | B.125 | C.15 |
| 1.3156 | B.126 | C.15 |
| 1.3157 | B.127 | C.15 |
| 1.3158 | B.128 | C.15 |
| 1.3159 | B.129 | C.15 |
| 1.3160 | B.130 | C.15 |
| 1.3161 | B.131 | C.15 |
| 1.3162 | B.132 | C.15 |
| 1.3163 | B.133 | C.15 |
| 1.3164 | B.134 | C.15 |
| 1.3165 | B.135 | C.15 |
| 1.3166 | B.136 | C.15 |
| 1.3167 | B.137 | C.15 |
| 1.3168 | B.138 | C.15 |
| 1.3169 | B.139 | C.15 |
| 1.3170 | B.140 | C.15 |
| 1.3171 | B.141 | C.15 |
| 1.3172 | B.142 | C.15 |
| 1.3173 | B.143 | C.15 |
| 1.3174 | B.144 | C.15 |
| 1.3175 | B.145 | C.15 |
| 1.3176 | B.146 | C.15 |
| 1.3177 | B.147 | C.15 |
| 1.3178 | B.148 | C.15 |
| 1.3179 | B.149 | C.15 |
| 1.3180 | B.150 | C.15 |
| 1.3181 | B.151 | C.15 |
| 1.3182 | B.152 | C.15 |
| 1.3183 | B.153 | C.15 |
| 1.3184 | B.154 | C.15 |
| 1.3185 | B.155 | C.15 |
| 1.3186 | B.156 | C.15 |
| 1.3187 | B.157 | C.15 |
| 1.3188 | B.158 | C.15 |
| 1.3189 | B.159 | C.15 |
| 1.3190 | B.160 | C.15 |
| 1.3191 | B.161 | C.15 |
| 1.3192 | B.162 | C.15 |
| 1.3193 | B.163 | C.15 |
| 1.3194 | B.164 | C.15 |
| 1.3195 | B.165 | C.15 |
| 1.3196 | B.166 | C.15 |
| 1.3197 | B.167 | C.15 |
| 1.3198 | B.168 | C.15 |
| 1.3199 | B.169 | C.15 |
| 1.3200 | B.170 | C.15 |
| 1.3201 | B.171 | C.15 |
| 1.3202 | B.172 | C.15 |
| 1.3203 | B.173 | C.15 |
| 1.3204 | B.174 | C.15 |
| 1.3205 | B.175 | C.15 |
| 1.3206 | B.176 | C.15 |
| 1.3207 | B.177 | C.15 |
| 1.3208 | B.178 | C.15 |
| 1.3209 | B.179 | C.15 |
| 1.3210 | B.180 | C.15 |
| 1.3211 | B.181 | C.15 |
| 1.3212 | B.182 | C.15 |
| 1.3213 | B.183 | C.15 |
| 1.3214 | B.184 | C.15 |
| 1.3215 | B.185 | C.15 |
| 1.3216 | B.186 | C.15 |
| 1.3217 | B.187 | C.15 |
| 1.3218 | B.188 | C.15 |
| 1.3219 | B.189 | C.15 |
| 1.3220 | B.190 | C.15 |
| 1.3221 | B.191 | C.15 |
| 1.3222 | B.192 | C.15 |
| 1.3223 | B.193 | C.15 |
| 1.3224 | B.194 | C.15 |
| 1.3225 | B.195 | C.15 |
| 1.3226 | B.196 | C.15 |
| 1.3227 | B.197 | C.15 |

TABLE 1-continued (compositions 1.1 to 1.3653):

| comp. no. | herbicide B | safener C |
|---|---|---|
| 1.3228 | B.198 | C.15 |
| 1.3229 | B.199 | C.15 |
| 1.3230 | B.200 | C.15 |
| 1.3231 | B.201 | C.15 |
| 1.3232 | B.202 | C.15 |
| 1.3233 | B.1 | C.16 |
| 1.3234 | B.2 | C.16 |
| 1.3235 | B.3 | C.16 |
| 1.3236 | B.4 | C.16 |
| 1.3237 | B.5 | C.16 |
| 1.3238 | B.6 | C.16 |
| 1.3239 | B.7 | C.16 |
| 1.3240 | B.8 | C.16 |
| 1.3241 | B.9 | C.16 |
| 1.3242 | B.10 | C.16 |
| 1.3243 | B.11 | C.16 |
| 1.3244 | B.12 | C.16 |
| 1.3245 | B.13 | C.16 |
| 1.3246 | B.14 | C.16 |
| 1.3247 | B.15 | C.16 |
| 1.3248 | B.16 | C.16 |
| 1.3249 | B.17 | C.16 |
| 1.3250 | B.18 | C.16 |
| 1.3251 | B.19 | C.16 |
| 1.3252 | B.20 | C.16 |
| 1.3253 | B.21 | C.16 |
| 1.3254 | B.22 | C.16 |
| 1.3255 | B.23 | C.16 |
| 1.3256 | B.24 | C.16 |
| 1.3257 | B.25 | C.16 |
| 1.3258 | B.26 | C.16 |
| 1.3259 | B.27 | C.16 |
| 1.3260 | B.28 | C.16 |
| 1.3261 | B.29 | C.16 |
| 1.3262 | B.30 | C.16 |
| 1.3263 | B.31 | C.16 |
| 1.3264 | B.32 | C.16 |
| 1.3265 | B.33 | C.16 |
| 1.3266 | B.34 | C.16 |
| 1.3267 | B.35 | C.16 |
| 1.3268 | B.36 | C.16 |
| 1.3269 | B.37 | C.16 |
| 1.3270 | B.38 | C.16 |
| 1.3271 | B.39 | C.16 |
| 1.3272 | B.40 | C.16 |
| 1.3273 | B.41 | C.16 |
| 1.3274 | B.42 | C.16 |
| 1.3275 | B.43 | C.16 |
| 1.3276 | B.44 | C.16 |
| 1.3277 | B.45 | C.16 |
| 1.3278 | B.46 | C.16 |
| 1.3279 | B.47 | C.16 |
| 1.3280 | B.48 | C.16 |
| 1.3281 | B.49 | C.16 |
| 1.3282 | B.50 | C.16 |
| 1.3283 | B.51 | C.16 |
| 1.3284 | B.52 | C.16 |
| 1.3285 | B.53 | C.16 |
| 1.3286 | B.54 | C.16 |
| 1.3287 | B.55 | C.16 |
| 1.3288 | B.56 | C.16 |
| 1.3289 | B.57 | C.16 |
| 1.3290 | B.58. | C.16 |
| 1.3291 | B.59 | C.16 |
| 1.3292 | B.60 | C.16 |
| 1.3293 | B.61 | C.16 |
| 1.3294 | B.62 | C.16 |
| 1.3295 | B.63 | C.16 |
| 1.3296 | B.64 | C.16 |
| 1.3297 | B.65 | C.16 |
| 1.3298 | B.66 | C.16 |
| 1.3299 | B.67 | C.16 |
| 1.3300 | B.68 | C.16 |
| 1.3301 | B.69 | C.16 |
| 1.3302 | B.70 | C.16 |
| 1.3303 | B.71 | C.16 |
| 1.3304 | B.72 | C.16 |
| 1.3305 | B.73 | C.16 |
| 1.3306 | B.74 | C.16 |
| 1.3307 | B.75 | C.16 |
| 1.3308 | B.76 | C.16 |
| 1.3309 | B.77 | C.16 |
| 1.3310 | B.78 | C.16 |
| 1.3311 | B.79 | C.16 |
| 1.3312 | B.80 | C.16 |
| 1.3313 | B.81 | C.16 |
| 1.3314 | B.82 | C.16 |
| 1.3315 | B.83 | C.16 |
| 1.3316 | B.84 | C.16 |
| 1.3317 | B.85 | C.16 |
| 1.3318 | B.86 | C.16 |
| 1.3319 | B.87 | C.16 |
| 1.3320 | B.88 | C.16 |
| 1.3321 | B.89 | C.16 |
| 1.3322 | B.90 | C.16 |
| 1.3323 | B.91 | C.16 |
| 1.3324 | B.92 | C.16 |
| 1.3325 | B.93 | C.16 |
| 1.3326 | B.94 | C.16 |
| 1.3327 | B.95 | C.16 |
| 1.3328 | B.96 | C.16 |
| 1.3329 | B.97 | C.16 |
| 1.3330 | B.98 | C.16 |
| 1.3331 | B.99 | C.16 |
| 1.3332 | B.100 | C.16 |
| 1.3333 | B.101 | C.16 |
| 1.3334 | B.102 | C.16 |
| 1.3335 | B.103 | C.16 |
| 1.3336 | B.104 | C.16 |
| 1.3337 | B.105 | C.16 |
| 1.3338 | B.106 | C.16 |
| 1.3339 | B.107 | C.16 |
| 1.3340 | B.108 | C.16 |
| 1.3341 | B.109 | C.16 |
| 1.3342 | B.110 | C.16 |
| 1.3343 | B.111 | C.16 |
| 1.3344 | B.112 | C.16 |
| 1.3345 | B.113 | C.16 |
| 1.3346 | B.114 | C.16 |
| 1.3347 | B.115 | C.16 |
| 1.3348 | B.116 | C.16 |
| 1.3349 | B.117 | C.16 |
| 1.3350 | B.118 | C.16 |
| 1.3351 | B.119 | C.16 |
| 1.3352 | B.120 | C.16 |
| 1.3353 | B.121 | C.16 |
| 1.3354 | B.122 | C.16 |
| 1.3355 | B.123 | C.16 |
| 1.3356 | B.124 | C.16 |
| 1.3357 | B.125 | C.16 |
| 1.3358 | B.126 | C.16 |
| 1.3359 | B.127 | C.16 |
| 1.3360 | B.128 | C.16 |
| 1.3361 | B.129 | C.16 |
| 1.3362 | B.130 | C.16 |
| 1.3363 | B.131 | C.16 |
| 1.3364 | B.132 | C.16 |
| 1.3365 | B.133 | C.16 |
| 1.3366 | B.134 | C.16 |
| 1.3367 | B.135 | C.16 |
| 1.3368 | B.136 | C.16 |
| 1.3369 | B.137 | C.16 |
| 1.3370 | B.138 | C.16 |
| 1.3371 | B.139 | C.16 |
| 1.3372 | B.140 | C.16 |
| 1.3373 | B.141 | C.16 |
| 1.3374 | B.142 | C.16 |
| 1.3375 | B.143 | C.16 |
| 1.3376 | B.144 | C.16 |
| 1.3377 | B.145 | C.16 |

TABLE 1-continued (compositions 1.1 to 1.3653):

| comp. no. | herbicide B | safener C |
|---|---|---|
| 1.3378 | B.146 | C.16 |
| 1.3379 | B.147 | C.16 |
| 1.3380 | B.148 | C.16 |
| 1.3381 | B.149 | C.16 |
| 1.3382 | B.150 | C.16 |
| 1.3383 | B.151 | C.16 |
| 1.3384 | B.152 | C.16 |
| 1.3385 | B.153 | C.16 |
| 1.3386 | B.154 | C.16 |
| 1.3387 | B.155 | C.16 |
| 1.3388 | B.156 | C.16 |
| 1.3389 | B.157 | C.16 |
| 1.3390 | B.158 | C.16 |
| 1.3391 | B.159 | C.16 |
| 1.3392 | B.160 | C.16 |
| 1.3393 | B.161 | C.16 |
| 1.3394 | B.162 | C.16 |
| 1.3395 | B.163 | C.16 |
| 1.3396 | B.164 | C.16 |
| 1.3397 | B.165 | C.16 |
| 1.3398 | B.166 | C.16 |
| 1.3399 | B.167 | C.16 |
| 1.3400 | B.168 | C.16 |
| 1.3401 | B.169 | C.16 |
| 1.3402 | B.170 | C.16 |
| 1.3403 | B.171 | C.16 |
| 1.3404 | B.172 | C.16 |
| 1.3405 | B.173 | C.16 |
| 1.3406 | B.174 | C.16 |
| 1.3407 | B.175 | C.16 |
| 1.3408 | B.176 | C.16 |
| 1.3409 | B.177 | C.16 |
| 1.3410 | B.178 | C.16 |
| 1.3411 | B.179 | C.16 |
| 1.3412 | B.180 | C.16 |
| 1.3413 | B.181 | C.16 |
| 1.3414 | B.182 | C.16 |
| 1.3415 | B.183 | C.16 |
| 1.3416 | B.184 | C.16 |
| 1.3417 | B.185 | C.16 |
| 1.3418 | B.186 | C.16 |
| 1.3419 | B.187 | C.16 |
| 1.3420 | B.188 | C.16 |
| 1.3421 | B.189 | C.16 |
| 1.3422 | B.190 | C.16 |
| 1.3423 | B.191 | C.16 |
| 1.3424 | B.192 | C.16 |
| 1.3425 | B.193 | C.16 |
| 1.3426 | B.194 | C.16 |
| 1.3427 | B.195 | C.16 |
| 1.3428 | B.196 | C.16 |
| 1.3429 | B.197 | C.16 |
| 1.3430 | B.198 | C.16 |
| 1.3431 | B.199 | C.16 |
| 1.3432 | B.200 | C.16 |
| 1.3433 | B.201 | C.16 |
| 1.3434 | B.202 | C.16 |
| 1.3435 | B.1 | C.17 |
| 1.3436 | B.2 | C.17 |
| 1.3437 | B.3 | C.17 |
| 1.3438 | B.4 | C.17 |
| 1.3439 | B.5 | C.17 |
| 1.3440 | B.6 | C.17 |
| 1.3441 | B.7 | C.17 |
| 1.3442 | B.8 | C.17 |
| 1.3443 | B.9 | C.17 |
| 1.3444 | B.10 | C.17 |
| 1.3445 | B.11 | C.17 |
| 1.3446 | B.12 | C.17 |
| 1.3447 | B.13 | C.17 |
| 1.3448 | B.14 | C.17 |
| 1.3449 | B.15 | C.17 |
| 1.3450 | B.16 | C.17 |
| 1.3451 | B.17 | C.17 |
| 1.3452 | B.18 | C.17 |
| 1.3453 | B.19 | C.17 |
| 1.3454 | B.20 | C.17 |
| 1.3455 | B.21 | C.17 |
| 1.3456 | B.22 | C.17 |
| 1.3457 | B.23 | C.17 |
| 1.3458 | B.24 | C.17 |
| 1.3459 | B.25 | C.17 |
| 1.3460 | B.26 | C.17 |
| 1.3461 | B.27 | C.17 |
| 1.3462 | B.28 | C.17 |
| 1.3463 | B.29 | C.17 |
| 1.3464 | B.30 | C.17 |
| 1.3465 | B.31 | C.17 |
| 1.3466 | B.32 | C.17 |
| 1.3467 | B.33 | C.17 |
| 1.3468 | B.34 | C.17 |
| 1.3469 | B.35 | C.17 |
| 1.3470 | B.36 | C.17 |
| 1.3471 | B.37 | C.17 |
| 1.3472 | B.38 | C.17 |
| 1.3473 | B.39 | C.17 |
| 1.3474 | B.40 | C.17 |
| 1.3475 | B.41 | C.17 |
| 1.3476 | B.42 | C.17 |
| 1.3477 | B.43 | C.17 |
| 1.3478 | B.44 | C.17 |
| 1.3479 | B.45 | C.17 |
| 1.3480 | B.46 | C.17 |
| 1.3481 | B.47 | C.17 |
| 1.3482 | B.48 | C.17 |
| 1.3483 | B.49 | C.17 |
| 1.3484 | B.50 | C.17 |
| 1.3485 | B.51 | C.17 |
| 1.3486 | B.52 | C.17 |
| 1.3487 | B.53 | C.17 |
| 1.3488 | B.54 | C.17 |
| 1.3489 | B.55 | C.17 |
| 1.3490 | B.56 | C.17 |
| 1.3491 | B.57 | C.17 |
| 1.3492 | B.58. | C.17 |
| 1.3493 | B.59 | C.17 |
| 1.3494 | B.60 | C.17 |
| 1.3495 | B.61 | C.17 |
| 1.3496 | B.62 | C.17 |
| 1.3497 | B.63 | C.17 |
| 1.3498 | B.64 | C.17 |
| 1.3499 | B.65 | C.17 |
| 1.3500 | B.66 | C.17 |
| 1.3501 | B.67 | C.17 |
| 1.3502 | B.68 | C.17 |
| 1.3503 | B.69 | C.17 |
| 1.3504 | B.70 | C.17 |
| 1.3505 | B.71 | C.17 |
| 1.3506 | B.72 | C.17 |
| 1.3507 | B.73 | C.17 |
| 1.3508 | B.74 | C.17 |
| 1.3509 | B.75 | C.17 |
| 1.3510 | B.76 | C.17 |
| 1.3511 | B.77 | C.17 |
| 1.3512 | B.78 | C.17 |
| 1.3513 | B.79 | C.17 |
| 1.3514 | B.80 | C.17 |
| 1.3515 | B.81 | C.17 |
| 1.3516 | B.82 | C.17 |
| 1.3517 | B.83 | C.17 |
| 1.3518 | B.84 | C.17 |
| 1.3519 | B.85 | C.17 |
| 1.3520 | B.86 | C.17 |
| 1.3521 | B.87 | C.17 |
| 1.3522 | B.88 | C.17 |
| 1.3523 | B.89 | C.17 |
| 1.3524 | B.90 | C.17 |
| 1.3525 | B.91 | C.17 |
| 1.3526 | B.92 | C.17 |
| 1.3527 | B.93 | C.17 |

TABLE 1-continued (compositions 1.1 to 1.3653):

| comp. no. | herbicide B | safener C |
|---|---|---|
| 1.3528 | B.94 | C.17 |
| 1.3529 | B.95 | C.17 |
| 1.3530 | B.96 | C.17 |
| 1.3531 | B.97 | C.17 |
| 1.3532 | B.98 | C.17 |
| 1.3533 | B.99 | C.17 |
| 1.3534 | B.100 | C.17 |
| 1.3535 | B.101 | C.17 |
| 1.3536 | B.102 | C.17 |
| 1.3537 | B.103 | C.17 |
| 1.3538 | B.104 | C.17 |
| 1.3539 | B.105 | C.17 |
| 1.3540 | B.106 | C.17 |
| 1.3541 | B.107 | C.17 |
| 1.3542 | B.108 | C.17 |
| 1.3543 | B.109 | C.17 |
| 1.3544 | B.110 | C.17 |
| 1.3545 | B.111 | C.17 |
| 1.3546 | B.112 | C.17 |
| 1.3547 | B.113 | C.17 |
| 1.3548 | B.114 | C.17 |
| 1.3549 | B.115 | C.17 |
| 1.3550 | B.116 | C.17 |
| 1.3551 | B.117 | C.17 |
| 1.3552 | B.118 | C.17 |
| 1.3553 | B.119 | C.17 |
| 1.3554 | B.120 | C.17 |
| 1.3555 | B.121 | C.17 |
| 1.3556 | B.122 | C.17 |
| 1.3557 | B.123 | C.17 |
| 1.3558 | B.124 | C.17 |
| 1.3559 | B.125 | C.17 |
| 1.3560 | B.126 | C.17 |
| 1.3561 | B.127 | C.17 |
| 1.3562 | B.128 | C.17 |
| 1.3563 | B.129 | C.17 |
| 1.3564 | B.130 | C.17 |
| 1.3565 | B.131 | C.17 |
| 1.3566 | B.132 | C.17 |
| 1.3567 | B.133 | C.17 |
| 1.3568 | B.134 | C.17 |
| 1.3569 | B.135 | C.17 |
| 1.3570 | B.136 | C.17 |
| 1.3571 | B.137 | C.17 |
| 1.3572 | B.138 | C.17 |
| 1.3573 | B.139 | C.17 |
| 1.3574 | B.140 | C.17 |
| 1.3575 | B.141 | C.17 |
| 1.3576 | B.142 | C.17 |
| 1.3577 | B.143 | C.17 |
| 1.3578 | B.144 | C.17 |
| 1.3579 | B.145 | C.17 |
| 1.3580 | B.146 | C.17 |
| 1.3581 | B.147 | C.17 |
| 1.3582 | B.148 | C.17 |
| 1.3583 | B.149 | C.17 |
| 1.3584 | B.150 | C.17 |
| 1.3585 | B.151 | C.17 |
| 1.3586 | B.152 | C.17 |
| 1.3587 | B.153 | C.17 |
| 1.3588 | B.154 | C.17 |
| 1.3589 | B.155 | C.17 |
| 1.3590 | B.156 | C.17 |
| 1.3591 | B.157 | C.17 |
| 1.3592 | B.158 | C.17 |
| 1.3593 | B.159 | C.17 |
| 1.3594 | B.160 | C.17 |
| 1.3595 | B.161 | C.17 |
| 1.3596 | B.162 | C.17 |
| 1.3597 | B.163 | C.17 |
| 1.3598 | B.164 | C.17 |
| 1.3599 | B.165 | C.17 |
| 1.3600 | B.166 | C.17 |
| 1.3601 | B.167 | C.17 |
| 1.3602 | B.168 | C.17 |
| 1.3603 | B.169 | C.17 |
| 1.3604 | B.170 | C.17 |
| 1.3605 | B.171 | C.17 |
| 1.3606 | B.172 | C.17 |
| 1.3607 | B.173 | C.17 |
| 1.3608 | B.174 | C.17 |
| 1.3609 | B.175 | C.17 |
| 1.3610 | B.176 | C.17 |
| 1.3611 | B.177 | C.17 |
| 1.3612 | B.178 | C.17 |
| 1.3613 | B.179 | C.17 |
| 1.3614 | B.180 | C.17 |
| 1.3615 | B.181 | C.17 |
| 1.3616 | B.182 | C.17 |
| 1.3617 | B.183 | C.17 |
| 1.3618 | B.184 | C.17 |
| 1.3619 | B.185 | C.17 |
| 1.3620 | B.186 | C.17 |
| 1.3621 | B.187 | C.17 |
| 1.3622 | B.188 | C.17 |
| 1.3623 | B.189 | C.17 |
| 1.3624 | B.190 | C.17 |
| 1.3625 | B.191 | C.17 |
| 1.3626 | B.192 | C.17 |
| 1.3627 | B.193 | C.17 |
| 1.3628 | B.194 | C.17 |
| 1.3629 | B.195 | C.17 |
| 1.3630 | B.196 | C.17 |
| 1.3631 | B.197 | C.17 |
| 1.3632 | B.198 | C.17 |
| 1.3633 | B.199 | C.17 |
| 1.3634 | B.200 | C.17 |
| 1.3635 | B.201 | C.17 |
| 1.3636 | B.202 | C.17 |
| 1.3637 | — | C.1 |
| 1.3638 | — | C.2 |
| 1.3639 | — | C.3 |
| 1.3640 | — | C.4 |
| 1.3641 | — | C.5 |
| 1.3642 | — | C.6 |
| 1.3643 | — | C.7 |
| 1.3644 | — | C.8 |
| 1.3645 | — | C.9 |
| 1.3646 | — | C.10 |
| 1.3647 | — | C.11 |
| 1.3648 | — | C.12 |
| 1.3649 | — | C.13 |
| 1.3650 | — | C.14 |
| 1.3651 | — | C.15 |
| 1.3652 | — | C.16 |
| 1.3653 | — | C.17 |

The specific number for each single composition is deductible as follows:

Composition 1.300 for example comprises form C of the compound of formula (I), benzobicyclon (B.98) and benoxacor (C.1) (see table 1, entry 1.300; as well as table B, entry B.98 and table C, entry C.1).

Composition 2.300 for example comprises form A of the compound of formula (I) (see the definition for compositions 2.1 to 2.3653 below), benzobicyclon (B.98) and benoxacor (C.1) (see table 1, entry 1.300; as well as table B, entry B.98 and table C, entry C.1).

Composition 7.300 for example comprises imazapyr (B.35) (see the definition for compositions 7.1 to 7.3653 below), and form C of the compound of formula (I), benzobicyclon (B.98) and benoxacor (C.1) (see table 1, entry 1.300; as well as table B, entry B.98 and table C, entry C.1).

Also especially preferred are compositions 2.1. to 2.3653 which differ from the corresponding compositions 1.1 to 1.3653 only in that they comprise form A as the active component A.

Also especially preferred are compositions 3.1. to 3.3653 which differ from the corresponding compositions 1.1 to 1.3653 only in that they additionally comprise B.2 as further herbicide B.

Also especially preferred are compositions 4.1. to 4.3653 which differ from the corresponding compositions 1.1 to 1.3653 only in that they additionally comprise B.8 as further herbicide B.

Also especially preferred are compositions 5.1. to 5.3653 which differ from the corresponding compositions 1.1 to 1.3653 only in that they additionally comprise B.30 as further herbicide B.

Also especially preferred are compositions 6.1. to 6.3653 which differ from the corresponding compositions 1.1 to 1.3653 only in that they additionally comprise B.32 as further herbicide B.

Also especially preferred are compositions 7.1. to 7.3653 which differ from the corresponding compositions 1.1 to 1.3653 only in that they additionally comprise B.35 as further herbicide B.

Also especially preferred are compositions 8.1. to 8.3653 which differ from the corresponding compositions 1.1 to 1.3653 only in that they additionally comprise B.38 as further herbicide B.

Also especially preferred are compositions 9.1. to 9.3653 which differ from the corresponding compositions 1.1 to 1.3653 only in that they additionally comprise B.40 as further herbicide B.

Also especially preferred are compositions 10.1. to 10.3653 which differ from the corresponding compositions 1.1 to 1.3653 only in that they additionally comprise B.51 as further herbicide B.

Also especially preferred are compositions 11.1. to 11.3653 which differ from the corresponding compositions 1.1 to 1.3653 only in that they additionally comprise B.55 as further herbicide B.

Also especially preferred are compositions 12.1. to 12.3653 which differ from the corresponding compositions 1.1 to 1.3653 only in that they additionally comprise B.56 as further herbicide B.

Also especially preferred are compositions 13.1. to 13.3653 which differ from the corresponding compositions 1.1 to 1.3653 only in that they additionally comprise B.64 as further herbicide B.

Also especially preferred are compositions 14.1. to 14.3653 which differ from the corresponding compositions 1.1 to 1.3653 only in that they additionally comprise B.66 as further herbicide B.

Also especially preferred are compositions 15.1. to 15.3653 which differ from the corresponding compositions 1.1 to 1.3653 only in that they additionally comprise B.67 as further herbicide B.

Also especially preferred are compositions 16.1. to 16.3653 which differ from the corresponding compositions 1.1 to 1.3653 only in that they additionally comprise B.68 as further herbicide B.

Also especially preferred are compositions 17.1. to 17.3653 which differ from the corresponding compositions 1.1 to 1.3653 only in that they additionally comprise B.69 as further herbicide B.

Also especially preferred are compositions 18.1. to 18.3653 which differ from the corresponding compositions 1.1 to 1.3653 only in that they additionally comprise B.73 as further herbicide B.

Also especially preferred are compositions 19.1. to 19.3653 which differ from the corresponding compositions 1.1 to 1.3653 only in that they additionally comprise B.76 as further herbicide B.

Also especially preferred are compositions 20.1. to 20.3653 which differ from the corresponding compositions 1.1 to 1.3653 only in that they additionally comprise B.81 as further herbicide B.

Also especially preferred are compositions 21.1. to 21.3653 which differ from the corresponding compositions 1.1 to 1.3653 only in that they additionally comprise B.82 as further herbicide B.

Also especially preferred are compositions 22.1. to 22.3653 which differ from the corresponding compositions 1.1 to 1.3653 only in that they additionally comprise B.85 as further herbicide B.

Also especially preferred are compositions 23.1. to 23.3653 which differ from the corresponding compositions 1.1 to 1.3653 only in that they additionally comprise B.88 as further herbicide B.

Also especially preferred are compositions 24.1. to 24.3653 which differ from the corresponding compositions 1.1 to 1.3653 only in that they additionally comprise B.89 as further herbicide B.

Also especially preferred are compositions 25.1. to 25.3653 which differ from the corresponding compositions 1.1 to 1.3653 only in that they additionally comprise B.94 as further herbicide B.

Also especially preferred are compositions 26.1. to 26.3653 which differ from the corresponding compositions 1.1 to 1.3653 only in that they additionally comprise B.95 as further herbicide B.

Also especially preferred are compositions 27.1. to 27.3653 which differ from the corresponding compositions 1.1 to 1.3653 only in that they additionally comprise B.98 as further herbicide B.

Also especially preferred are compositions 28.1. to 28.3653 which differ from the corresponding compositions 1.1 to 1.3653 only in that they additionally comprise B.100 as further herbicide B.

Also especially preferred are compositions 29.1. to 29.3653 which differ from the corresponding compositions 1.1 to 1.3653 only in that they additionally comprise B.103 as further herbicide B.

Also especially preferred are compositions 30.1. to 30.3653 which differ from the corresponding compositions 1.1 to 1.3653 only in that they additionally comprise B.103 and B.67 as further herbicides B.

Also especially preferred are compositions 31.1. to 31.3653 which differ from the corresponding compositions 1.1 to 1.3653 only in that they additionally comprise B.103 and B.76 as further herbicides B.

Also especially preferred are compositions 32.1. to 32.3653 which differ from the corresponding compositions 1.1 to 1.3653 only in that they additionally comprise B.103 and B.82 as further herbicides B.

Also especially preferred are compositions 33.1. to 33.3653 which differ from the corresponding compositions 1.1 to 1.3653 only in that they additionally comprise B.104 as further herbicide B.

Also especially preferred are compositions 34.1. to 34.3653 which differ from the corresponding compositions 1.1 to 1.3653 only in that they additionally comprise B.104 and B.67 as further herbicides B.

Also especially preferred are compositions 35.1. to 35.3653 which differ from the corresponding compositions 1.1 to 1.3653 only in that they additionally comprise B.104 and B.76/as further herbicides B.

Also especially preferred are compositions 36.1. to 36.3653 which differ from the corresponding compositions 1.1 to 1.3653 only in that they additionally comprise B.104 and B.82 as further herbicides B.

Also especially preferred are compositions 37.1. to 37.3653 which differ from the corresponding compositions 1.1 to 1.3653 only in that they additionally comprise B.106 as further herbicide B.

Also especially preferred are compositions 38.1. to 38.3653 which differ from the corresponding compositions 1.1 to 1.3653 only in that they additionally comprise B.107 as further herbicide B.

Also especially preferred are compositions 39.1. to 39.3653 which differ from the corresponding compositions 1.1 to 1.3653 only in that they additionally comprise B. 107 and B.67 as further herbicides B.

Also especially preferred are compositions 40.1. to 40.3653 which differ from the corresponding compositions 1.1 to 1.3653 only in that they additionally comprise B. 107 and B.76 as further herbicides B.

Also especially preferred are compositions 41.1. to 41.3653 which differ from the corresponding compositions 1.1 to 1.3653 only in that they additionally comprise B. 107 and B.82 as further herbicides B.

Also especially preferred are compositions 42.1. to 42.3653 which differ from the corresponding compositions 1.1 to 1.3653 only in that they additionally comprise B.109 as further herbicide B.

Also especially preferred are compositions 43.1. to 43.3653 which differ from the corresponding compositions 1.1 to 1.3653 only in that they additionally comprise B.111 as further herbicide B.

Also especially preferred are compositions 44.1. to 44.3653 which differ from the corresponding compositions 1.1 to 1.3653 only in that they additionally comprise B.111 and B.67 as further herbicides B.

Also especially preferred are compositions 45.1. to 45.3653 which differ from the corresponding compositions 1.1 to 1.3653 only in that they additionally comprise B.111 and B.76 as further herbicides B.

Also especially preferred are compositions 46.1. to 46.3653 which differ from the corresponding compositions 1.1 to 1.3653 only in that they additionally comprise B.111 and B.82 as further herbicides B.

Also especially preferred are compositions 47.1. to 47.3653 which differ from the corresponding compositions 1.1 to 1.3653 only in that they additionally comprise B. 116 as further herbicide B.

Also especially preferred are compositions 48.1. to 48.3653 which differ from the corresponding compositions 1.1 to 1.3653 only in that they additionally comprise B.116 and B.67 as further herbicides B.

Also especially preferred are compositions 49.1. to 49.3653 which differ from the corresponding compositions 1.1 to 1.3653 only in that they additionally comprise B.116 and B.94 as further herbicides B.

Also especially preferred are compositions 50.1. to 50.3653 which differ from the corresponding compositions 1.1 to 1.3653 only in that they additionally comprise B.116 and B.103 as further herbicides B.

Also especially preferred are compositions 51.1. to 51.3653 which differ from the corresponding compositions 1.1 to 1.3653 only in that they additionally comprise B.116 and B.128 as further herbicides B.

Also especially preferred are compositions 52.1. to 52.3653 which differ from the corresponding compositions 1.1 to 1.3653 only in that they additionally comprise B.116 and B.104 as further herbicides B.

Also especially preferred are compositions 53.1. to 53.3653 which differ from the corresponding compositions 1.1 to 1.3653 only in that they additionally comprise B.116 and B.107 as further herbicides B.

Also especially preferred are compositions 54.1. to 54.3653 which differ from the corresponding compositions 1.1 to 1.3653 only in that they additionally comprise B.116 and B.111 as further herbicides B.

Also especially preferred are compositions 55.1. to 55.3653 which differ from the corresponding compositions 1.1 to 1.3653 only in that they additionally comprise B.122 as further herbicide B.

Also especially preferred are compositions 56.1. to 56.3653 which differ from the corresponding compositions 1.1 to 1.3653 only in that they additionally comprise B.126 as further herbicide B.

Also especially preferred are compositions 57.1. to 57.3653 which differ from the corresponding compositions 1.1 to 1.3653 only in that they additionally comprise B.128 as further herbicide B.

Also especially preferred are compositions 58.1. to 58.3653 which differ from the corresponding compositions 1.1 to 1.3653 only in that they additionally comprise B.131 as further herbicide B.

Also especially preferred are compositions 59.1. to 59.3653 which differ from the corresponding compositions 1.1 to 1.3653 only in that they additionally comprise B.132 as further herbicide B.

Also especially preferred are compositions 60.1. to 60.3653 which differ from the corresponding compositions 1.1 to 1.3653 only in that they additionally comprise B.133 as further herbicide B.

Also especially preferred are compositions 61.1. to 61.3653 which differ from the corresponding compositions 1.1 to 1.3653 only in that they additionally comprise B.135 as further herbicide B.

Also especially preferred are compositions 62.1. to 62.3653 which differ from the corresponding compositions 1.1 to 1.3653 only in that they additionally comprise B.137 as further herbicide B.

Also especially preferred are compositions 63.1. to 63.3653 which differ from the corresponding compositions 11.1 to 1.3653 only in that they additionally comprise B.138 as further herbicide B.

Also especially preferred are compositions 64.1. to 64.3653 which differ from the corresponding compositions 1.1 to 1.3653 only in that they additionally comprise B.140 as further herbicide B.

Also especially preferred are compositions 65.1. to 65.3653 which differ from the corresponding compositions 1.1 to 1.3653 only in that they additionally comprise B.145 as further herbicide B.

Also especially preferred are compositions 66.1. to 66.3653 which differ from the corresponding compositions 1.1 to 1.3653 only in that they additionally comprise B.153 as further herbicide B.

Also especially preferred are compositions 67.1. to 67.3653 which differ from the corresponding compositions 1.1 to 1.3653 only in that they additionally comprise B.156 as further herbicide B.

Also especially preferred are compositions 68.1. to 68.3653 which differ from the corresponding compositions 1.1 to 1.3653 only in that they additionally comprise B.171 as further herbicide B.

Also especially preferred are compositions 69.1. to 69.3653 which differ from the corresponding compositions 1.1 to 1.3653 only in that they additionally comprise B.174 as further herbicide B.

The invention also relates to agrochemical compositions comprising at least an auxiliary and at least one compound of formula (I) in the form A, B, C and/or D, preferably form C, according to the invention.

An agrochemical composition comprises a pesticidally effective amount of a compound of formula (I) in the form A, B, C and/or D, preferably form C. The term "effective amount" denotes an amount of the composition or of the compounds I, which is sufficient for controlling unwanted plants, especially for controlling unwanted plants in crops (i.e. cultivated plants) and which does not result in a substantial damage to the treated plants. Such an amount can vary in a broad range and is dependent on various factors, such as the plants to be controlled, the treated crops or material, the climatic conditions and the specific compound of formula (I) in the form A, B, C and/or D, preferably form C, used.

Compound of formula (I) in the form A, B, C and/or D, preferably form C, or the plant protection agents containing them can for example be used in the form of directly sprayable aqueous solutions, powders, suspensions and also high concentration aqueous, oily or other suspensions, oil suspensions, pastes, dusting agents, scattering agents or granules by spraying, misting, dusting, scattering or pouring. The use forms are determined by the use purposes; in each case, they should ensure the finest possible distribution of the active substances according to the invention.

The plant protection agents according to the invention contain compound of formula (I) either in form A, B, C and/or D, preferably form C, i.e. in a purity, based on the modification in question, of at least 90 wt. %, and additives and/or carriers such as are usual for the formulation of plant protection agents. In such plant protection agents, the quantity of active substance, i.e. the total quantity of compound of formula (I) and of other active substances if necessary, normally lies in the range from 1 to 98 wt. %, in particular in the range from 10 to 95 wt. %, based on the total weight of the plant protection agent.

All solid and liquid substances which are normally used as carriers in plant protection agents, in particular in herbicide formulations are possible as carriers.

The compound of formula (I) in the form A, B, C and/or D, preferably form C, can be converted into customary types of agrochemical compositions, e. g. suspensions, dusts, powders, pastes, granules, pressings, capsules, and mixtures thereof. Examples for agrochemical composition types are suspensions (e.g. SC, OD, FS), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, 6$^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide.

Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound of formula (I) in the forms A or B on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidones, polyvinylacetates, polyvinyl alcohols, polyacrylates, biological or synthetic waxes, and cellulose ethers.

If the plant protection agents containing the crystalline modification form A, B, C and/or D, preferably form C, are used for seed treatment, they can also contain normal components such as are used for seed treatment, for example in dressing or coating. In addition to the aforesaid components, these include in particular colorants, adhesives, fillers and plasticizers.

All the dyes and pigments usual for such purposes are possible as colorants. Both pigments of low solubility in water and also dyes soluble in water are usable here. As examples, the dyes and pigments known under the names Rhodamin B, C.I. Pigment Red 112 and C.I. Solvent Red 1, Pigment Blue 15:4, Pigment Blue 15:3, Pigment Blue 15:2, Pigment Blue 15:1, Pigment Blue 80, Pigment Yellow 1, Pigment Yellow 13, Pigment Red 48:2, Pigment Red 48:1, Pigment Red 57:1, Pigment Red 53:1, Pigment Orange 43, Pigment Orange 34, Pigment Orange 5, Pigment Green 36, Pigment Green 7, Pigment White 6, Pigment Brown 25, Basic Violet 10, Basic Violet 49, Acid Red 51, Acid Red 52, Acid Red 14, Acid Blue 9, Acid Yellow 23, Basic Red 10, Basic Red 10 and Basic Red 108 may be mentioned. The quantity of colorant will normally not constitute more than 20 wt. % of the formulation and preferably lies in the range from 0.1 to 15 wt. %, based on the total weight of the formulation.

All binders normally usable in dressings come under consideration as adhesives. Examples of suitable binders include thermoplastic polymers such as polyvinylpyrrolidone, polyvinyl acetate, polyvinyl alcohol and tylose and also polyacrylates, polymethacrylates, polybutenes, polyisobutenes, polystyrene, polyethylene amines, polyethylene amides, the aforesaid protective colloids, polyesters, polyether esters, polyanhydrides, polyester urethanes, polyester amides, thermoplastic polysaccharides, for example cellulose derivatives such as cellulose esters, cellulose ethers, cellulose ether esters, including methylcellulose, ethylcellulose, hydroxymethylcellulose, carboxymethylcellulose, hydroxypropyl cellulose and starch derivatives and modified starches, dextrins, maltodextrins, alginates and chitosans, and also fats, oils, proteins, including casein, gelatin and zein, gum Arabic and shellac. The adhesives are preferably plant-compatible, i.e. they exhibit no, or no significant, phytotoxic effects. The adhesives are preferably biodegradable. The adhesive is preferably selected such that it acts as a matrix for the active components of the formulation. The quantity of adhesive will normally not constitute more than 40 wt. % of the formulation and preferably lies in the range from 1 to 40 wt. % and in particular in the range from 5 to 30 wt. %, based on the total weight of the formulation.

In addition to the adhesive, the formulation for seed treatment can also contain inert fillers. Examples of these are the aforesaid solid carriers, in particular finely divided inorganic materials such as clays, chalk, bentonite, kaolin, talc, perlite, mica, silica gel, diatomaceous earth, quartz powder and montmorillonite but also fine-particle organic materials such as wood flour, cereal flour, active charcoal and the like. The quantity of filler is preferably selected such that the total quantity of filler does not exceed 70 wt. %, based on the total weight of all non-volatile components of the formulation. Often, the quantity of filler lies in the range from 1 to 50 wt. %, based on the total weight of all non-volatile components of the formulation.

In addition, the formulation for seed treatment can also contain a plasticizer which increases the flexibility of the coating. Examples of plasticizers are oligomeric polyalkylene glycols, glycerine, dialkyl phthalates, alkylbenzyl phthalates, glycol benzoates and comparable compounds. The quantity of plasticizer in the coating often lies in the range from 0.1 to 20 wt. %, based on the total weight of all non-volatile components of the formulation.

A preferred embodiment of the invention relates to liquid formulations of the form A, B, C and/or D, preferably form C. In addition to the solid active substance phase, these have at least one liquid phase, in which compound of formula (I) is present in form A, B, C and/or D, preferably form C, in the form of dispersed fine particles.

Possible liquid phases are essentially water and those organic solvents in which the form A, B, C and/or D, preferably form C, is only slightly soluble, or insoluble, for example those wherein the solubility of the form A or form B at 25° C. and 1013 mbar is not more than 1 wt. %, in particular not more than 0.1 wt. %, and especially not more than 0.01 wt. %.

According to a first preferred embodiment, the liquid phase is selected from water and aqueous solvents, i.e. solvent mixtures which in addition to water also contain up to 20 wt. %, preferably however not more than 10 wt. %, based on the total quantity of water and solvent, of one or more organic solvents miscible with water, for example ethers miscible with water such as tetrahydrofuran, methyl glycol, methyl diglycol, alkanols such as isopropanol or polyols such as glycol, glycerine, diethylene glycol, propylene glycol and the like. Such formulations are also referred to below as suspension concentrates (SCs).

Such suspension concentrates contain compound of formula (I) as form A, B, C and/or D, preferably form C, in a finely divided particulate form, wherein the particles of the form A, B, C and/or D, preferably form C, are present suspended in an aqueous phase. The size of the active substance particles, i.e. the size which 90 wt. % of the active substance particles do not exceed, here typically lies below 30 µm, in particular below 20 µm. Advantageously, in the SCs according to the invention, at least 40 wt. % and in particular at least 60 wt. % of the particles have diameters below 2 µm.

In such SCs the quantity of active substance, i.e. the total quantity of compound of formula (I) and of other active substances if necessary, usually lies in the range from 5 to 70 wt. %, in particular in the range from 10 to 50 wt. %, based on the total weight of the suspension concentrate.

In addition to the active substance, aqueous suspension concentrates typically contain surface-active substances, and also if necessary antifoaming agents, thickeners (=rheology modifiers), antifreeze agents, stabilizers (biocides), agents for adjusting the pH and anticaking agents.

Possible surface-active substances are the previously named surface-active substances. Preferably the aqueous plant protection agents according to the invention contain at least one of the previously named anionic surfactants and if necessary one or more nonionic surfactants, if necessary in combination with a protective colloid. The quantity of surface-active substances will as a rule be 1 to 50 wt. %, in particular 2 to 30 wt. %, based on the total weight of the aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

Concerning the nature and quantity of the antifoaming agents, thickeners, antifreeze agents and biocides, the same applies as aforesaid.

If necessary, the aqueous SCs according to the invention can contain buffers for pH regulation. Examples of buffers are alkali metal salts of weak inorganic or organic acids, such as for example phosphoric acid, boric acid, acetic acid, propionic acid, citric acid, fumaric acid, tartaric acid, oxalic acid and succinic acid.

According to a second preferred embodiment, the liquid phase consists of non-aqueous organic solvents in which the solubility of the form A, B, C and/or D, preferably form C, of compound of formula (I) at 25° C. and 1013 mbar is not more than 1 wt. %, in particular not more than 0.1 wt. %, and especially not more than 0.01 wt. %. These include in particular aliphatic and cycloaliphatic hydrocarbons and oils, in particular those of plant origin, and also $C_1$-$C_4$ alkyl esters of saturated or unsaturated fatty acids or fatty acid mixtures, in particular the methyl esters, for example methyl oleate, methyl stearate and rape oil methyl ester, but also paraffinic mineral oils and the like.

Accordingly, the present invention relates also to agents for plant protection in the form of a non-aqueous suspension concentrate, which will also be referred to below as OD (oil-dispersion). Such ODs contain the form A, B, C and/or D, preferably form C, of compound of formula (I) in a finely divided particulate form, wherein the particles of the form A, B, C and/or D, preferably form C, are present suspended in a non-aqueous phase. The size of the active substance particles, i.e. the size which 90 wt. % of the active substance particles do not exceed, here typically lies below 30 µm, in particular below 20 µm.

Advantageously, in the non-aqueous suspension concentrates, at least 40 wt. % and in particular at least 60 wt. % of the particles have diameters below 2 µm.

In such ODs, the quantity of active substance, i.e. the total quantity of compound of formula (I) and of other active substances if necessary, usually lies in the range from 5 to 70 wt. %, in particular in the range from 10 to 50 wt. %, based on the total weight of the non-aqueous suspension concentrate.

In addition to the active substance and the liquid carrier, non-aqueous suspension concentrates typically contain surface-active substances, and also if necessary antifoaming agents, agents to modify the rheology and stabilizers (biocides).

Possible surface-active substances are preferably the previously named anionic and nonionic surfactants. The quantity of surface-active substances will as a rule be 1 to 30 wt. %, in particular 2 to 20 wt. %, based on the total weight of the non-aqueous SCs according to the invention. Preferably the surface-active substances include at least one anionic surface-active substance and at least one nonionic surface-active substance, and the proportion of anionic to nonionic surface-active substance typically lies in the range from 10:1 to 1:10.

The form A, B, C and/or D, preferably form C, of compound of formula (I) according to the invention can also be formulated as solid plant protection agents. These include powder, scattering and dusting agents but also water-dispersible powders and granules, for example coated, impregnated and homogenous granules. Such formulations can be produced by mixing or simultaneous grinding of the form A, B, C and/or D, preferably form C, of compound of formula (I) with a solid carrier and if necessary other additives, in particular surface-active substances. Granules can be produced by binding of the active substances to solid carriers. Solid carriers are mineral earths such as silicic acids, silica gels, silicates, talc, kaolin, limestone, lime, chalk, bole, loess, clay, dolomite, diatomaceous earth, calcium and magnesium sulfate, magnesium oxide, ground plastics, fertilizers such as ammonium sulfate, ammonium phosphate, ammonium nitrate, ureas and plant products such as cereal flour, tree bark, wood and nutshell flour, cellulose powder or other solid carriers. Solid formulations can also be produced by spray drying, if necessary in the presence of polymeric or inorganic drying aids, and if necessary in the presence of solid carriers.

For the production of solid formulations of compounds of formula (I) in form A, B, C and/or D, preferably form C, extrusion processes, fluidized bed granulation, spray granulation and comparable technologies are suitable.

Possible surface-active substances are the previously named surfactants and protective colloids. The quantity of surface-active substances will as a rule be 1 to 30 wt. %, in particular 2 to 20 wt. %, based on the total weight of the solid formulation according to the invention.

In such solid formulations, the quantity of active substance, i.e. the total quantity of compound of formula (I) and of other active substances if necessary, usually lies in the range from 5 to 70 wt. %, in particular in the range from 10 to 50 wt. %, based on the total weight of the solid formulation.

Examples for agrochemical composition types (i.e. formulation examples) and their preparation are:

i) Water-Soluble Concentrates (SL, LS)

10-60 wt % of form A, B, C and/or D, preferably form C, or a herbicidal composition comprising at least one compound of formula (I) in form A, B, C and/or D (component A), preferably form C, and at least one further compound selected from the herbicidal compounds B (component B) and safeners C (component C) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of form A, B, C and/or D, preferably form C, or a herbicidal composition comprising at least one compound of formula (I) in form A, B, C and/or D (component A), preferably form C, and at least one further compound selected from the herbicidal compounds B (component B) and safeners C (component C) according to the invention and 1-10 wt % dispersant (e. g. polyvinylpyrrolidone) are dissolved in organic solvent (e.g. cyclohexanone) ad 100 wt %. Dilution with water gives a dispersion.

iii) Suspensions (SC, OD, FS)

In an agitated ball mill, 20-60 wt % of form A, B, C and/or D, preferably form C, or a herbicidal composition comprising at least one compound of formula (I) in form A, B, C and/or D (component A), preferably form C, and at least one further compound selected from the herbicidal compounds B (component B) and safeners C (component C) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

iv) Water-Dispersible Granules and Water-Soluble Granules (WG, SG)

50-80 wt % of form A, B, C and/or D, preferably form C, or a herbicidal composition comprising at least one compound of formula (I) in form A, B, C and/or D (component A), preferably form C, and at least one further compound selected from the herbicidal compounds B (component B) and safeners C (component C) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

v) Water-Dispersible Powders and Water-Soluble Powders (WP, SP, WS)

50-80 wt % of form A, B, C and/or D, preferably form C, or a herbicidal composition comprising at least one compound of formula (I) in form A, B, C and/or D (component A), preferably form C, and at least one further compound selected from the herbicidal compounds B (component B) and safeners C (component C) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

vi) Gel (GW, GF)

In an agitated ball mill, 5-25 wt % of form A, B, C and/or D, preferably form C, or a herbicidal composition comprising at least one compound of formula (I) in form A, B, C and/or D (component A), preferably form C, and at least one further compound selected from the herbicidal compounds B (component B) and safeners C (component C) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

vii) Microcapsules (CS)

An oil phase comprising 5-50 wt % of form A, B, C and/or D, preferably form C, or a herbicidal composition comprising at least one compound of formula (I) form A, B, C and/or D (component A), preferably form C, and at least one further compound selected from the herbicidal compounds B (component B) and safeners C (component C) according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of form A or B according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

iix) Dustable Powders (DP, DS)

1-10 wt % of form A, B, C and/or D, preferably form C, or a herbicidal composition comprising at least one compound of formula (I) in form A, B, C and/or D (component A), preferably form C, and at least one further compound selected from the herbicidal compounds B (component B) and safeners C (component C) according to the invention are ground finely and mixed intimately with solid carrier (e.g. finely divided kaolin) ad 100 wt %.

ix) Granules (GR, FG)

0.5-30 wt % of form A, B, C and/or D, preferably form C, or a herbicidal composition comprising at least one compound of formula (I) in form A, B, C and/or D (component A), preferably form C, and at least one further compound selected from the herbicidal compounds B (component B) and safeners C (component C) according to the invention is ground finely and associated with solid carrier (e.g. silicate) ad 100 wt %. Granulation is achieved by extrusion, spray-drying or the fluidized bed.

The agrochemical compositions types i) to ix) may optionally comprise further auxiliaries, such as 0.1-1 wt % bactericides, 5-15 wt % anti-freezing agents, 0.1-1 wt % anti-foaming agents, and 0.1-1 wt % colorants.

The application of the form A, B, C and/or D, preferably form C, or the herbicidal agents containing them is effected, if the formulation is not already ready for use, in the form of aqueous spray fluids. These are prepared by dilution of the aforesaid formulations containing the form A, B, C and/or D, preferably form C, with water. The spray fluids can also contain other components in dissolved, emulsified or suspended form, for example fertilizers, active substances of other herbicidal or growth-regulating active substance groups, other active substances, for example active substances for combating animal pests or phyto-pathogenic fungi or bacteria, and also mineral salts which are used for the elimination of nutritional and trace element deficiencies, and non-phytotoxic oils and oil concentrates. As a rule, these components are added to the spray fluid before, during or after the dilution of the formulations according to the invention.

The application of the form A, B, C and/or D, preferably form C, or of the plant protection agents containing them can be effected in a pre-emergence or in a post-emergence method. If compound of formula (I) is less tolerable for certain crop plants, application techniques can be used wherein the herbicidal agents are sprayed using the spraying equipment in such a manner that the leaves of the sensitive crop plants are as far as possible not hit, while the active substances reach the leaves of undesired plants growing under them or the uncovered soil surface (post-directed, lay-by).

The quantities of compound of formula (I) applied are 0.001 to 3.0 kg active substance per hectare, preferably 0.005 to 0.25 kg active substance (a.s.)/ha, depending on the treatment aim, season, target plants and growth stage.

In a further embodiment, the application of the form A, B, C and/or D, preferably form C, or the plant protection agent containing them can be effected by treatment of seed.

Treatment of seed essentially includes all techniques with which the person skilled in the art is familiar (seed dressing, seed coating, seed dusting, seed soaking, seed film coating, seed multilayer coating, seed encrusting, seed dripping and seed pelleting) on the basis of compound of formula (I) in form A, B, C and/or D, preferably form C, or agents prepared therefrom. Here the plant protection agents can be applied diluted or undiluted.

The term seed includes seed of all types, for example grains, seeds, fruits, tubers, cuttings and similar forms. Preferably, the term seed here describes grains and seeds.

As seed, seed of the crop plants mentioned above but also the seeds of transgenic plants or those obtained by conventional breeding methods can be used.

For the seed treatment, compound of formula (I) in form A, B, C and/or D, preferably form C, is normally used in quantities of 0.001 to 10 kg per 100 kg of seed.

The following illustrations and examples serve to illustrate the invention and should not be regarded as limiting.

FIG. 1 shows an X-ray powder diffraction diagram of form A. The X-ray diffraction diagram of form A was recorded with a Panalytical X'Pert Pro diffractometer (manufacturer: Panalytical) in reflection geometry (Bragg-Brantano) in the range from 2θ=3°-40° with increments of e.g. 0.017° and measurement time of 20 s/step using using Cu-Kα radiation (1.54178 Å) at 25° C. The tube voltage was 45 kV and current 40 mA. The sample was placed in a silicon single crystal sample holder of 0.2 mm depth and flattened.

Figure 1:
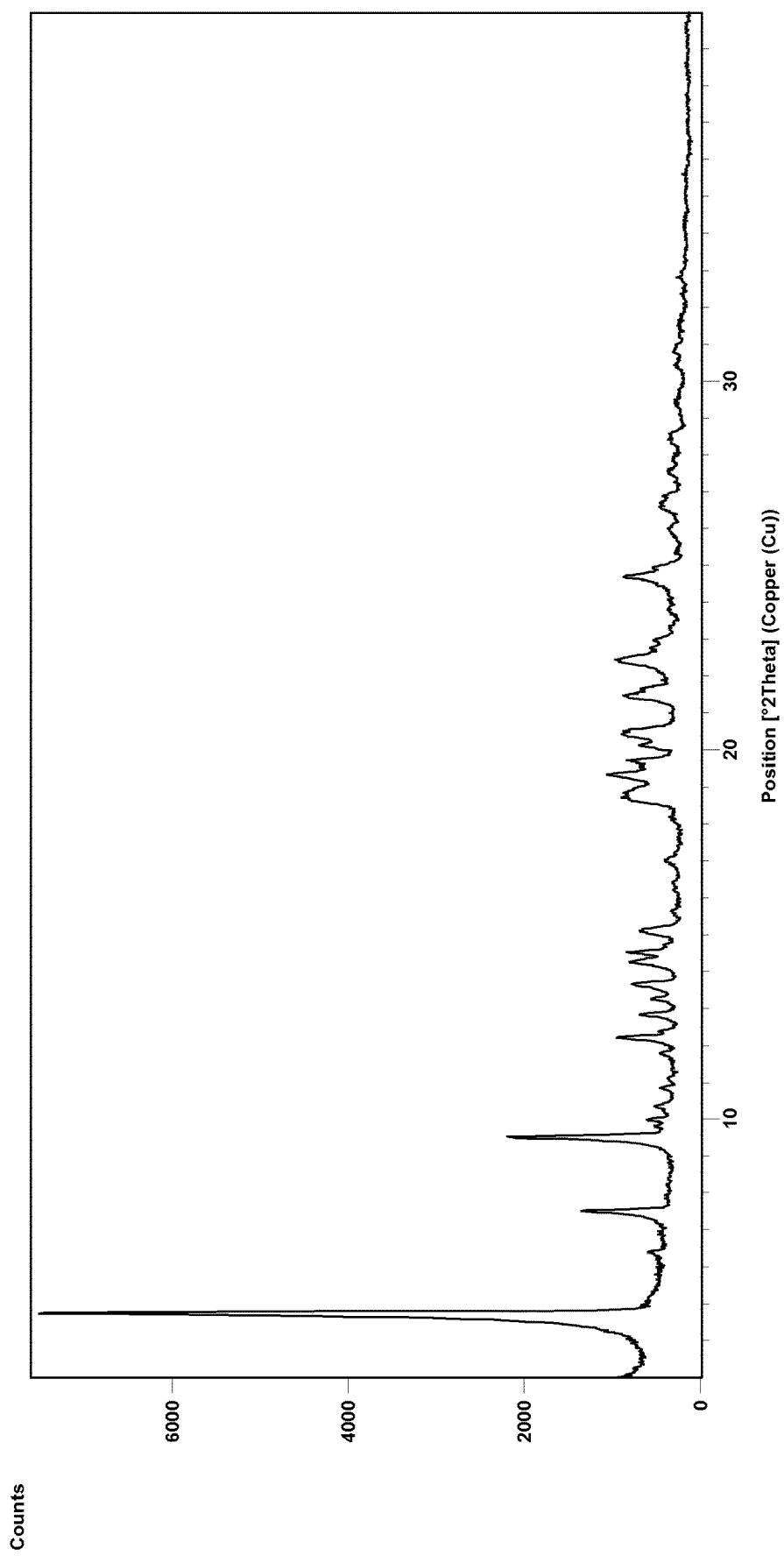
Figure 2:
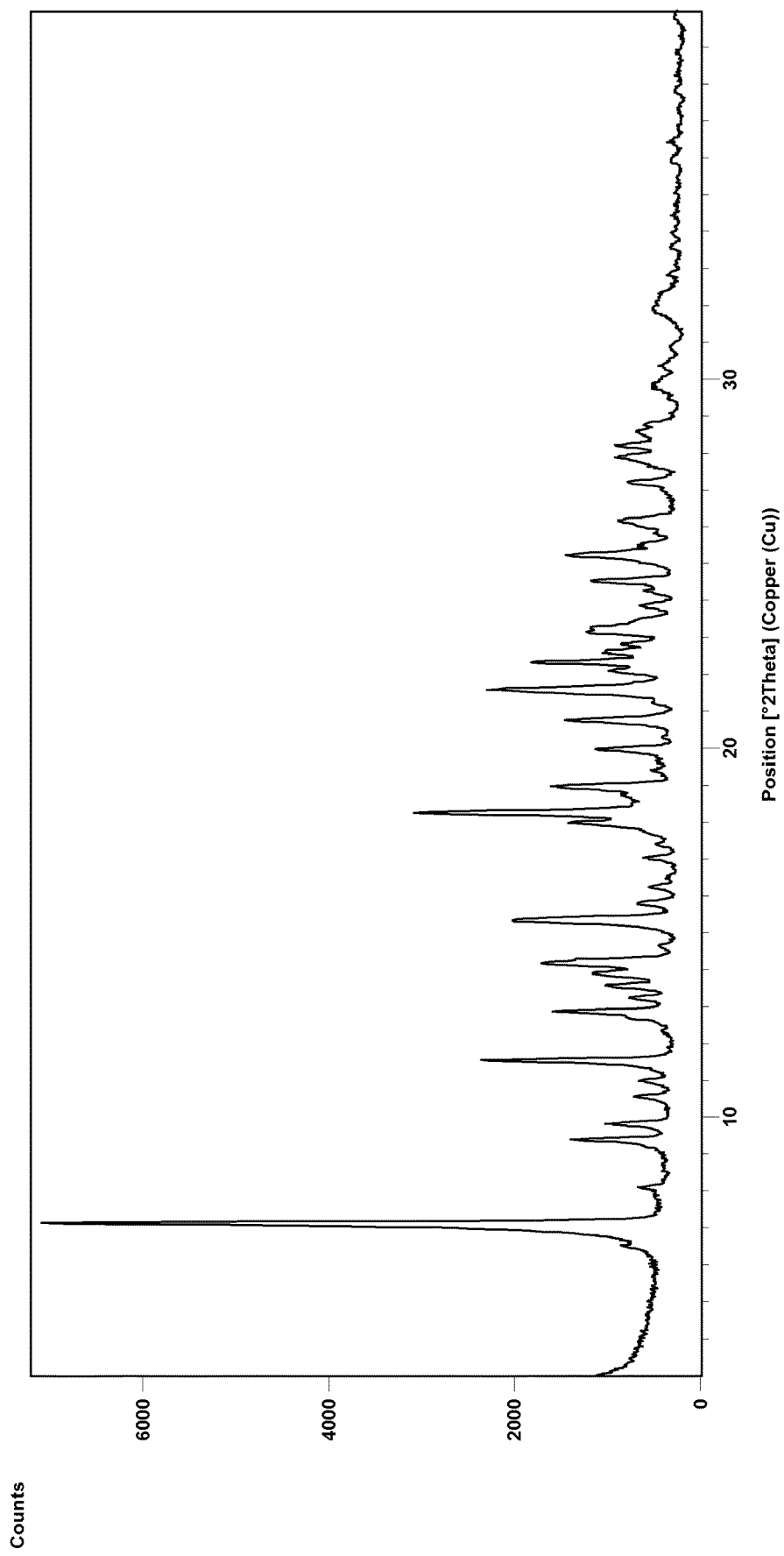
FIG. 2 shows an X-ray powder diffraction diagram of form B. The X-ray diffraction diagram was recorded under the conditions stated for FIG. 1.
Figure 3:
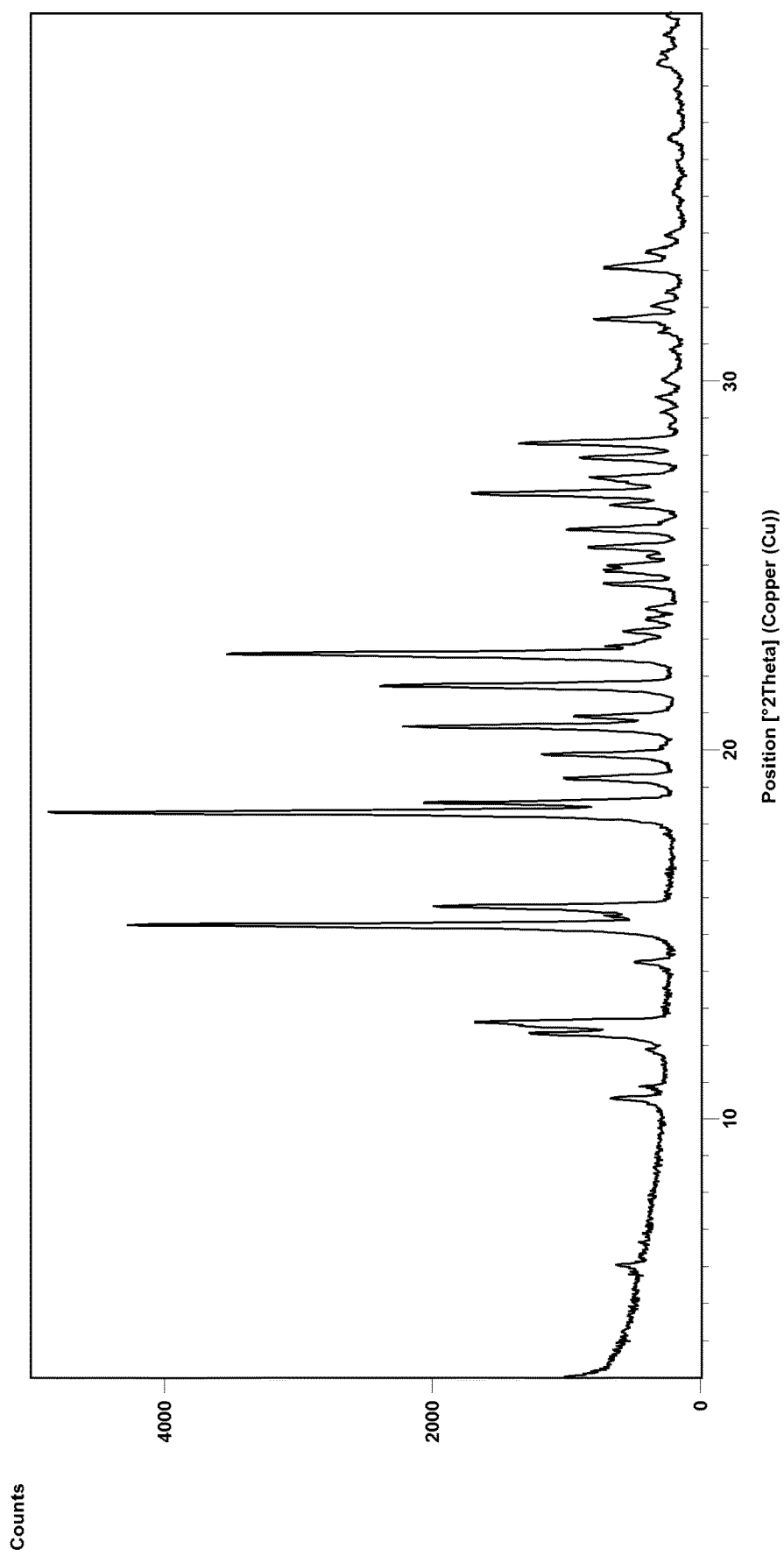
FIG. 3 shows an X-ray powder diffraction diagram of form C. The X-ray diffraction diagram was recorded under the conditions stated for FIG. 1.
Figure 4:
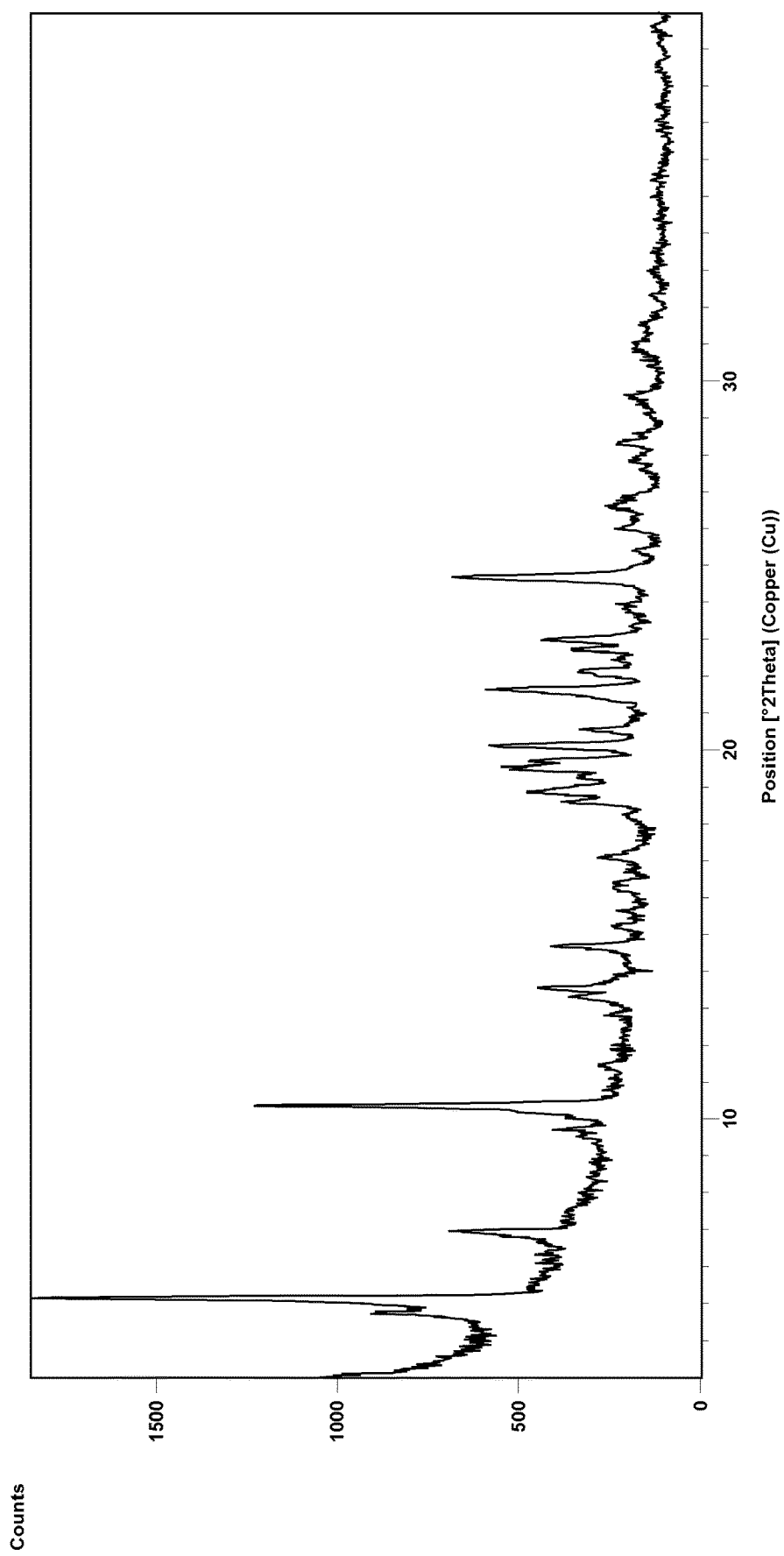
FIG. 4 shows an X-ray powder diffraction diagram of form C. The X-ray diffraction diagram was recorded under the conditions stated for FIG. 1.

The melting points were determined using DSC with a Mettler Toledo DSC 823e/700/229 module. The samples were placed in aluminum standard pans. The sample size in each case was 1 to 10 mg. The heating rate was 10° C./min. The samples were purged with a stream of nitrogen during the experiment. The melting point was determined as the extrapolated peak onset temperature (also called onset temperature) defined by the point of intersection of the tangent at the half height of the melting peak, on the principal side of the peak with the linelarily extrapolated initial base line.

Single crystal X-ray diffraction: X-ray diffraction data were collected on a Bruker AXS 8D Pro-spector diffractometer at 100 K with Cu-Kα radiation (1.5418 Å). The images were processed with Saint (Bruker AXS) and the structure was solved with SHELXS and refined with SHELXL.

A PREPARATION EXAMPLES

The preparation of the compound of formula (I) and its forms A, B, C and D is illustrated by the following examples;

Example 1

Ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate

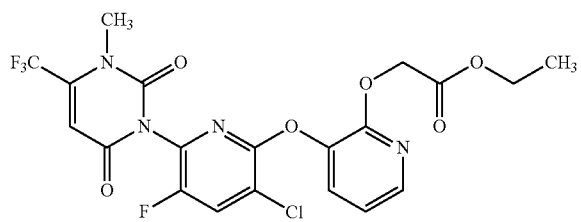

Example 1 Step 1: Ethyl 2-[[3-[(6-azido-3-chloro-5-fluoro-2-pyridyl)oxy]-2-pyridyl]oxy]acetate

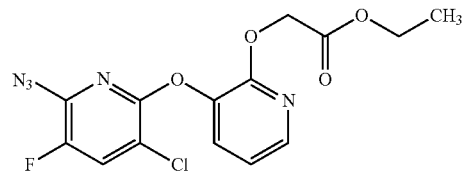 [SMILES: CCOC(=O)COc1ncccc1Oc1nc(N=[N+]=[N-])c(F)cc1Cl]

To a solution of 1.8 g (10.78 mmol) 3-chloro-2,5,6-trifluoropyridine (CAS 2879-42-7) in 20 mL DMSO at room temperature was added 0.77 g (11.8 mmol) sodium azide and the mixture was stirred 3 hours at room temperature. Then a suspension of 2.2 g (11.3 mmol) ethyl 2-[(3-hydroxy-2-pyridyl)oxy]acetate (CAS: 353292-81-6) and 7 g (21.5 mmol) Cs$_2$CO$_3$ in 10 mL DMSO was added to the above mixture in portions. The resulting mixture was stirred at room temperature for 15 hours, diluted with water and extracted with ethyl acetate. The combined organic layer was washed with brine, dried over anhydrous Na$_2$SO$_4$, filtered and the solvent was removed under reduced pressure. The crude title product was used without further purification in the next step.

Example 1 Step 2: Ethyl 2-[[3-[(6-amino-3-chloro-5-fluoro-2-pyridyl)oxy]-2-pyridyl]oxy]acetate

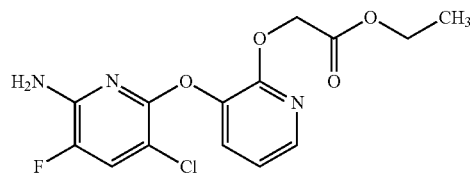 [SMILES: CCOC(=O)COc1ncccc1Oc1nc(N)c(F)cc1Cl]

To a suspension of 4.8 g (13 mmol) of compound 1 step 1 and 4.3 g (66 mmol) zinc in 100 mL THF was added dropwise 50 mL semi-saturated aqueous NH$_4$Cl solution at 0° C. The mixture was stirred at room temperature for 5 hours, filtered and the filter cake was washed with ethyl acetate. To the filtrate was added 200 mL water, the mixture was extracted with ethyl acetate, the organic layer was dried over anhydrous Na$_2$SO$_4$, filtered and the solvent was removed under reduced pressure. The crude product was purified by column chromatography on silica (petrol ether/ethyl acetate) to give 2.7 g (8 mmol, 61%) of the desired title product.

$^1$H-NMR (CDCl$_3$, ppm): 7.9 (dd, J=4.89 Hz, J=1.51 Hz, 1H); 7.4 (d, J=7.39 Hz, 1H); 7.3 (d, J=9.06 Hz, 1H); 6.9 (dd, J=7.65 Hz, J=4.89 Hz, 1H); 4.9 (s, 2H); 4.5 (s, 2H); 4.2 (q, J=7.15 Hz, 2H); 1.25 (t, J=7.15 Hz, 3H).

[M+H]=428.1; Rt=1.332 min

Example 1 Step 3: Ethyl(Z)-3-(dimethylcarbamoylamino)-4,4,4-trifluoro-but-2-enoate

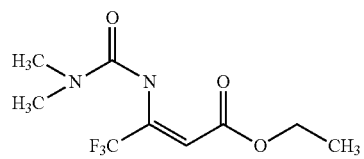 [SMILES: CCOC(=O)/C=C(\NC(=O)N(C)C)C(F)(F)F]

To a solution of 104 g (2.73 mol) NaH in 600 mL dry DMF under a N$_2$-atmosphere was added 233 g (2.18 mol) N,N-dimethylcarbamoyl chloride (CAS: 79-44-7) dissolved in 200 mL dry DMF dropwise over 1 hour at 0-5° C. with stirring. Then 200 g (1.09 mol) ethyl (Z)-3-amino-4,4,4-trifluoro-but-2-enoate (CAS: 372-29-2) dissolved in 200 mL dry DMF was added dropwise at a temperature of 0-5° C. over 1 hour with stirring. The mixture was stirred at room temperature for another 2 hours and then poured into ice-water. The mixture was extracted with ethyl acetate, the combined organic layer was washed with brine, dried over anhydrous Na$_2$SO$_4$, filtered and the solvent was removed under reduced pressure. The crude product was purified by column chromatography on silica (petrol ether/ethyl acetate) to give 170 g (0.67 mol, 64%) of the desired product 1 step 3.

Example 1 Step 4: Example 5.2: 2-(dimethylamino)-4-(trifluoromethyl)-1,3-oxazin-6-one

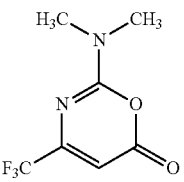

To a solution of 170 g (0.67 mol) of compound 1 step 3 in 102 mL POCl$_3$ was added 139 g (0.67 mol) PCl$_5$ at 0° C. in three portions with 15 minutes stirring in between and the mixture was stirred another hour at 0° C. The mixture was then stirred at room temperature for another 3 hours. The reaction mixture was poured into 250 mL ice water and the precipitate was collected via filtration and dried to give 84 g (0.40 mol, 60%) of the desired product 1 step 4.

$^1$H-NMR (CDCl$_3$, ppm): 5.9 (s, 1H); 3.2 (d, J=19.58 Hz, 6H).

[M+H]=209.1; Rt=0.980 min

Example 1 Step 5: Ethyl 2-[[3-[[3-chloro-6-[2,4-dioxo-6-(trifluoromethyl)-1H-pyrimidin-3-yl]-5-fluoro-2-pyridyl]oxy]-2-pyridyl]oxy]acetate

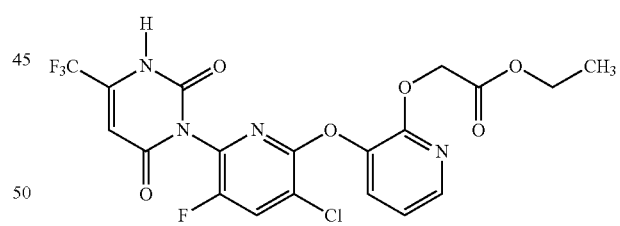

A solution of 16 g (47 mmol) of compound 1 step 2 and 9.8 g (47 mmol) of compound 5.2 in 430 mL glacial acetic acid was stirred at 80° C. for 16 hours. Then 9.8 g (47 mmol) of compound 1 step 4 was added and the mixture stirred at 80° C. for 16 hours. Again 2.9 g (14 mmol) of compound 1 step 4 was added and the mixture stirred at 80° C. for 16 hours. Again 9.8 g (47 mmol) of compound 1 step 4 was added and the mixture stirred at 80° C. for 16 hours. Then water was added, the mixture was extracted with ethyl acetate, the combined organic layer was washed with water and brine, dried over anhydrous Na$_2$SO$_4$, filtered and the solvent was removed under reduced pressure. The crude product 1 step 5 (23 g, 46 mmol, 97%) was used in the next step without further purification.

Example 1 Step 6: Ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate

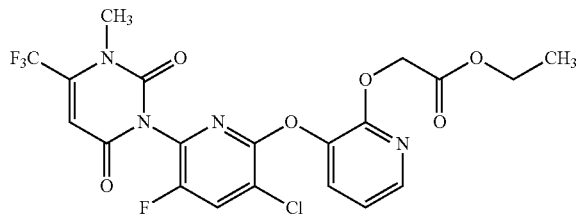 [SMILES: CCOC(=O)COc1ncccc1Oc1nc(-n2c(=O)cc(C(F)(F)F)n(C)c2=O)c(F)cc1Cl]

To a solution of 23 g (46 mmol) of the crude compound 1 step 5 in 500 mL DMF was added 38 g (275 mmol) K$_2$CO$_3$ followed by 26.6 g (187 mmol) methyl iodide at 0° C. The reaction mixture was stirred at room temperature for 16 hours, then 38 g (275 mmol) K$_2$CO$_3$ was added again followed by 26.6 g (187 mmol) methyl iodide and the mixture was again stirred at room temperature for 48 hours. The mixture was poured into water, extracted with ethyl acetate, the combined organic layer was washed with water and brine, dried over anhydrous Na$_2$SO$_4$, filtered and the solvent was removed under reduced pressure. The crude product was purified by reversed phase preparative HPLC (acetonitrile/water containing trifluoroacetic acid) to give 10.3 g (19.9 mmol, 43%) of the desired compound 1 ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate.

$^1$H-NMR (CDCl$_3$, ppm): 7.96 (d, J=3.97 Hz, 1H); 7.76 (d, J=7.50 Hz, 1H); 7.49 (d, J=7.06 Hz, 1H); 6.95 (dd, J=7.50 Hz, J=5.29 Hz, 1H); 6.26 (s, 1H) 4.79 (s, 2H); 4.19 (q, J=7.06 Hz, 2H); 3.48 (s, 3H); 1.24 (t, J=7.06 Hz, 3H).

[M+H]=519.0; Rt=1.183 min

Example 2: Preparation of Form a of Compound of Formula (I)

100 mg amorphous compound of formula (I) was dissolved in 1 mL 2-propanole. After about 30 min, a crystalline precipitate was obtained, isolated and characterized by PXRD (powder X-ray powder diffractometry), TG (thermogravimetry) and DSC (differential scanning calorimetry).

On the basis of the characteristic reflections, form A was identified.

Example 3: Preparation of Form B of Compound of Formula (I)

23.88 g amorphous compound of formula (I) was dissolved in 20 mL 2-propanole. After 90 min a clear brown solution was observed, after 100 min the solution turned turbid, some precipitate was obtained. The suspension was stirred for 22 h, then the solvent was evaporated using rotary evaporator. 17.58 g of a white solid were obtained, which was characterized by PXRD, TG and DSC.

On the basis of the characteristic reflections, form B was identified.

Example 3: Preparation of Form C of Compound of Formula (I)

84 mL 2PrOH were added to 8.40 g amorphous compound of formula (I) and the content was stirred overnight. Some precipitate was obtained, which was filtered and washed with 5 mL 2-propanole. The solid was dried using rotary evaporator and 5.50 g of a white solid were obtained, which was characterized by PXRD, TG and DSC.

On the basis of the characteristic reflections, form C was identified.

Example 4: Preparation of Form D of Compound of Formula (I)

70 mL 2PrOH were added to 11.2 g amorphous compound of formula (I), the mixture was stirred overnight (precipitate). The suspension was filtered and the solid material was dried using a rotary evaporator. 8.5 g of a white solid were obtained, which was characterized by PXRD, TG and DSC.

On the basis of the characteristic reflections, form D was identified.

The invention claimed is:

1. A crystalline form C of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate, which in an X-ray powder diffraction diagram at 25° C. and Cu-Kα radiation displays at least 3 of the following reflections, quoted as ° 2θ values: 10.6±0.2, 12.3±0.2, 15.3±0.2, 15.8±0.2, 18.3±0.2, 18.6±0.2, 19.2±0.2, 19.9±0.2, 20.6±0.2, 20.9±0.2, 21.8±0.2, 22.6±0.2, 24.5±0.2, 25.5±0.2, 26.0±0.2, 27.0±0.2 and 28.3±0.2.

2. The crystalline form C as claimed in claim 1 with a content of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate of at least 94 wt. %.

3. Ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate consisting of at least 90 wt. % of the crystalline form C.

4. The process for production of the crystalline form C as claimed in claim 1, comprising:
   i) preparation of a solution of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate in a solvent which is selected from the group consisting of aliphatic hydrocarbons, aromatic hydrocarbons, esters, ketones and alcohols;
   ii) effecting a crystallization of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate.

5. A crystalline form A of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate, which in an X-ray powder diffraction diagram at 25° C. and Cu-Kα radiation displays at least 3 of the following reflections, quoted as ° 2θ values: 4.7±0.2, 7.5±0.2, 9.5±0.2, 12.2±0.2, 12.9±0.2, 13.7±0.2, 14.3±0.2, 14.5±0.2, 19.3±0.2, 20.1±0.2 and 24.7±0.2.

6. A crystalline form B of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate, which in an X-ray powder diffraction diagram at 25° C. and Cu-Kα radiation displays at least 3 of the following reflections, quoted as ° 2θ values: 7.1±0.2, 9.4±0.2, 9.8±0.2, 11.6±0.2, 13.6±0.2, 13.9±0.2, 15.3±0.2, 18.3±0.2, 19.0±0.2, 20.0±0.2, 20.8±0.2, 21.6±0.2, 22.3±0.2, 24.5±0.2 and 27.2±0.2.

7. A crystalline form D of ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate, which in an X-ray powder diffraction diagram at 25° C. and Cu-Kα radiation displays at least 3 of the following reflections, quoted as ° 2θ values: 5.2±0.2, 6.9±0.2, 10.4±0.2, 14.7±0.2, 18.9±0.2, 20.1±0.2, 21.6±0.2, 22.1±0.2, 23.0±0.2 and 24.7±0.2.

8. A plant protection agent containing ethyl 2-[[3-[[3-chloro-5-fluoro-6-[3-methyl-2,6-dioxo-4-(trifluoromethyl)pyrimidin-1-yl]-2-pyridyl]oxy]-2-pyridyl]oxy]acetate, which consists of one or more of crystalline forms A, B, C, and D in at least 90 wt %, and one or more additives customary for the formulation of plant protection agents.

9. The plant protection agent as claimed in claim 8 in the form of an aqueous suspension concentrate.

10. The plant protection agent as claimed in claim 8 in the form of a non-aqueous suspension concentrate.

11. The plant protection agent as claimed in claim 8 in the form of a powder or granules dispersible in water.

12. A method for combatting undesired plant growth comprising applying to plants, the habitat thereof, or seeds an effective amount of an agent containing ethyl 2-[[3-[[3-chloro-5-fluoro-6-[3-methyl-2,6-dioxo-4-(trifluoromethyl)pyrimidin-1-yl]-2-pyridyl]pxy] acetate, wherein one or more crystalline forms A, B, C, and D is present in at least 90 wt %.

* * * * *